(12) United States Patent
Metcalf, III et al.

(10) Patent No.: US 8,507,647 B2
(45) Date of Patent: Aug. 13, 2013

(54) ANTIBACTERIAL AGENTS FOR THE TREATMENT OF GRAM POSITIVE INFECTIONS

(75) Inventors: Chester A. Metcalf, III, Needham, MA (US); Jing Li, Lansdale, PA (US); Andre Lee Pearson, Somerville, MA (US)

(73) Assignee: Cubist Pharmaceuticals, Inc., Lexington, MA (US)

( * ) Notice: Subject to any disclaimer, the term of this patent is extended or adjusted under 35 U.S.C. 154(b) by 481 days.

(21) Appl. No.: 12/641,465

(22) Filed: Dec. 18, 2009

(65) Prior Publication Data

US 2010/0184649 A1 Jul. 22, 2010

Related U.S. Application Data

(60) Provisional application No. 61/139,875, filed on Dec. 22, 2008.

(51) Int. Cl.
*C07K 11/02* (2006.01)

(52) U.S. Cl.
USPC .......................................... 530/317; 514/2.4

(58) Field of Classification Search
USPC .......................................... 530/317; 514/2.4
See application file for complete search history.

(56) References Cited

U.S. PATENT DOCUMENTS

| | | |
|---|---|---|
| 3,854,480 A | 12/1974 | Zaffaroni |
| 4,396,543 A | 8/1983 | Debono |
| 4,399,067 A | 8/1983 | Debono |
| 4,452,775 A | 6/1984 | Kent |
| 4,482,487 A | 11/1984 | Abbott et al. |
| 4,524,135 A | 6/1985 | Abbott et al. |
| 4,537,717 A | 8/1985 | Abbott et al. |
| RE32,310 E | 12/1986 | Debono |
| RE32,311 E | 12/1986 | Debono |
| RE32,333 E | 1/1987 | Hamill et al. |
| RE32,455 E | 7/1987 | Hamill et al. |
| 5,039,660 A | 8/1991 | Leonard et al. |
| 5,041,567 A | 8/1991 | Rogers et al. |
| 5,573,936 A | 11/1996 | Kreuzman et al. |
| 5,629,288 A | 5/1997 | Lattrell et al. |
| 5,912,226 A | 6/1999 | Baker et al. |
| 6,468,967 B1 | 10/2002 | Oleson, Jr. et al. |
| 6,624,143 B1 | 9/2003 | Vértesy et al. |
| 6,794,490 B2 | 9/2004 | Hill et al. |
| 6,852,689 B2 | 2/2005 | Oleson, Jr. et al. |
| 6,911,525 B2 | 6/2005 | Hill et al. |
| RE39,071 E | 4/2006 | Baker et al. |
| 7,262,268 B2 | 8/2007 | Morytko et al. |
| 7,335,725 B2 | 2/2008 | Hill et al. |
| 7,335,726 B2 | 2/2008 | Morytko et al. |
| 7,408,025 B2 | 8/2008 | Hill et al. |

FOREIGN PATENT DOCUMENTS

| | | |
|---|---|---|
| EP | 0 178 152 | 4/1986 |
| EP | 0 095 295 B1 | 1/1987 |
| EP | 0 885 957 A1 | 12/1998 |
| WO | WO 95/05384 A1 | 2/1995 |
| WO | WO 99/43700 | 9/1999 |
| WO | WO 01/33274 A1 | 6/2001 |
| WO | WO 01/44271 A2 | 6/2001 |
| WO | WO 01/44272 A2 | 6/2001 |
| WO | WO 03/014147 A1 | 2/2003 |
| WO | WO 2006/110185 A2 | 10/2006 |

OTHER PUBLICATIONS

Ackermann G. et al, In vitro activity of OPT-80 against *Clostridium difficile*. Antimicrob Agents Chemother. Jun. 2004; 48(6): 2280-2.

Akhtar AJ et al., Increasing incidence of *Clostridium difficile*-associated diarrhea in African-American and Hispanic patients: association with the use of proton pump inhibitor therapy. J Natl Med Assoc. May 2007; 99(5): 500-4.

Alekshun MN, New advances in antibiotic development and discovery. Expert Opin Investig Drugs. Feb. 2005; 14(2): 117-34.

Alekshun MN et al., Commensals upon us. Biochem Pharmacol. Mar. 30, 2006; 71(7): 893-900. Epub Feb. 7, 2006.

Al-Nassir WN et al., Comparison of clinical and microbiological response to treatment of *Clostridium difficile*-associated disease with metronidazole and vancomycin. Clin Infect Dis. Jul. 1, 2008; 47(1): 56-62.

Ananthakrishnan AN et al., Excess hospitalisation burden associated with *Clostridium difficile* in patients with inflammatory bowel disease. Gut. Feb. 2008; 57(2): 205-10. Epub Sep. 28, 2007.

Anton PM, et al., Rifalazil treats and prevents relapse of *Clostridium difficile*-associated diarrhea in hamsters. Antimicrob Agents Chemother. Oct. 2004; 48(10): 3975-9.

Apisarnthanarak A., et al., Adjunctive intracolonic vancomycin for severe *Clostridium difficile* colitis: Case series and review of the literature. Clinical Infectious Diseases. 2002; 35(6): 690-696.

Apostolopoulou E et al., Infection Probability Score: a predictor of *Clostridium difficile*-associated disease onset in patients with haematological malignancy. Eur J Oncol Nurs. Dec. 2, 2010.

Arango JI, et al., Incidence of *Clostridium difficile*-associated diarrhea before and after autologous peripheral blood stem cell transplantation for lymphoma and multiple myeloma. Bone Marrow Transplant. Mar. 2006; 37(5): 517-21.

Aspevall O et al., Antimicrobial susceptibility pattern of *Clostridium difficile* and its relation to PCR ribotypes in a Swedish university hospital. Antimicrob Agents Chemother. May 2006; 50(5): 1890-2.

Barberan J. et al., Observational retrospective study to evaluate nephrotoxicity of daptomycin and vancomycin in the treatment of Gram-positive infections. Clinical Microbiology and Infection. 2012; 18: 650.

Barbut F et al., Clinical features of *Clostridium difficile*-associated diarrhoea due to binary toxin (actin-specific ADP-ribosyltransferase)-producing strains. J Med Microbiol. Feb. 2005; 54(Pt 2): 181-5.

Barbut F et al. Clinical features of *Clostridium difficile*-associated infections and molecular characterization of strains: results of a retrospective study 2000-2004. Infect Control Hosp Epidemiol. Feb. 2007; 28(2): 131-9. Epub Jan. 24, 2007.

(Continued)

Primary Examiner — David Lukton
(74) Attorney, Agent, or Firm — Finnegan, Henderson, Farabow, Garrett & Dunner, LLP

(57) ABSTRACT

The present invention relates to novel lipopeptide compounds, pharmaceutical compositions of these compounds and methods of using these compounds as antibacterial compounds. The compounds of the invention are particularly useful against a variety of bacteria, including resistant strains. The compounds are useful as antibacterial agents against *Clostridium difficile*.

15 Claims, No Drawings

(56) References Cited

OTHER PUBLICATIONS

Bardak-Ozcem S. et al., Daptomycin vs. vancomycin in the treatment of methicillin-resistant *Staphylococcus aureus* meningitis in experimental rabbit model. Clinical Microbiology and Infection. 2012; 18: 595.
Barker RH et al., Review article: tolevamer a novel toxin-binding polymer: overview of preclinical pharmacology and physicochemical properties. Aliment Pharmacol Ther. Dec. 2006; 24(11-12): 1525-34.
Barr D.A. et al., Outpatient parenteral antimicrobial therapy (OPAT) in a teaching hospital-based practice: A retrospective cohort study describing experience and evolution over 10 years. International Journal of Antimicrobial Agents. 2012; 39(5): 407-413.
Bartlett JG, Historical perspectives on studies of *Clostridium difficile* and *C. difficile* infection. Clin Infect Dis. Jan. 15, 2008; 46 Suppl 1: S4-11.
Bauer J. et al., Comparison of anti-MRSA antibiotics (vancomycin linezolid daptomycin rifampin) and anti Gram-positive fluoroquinolones (moxifloxacin delafloxacin) against MSSA and MRSA in models of young and mature biofilms. Clinical Microbiology and Infection. 2012; 18: 594.
Benson L. et al., Changing epidemiology of *Clostridium difficile*-associated disease in children. Infect Control Hosp Epidemiol. Nov. 2007; 28(11): 1233-5. Epub Aug. 27, 2007.
Beraud G. et al., Pharmacokinetics of high-dose daptomycin in haemodialysis. Clinical Microbiology and Infection. 2012; 18: 733.
Bhakta A. et al., A creep in the vancomycin minimum inhibitory concentration for *Staphylococcus aureus* in a tertiary care hospital in India. Critical Care. 2011; 15: S81-S82.
Bishara J et al., Antimicrobial resistance of *Clostridium difficile* isolates in a tertiary medical center Israel. Diagn Microbiol Infect Dis. Feb. 2006; 54(2): 141-4. Epub Jan. 9, 2006.
Bokesch P. et al., Pharmacokinetics of daptomycin in infants: Implications for dosing. Clinical Microbiology and Infection. 2012; 18: 445.
Bourgault AM et al., In vitro susceptibility of *Clostridium difficile* clinical isolates from a multi-institutional outbreak in Southern Quebec Canada. Antimicrob Agents Chemother. Oct. 2006; 50(10): 3473-5.
Boyanova L. et al., Antimicrobial resistance and the management of anaerobic infections. Expert Rev Anti-Inf. 2007; 5(4): 685-701.
Buer J. et al., MRSA—Current developments pressing problems: (Based on a lecture during the VUD Conference in Essen on Jun. 18, 2010). Krankenhaushygiene und Infektionsverhutung. 2010; 32(5): 144-150.
Burdette SD et al., The Odiferous Diagnosis of *Clostridium difficile* Associated Diarrhea. IDSA. Oct. 12-15, 2006; Toronto Ontario Canada 1054.
Butler M.S. et al., Antibiotics in the clinical pipeline in 2011. Journal of Antibiotics. 2011; 64(6): 413-425.
Butler MS et al., Natural products—the future scaffolds for novel antibiotics? Biochem Pharmacol. Mar. 30, 2006; 71(7): 919-29. Epub Nov. 14, 2005.
Cafiso V. et al., Modulating activity of vancomycin and daptomycin on the expression of autolysis cell-wall turnover and membrane charge genes in hVISA and VISA strains. Clinical Microbiology and Infection. 2012; 18: 322.
Carroll KC et al., Biology of *Clostridium difficile*: Implications for Epidemiology and Diagnosis. Annu Rev Microbiol. Jun. 16, 2011.
Cassettari M. et al., In vitro activity of telavancin against staphylococci circulating in Europe during 2010 and 2011. Clinical Microbiology and Infection. 2012; 18: 537.
Castagnola E et al., *Clostridium difficile*-associated disease in children with solid tumors. Support Care Cancer. Mar. 2009; 17(3): 321-4. Epub Sep. 19, 2008.
Cercenado E. et al., Discrepancies between MicroScan Etest and broth microdilution for the determination of daptomycin susceptibility in enterococci. Clinical Microbiology and Infection. 2012; 18: 457.
Chalvatzi K. et al., In vitro activities of telavancin and three comparator agents against *Staphylococcus aureus*. Clinical Microbiology and Infection. 2012; 18: 756.
Chandler RE et al., *Clostridium difficile*-associated disease in Oregon: increasing incidence and hospital-level risk factors. Infect Control Hosp Epidemiol. Feb. 2007; 28(2): 116-22. Epub Jan. 31, 2007.
Chen X et al., A mouse model of *Clostridium difficile*-associated disease. Gastroenterology. Dec. 2008; 135(6): 1984-92. Epub Sep. 10, 2008.
Chesnel L et al., Treatment of CDI With Oral CB-183 315 Delays Recurrence and Decreases Relapse Rates Compared to Vancomycin. ECCMID. Mar. 31-Apr. 3 2012; London England P1439.
Citron DM, Impact of CB-183 315 a Novel Lipopeptide on Fecal Flora of 30 Subjects in a Phase I Clinical Trial. ICCAC Sep. 12-15, 2010; Boston MA.
Citron DM et al., In Vitro Activity of CB-183 315 Against 556 Strains of *Clostridium Difficile* 446 Strains of Intestinal Anaerobes and 56 Facultative Strains of Enterobacteriaceae. ICCAC Sep. 12-15, 2010; Boston MA E-2063.
Cole P. et al., Highlights from the 50$^{th}$ interscience conference on antimicrobial agents and chemotherapy (ICCAC). Drugs Future. 2010; 35(12):1045-1067.
Cote GA et al., Antibiotic-associated diarrhoea. Expert Opin Drug Saf. May 2006; 5(3): 361-72.
Cotter PD et al., Bacterial Iantibiotics: strategies to improve therapeutic potential. Curr Protein Pept Sci. Feb. 2005; 6(1): 61-75.
Cottreau J et al., Rifaximin: a nonsystemic rifamycin antibiotic for gastrointestinal infections. Expert Rev Anti Infect Ther. Jul. 2010; 8(7): 747-60.
Credito KL et al., Activity of OPT-80 a novel macrocycle compared with those of eight other agents against selected anaerobic species. Antimicrob Agents Chemother. Nov. 2004; 48(11): 4430-4.
Croft AC et al., Update on the antibacterial resistance crisis. Med Sci Monit. Jun. 2007; 13(6): RA103-18.
Curry SR et al., High Frequency of Rifampin Resistance Identified in an Epidemic *Clostridium difficile* Clone from a Large Teaching Hospital. Clin Infect Dis. Jan. 13, 2009.
Dendukuri N et al., Probiotic therapy for the prevention and treatment of *Clostridium difficile*-associated diarrhea: a systematic review. CMAJ. Jul. 19, 2005; 173(2): 167-70.
Deshpande A et al., Do fluoroquinolones predispose patients to *Clostridium difficile* associated disease? A review of the evidence. Curr Med Res Opin. Feb. 2008; 24(2): 329-33.
Deshpande A et al., Association between proton pump inhibitor therapy and *Clostridium difficile* infection in a meta-analysis. Clin Gastroenterol Hepatol. Mar. 2012; 10(3): 225-33. Epub Oct. 20, 2011.
Dohmen P. et al., Results from the European Cubicin(r) Outcomes Registry and Experience (EU-CORE): High success rates with daptomycin in the treatment of patients with sepsis. Clinical Microbiology and Infection. 2012; 18: 522.
Dolgin E, 'Game changer' antibiotic and others in works for superbug. Nat Med. Jan. 2011; 17(1): 10.
Drudy D et al., Toxin A-negative toxin B-positive *Clostridium difficile*. Int J Infect Dis. Jan. 2007; 11(1): 5-10. Epub Jul. 20, 2006.
Dubberke E.R. et al., Severity of *Clostridium difficile*-associated disease (CDAD) in allogeneic stem cell transplant recipients: Evaluation of a CDAD severity grading system. Infection Control and Hospital Epidemiology. 2007; 28(2): 208-211.
Dupont HL et al., New advances in *Clostridium difficile* infection: changing epidemiology diagnosis treatment and control. Curr Opin Infect Dis. Oct. 2008; 21(5): 500-7.
Eckstein BC et al., Reduction of *Clostridium Difficile* and vancomycin-resistant *Enterococcus* contamination of environmental surfaces after an intervention to improve cleaning methods. BMC Infect Dis. Jun. 21, 2007; 7: 61.
El Sayed F. et al., Reliable activity of daptomycin on *Staphylococcus epidermidis* from bone and joint infections. Clinical Microbiology and Infection. 2012; 18: 540.
Farkas A., Population probability of target attainment of daptomycin at different levels of renal function against methicillinresistant

*Staphylococcus aureus* in European medical centres. Clinical Microbiology and Infection. 2012; 18: 436.

Farkas A., Optimal dosing of Daptomycin in the morbidly obese: Which body weight is it? Clinical Microbiology and Infection. 2012; 18: 732.

Ferreira CE et al., Prevalence of *Clostridium spp.* and *Clostridium difficile* in children with acute diarrhea in Sao Paulo city Brazil. Mem Inst Oswaldo Cruz. Jun. 2003; 98(4): 451-4. Epub Aug. 18, 2003.

Fishman N, Antimicrobial stewardship. Am J Med. Jun. 2006; 119 (6 Suppl 1): S53-61; discussion S62-70.

Freedman SD et al., Case records of the Massachusetts General Hospital. Case 26-2009. A 34-year-old man with cystic fibrosis with abdominal pain and distention. N Engl J Med. Aug. 20, 2009; 361(8): 807-16.

Fujitani S et al., Comparison of clinical severity score indices for *Clostridium difficile* infection. Infect Control Hosp Epidemiol. Mar. 2011;32(3):220-8.

Garcia-Castillo M. et al., Telavancin in vitro activity against relevant Gram-positive isolates (Target multicenter study) prospectively collected from ICU patients in Spain Clinical Microbiology and Infection. 2012; 18: 537-538.

Garey K.W. et al., Rifamycin antibiotics for treatment of *Clostridium difficile*-associated diarrhea. Ann Pharmacother. 2008; 42(6): 827-835.

Gasch O. et al., Daptomycin MIC increase among patients with methicillin-resistant *Staphylococcus aureus* persistent bacteraemia treated with daptomycin. Prospective study in 22 Spanish hospitals. Clinical Microbiology and Infection. 2012; 18: 650.

Gavalda J. et al., Assessment of antibiotic lock technique with daptomycin vancomycin for the treatment of coagulase-negative staphylococci experimental catheter infection. Clinical Microbiology and Infection. 2012; 18: 595.

Gerber M. et al., OPT-80 a macrocyclic antimicrobial agent for the treatment of *Clostridium difficile* infections: A review. Expert Opin Invest Drugs. 2008; 17(4): 547-553.

Gerding DN, Metronidazole for *Clostridium difficile*-associated disease: is it okay for Mom? Clin Infect Dis. Jun. 1, 2005; 40(11): 1598-600. Epub Apr. 25, 2005.

Geric B et al., Distribution of *Clostridium difficile* variant toxinotypes and strains with binary toxin genes among clinical isolates in an American hospital. J Med Microbiol. Sep. 2004;53(Pt 9):887-94.

Ghantoji S. et al., Economic healthcare costs of *Clostridium difficile* infection: A systematic review. J Hosp Infect. 2010; 74(4): 309-318.

Glance LG et al., Increases in Mortality Length of Stay and Cost Associated With Hospital-Acquired Infections in Trauma Patients. Arch Surg. Mar. 21, 2011.

Goldenberg S et al., A two-step glutamatedehydrogenase antigen: Real-time polymerase chain reaction assay for detection of toxigenic *Clostridium difficile*. Clinical Microbiology and Infection. 2009; 15: S195.

Goldstein EJ, Beyond the target pathogen: ecological effects of the hospital formulary. Curr Opin Infect Dis. Feb. 2011; 24 Suppl 1: S21-31.

Goldstein EJC, Beyond the target pathogen: ecological effects of the hospital formulary, Current Opinion in Infectious Diseases. 2011; 24(suppl 1): S21-S31.

Gonzalez Ramallo V.J. et al., Results from a non-interventional study: Daptomycin is effective as outpatient parenteral antibiotic therapy. Clinical Microbiology and Infection. 2012; 18: 522-523.

Gonzalez-Ruiz A. et al., Daptomycin as first-line therapy for infections in patients with solid tumours: Clinical experience from the European Registry. Clinical Microbiology and Infection. 2012; 18: 612.

Gonzalez-Ruiz A. et al., Evaluation of safety and efficacy of daptomycin therapy in elderly: Results from a patient registry in Europe. Clinical Microbiology and Infection. 2012; 18: 649.

Goodman B.M. et al., Infectious disease emergencies: Frontline clinical pearls. Medical Clinics of North America. 2012; 96(6): 1033-1066.

Gould CV et al., Bench-to-bedside review: *Clostridium difficile* colitis. Crit Care. 2008; 12(1): 203. Epub Jan. 18, 2008.

Guleri A. et al., Management of infective endocarditis: An innovative multidisciplinary pathway to manage a complex disease-clinical experience from a Lancashire cardiac centre Clinical Microbiology and Infection. 2012; 18: 843.

Guleri A. et al., Daptopmycin elevated creatine phosphokinase and rhabdomyolysis-is there a co-relation? Clinical experience from the UK EU-CORESM registry 2006-2011 (RP 1-4). Clinical Microbiology and Infection. 2012; 18: 649-650.

Guo B et al., Systematic review: faecal transplantation for the treatment of *Clostridium difficile*-associated disease. Aliment Pharmacol Ther. Apr. 2012; 35(8): 865-75. doi: 10.1111/j.1365-2036.2012. 05033.x. Epub Feb. 23, 2012.

Hall A.D. et al., Evaluation of standard and high-dose daptomycin vs. linezolid against vancomycin-resistant *Enterococcus faecalis* in an in vitro model of simulated endocardial vegetations. Clinical Microbiology and Infection. 2012; 18: 438.

Hall A.D. et al., High-dose daptomycin vs. vancomycin alone or combined with clarithromycin or rifampin against methicillinresistant *Staphylococcus epidermidis* in an in vitro pharmacokinetic/pharmacodynamic model of bacterial biofilm. Clinical Microbiology and Infection. 2012; 18: 437-438.

Halliday J et al., Targeting the forgotten transglycosylases. Biochem Pharmacol. Mar. 30, 2006; 71(7): 957-67. Epub Nov. 18, 2005.

Hassan S.A. et al., Mechanism of action of XF-70 a novel porphyrin antimicrobial against *Staphylococcus epidermidis*. Clinical Microbiology and Infection. 2012; 18: 377.

Hassan S.A. et al., Activity of XF-70 a novel porphyrin antimicrobial against biofilms of *Staphylococcus epidermidis*. Clinical Microbiology and Infection. 2012; 18: 378.

Hecht DW et al., In vitro activities of 15 antimicrobial agents against 110 toxigenic *Clostridium difficile* clinical isolates collected from 1983 to 2004. Antimicrob Agents Chemother. Aug. 2007; 51(8): 2716-9. Epub May 21, 2007.

Hookman P et al., *Clostridium difficile* associated infection diarrhea and colitis. World J Gastroenterol. Apr. 7, 2009; 15(13): 1554-80.

Huebner ES et al., Treatment of recurrent *Clostridium difficile* diarrhea. Gastroenterology & Hepatology; 2006; 2(3): 203-208.

Imhoff A et al., Is there a future for probiotics in preventing *Clostridium difficile*-associated disease and treatment of recurrent episodes? Nutr Clin Pract. Feb.-Mar. 2009; 24(1): 15-32.

Jabes D., The antibiotic R&D pipeline: An update. Current Opinion in Microbiology. 2011; 14(5): 564-569.

Jangi S et al., Asymptomatic colonization by *Clostridium difficile* in infants: implications for disease in later life. J Pediatr Gastroenterol Nutr. Jul. 2010; 51(1): 2-7.

Jenkins D et al., Antibiotic Quantitative (QUAN) and Qualitative (QUAL) Policies: Differential Effects on *Clostridium difficile*-Associated Diarrhea (CDAD). ICAAC & IDSA. Oct. 25-28, 2008; Washington DC USA. K-518.

Johnson AP, Drug evaluation: OPT-80 a narrow-spectrum macrocyclic antibiotic. Curr Opin Investig Drugs. Feb. 2007; 8(2): 168-73.

Johnson AP, New antibiotics for selective treatment of gastrointestinal infection caused by *Clostridium difficile*. Expert Opin Ther Pat. Oct. 2010; 20(10): 1389-99.

Johnson S et al., Interruption of recurrent *Clostridium difficile*-associated diarrhea episodes by serial therapy with vancomycin and rifaximin. Clin Infect Dis. Mar. 15, 2007; 44(6): 846-8. Epub Feb. 2, 2007.

Johnson S. et al., *Clostridium difficile*—Associated diarrhea. Clin Infect Dis. 1998; 26(5): 1027-1036.

Jump RL et al., Vegetative *Clostridium difficile* survives in room air on moist surfaces and in gastric contents with reduced acidity: a potential mechanism to explain the association between proton pump inhibitors and *C. difficile*-associated diarrhea? Antimicrob Agents Chemother. Aug. 2007;51(8): 2883-7. Epub Jun. 11, 2007.

Kaya S. et al., Treatment of left-sided gram-positive endocarditis with daptomycin. Clinical Microbiology and Infection. 2012; 18: 523-524.

Keil F. et al., Results from the European Cubicin(r) Outcomes Registry and Experience: Daptomycin is effective as first-line treatment for Gram-positive infections in patients with haematological malignancies. Clinical Microbiology and Infection. 2012; 18: 612.

Kelly C.P. et al., *Clostridium difficile*—More difficult than ever. New England Journal of Medicine. 2008; 359(18): 1932-1940.

Kelly CP, Current strategies for management of initial *Clostridium difficile* infection. J Hosp Med. Mar. 2012; 7 Suppl 3: S5-10. doi: 10.1002/jhm.1909.

Kern W.V. et al., Nosocomial infections: MRSA und CDAD as a challenge. Internist. 2009; 50(6): 691-705.

Khanna S et al., The growing incidence and severity of *Clostridium difficile* infection in inpatient and outpatient settings. Expert Rev Gastroenterol Hepatol. Aug. 2010; 4(4): 409-16.

Kink JA et al., Antibodies to recombinant *Clostridium difficile* toxins A and B are an effective treatment and prevent relapse of *C. difficile*-associated disease in a hamster model of infection. Infect Immun. May 1998; 66(5): 2018-25.

Kirst HA, Recent derivatives from smaller classes of fermentation-derived antibacterials. Expert Opin Ther Pat. Dec. 2011.

Klarin B et al., *Lactobacillus plantarum* 299v reduces colonisation of *Clostridium difficile* in critically ill patients treated with antibiotics. Acta Anaesthesiol Scand. Sep. 2008; 52(8): 1096-102.

Knobloch J., MIC determination for daptomycin using VITEK2: The DaVIT multicentre study. Clinical Microbiology and Infection. 2012; 18: 456.

Konychev A. et al., A comparative randomised clinical trial against semisynthetic penicillins and glycopeptides supports the use of daptomycin as first-line treatment of complicated skin and soft-tissue infections in the elderly. Clinical Microbiology and Infection. 2012; 18: 838-839.

Kosmidis CI et al., Management of Gram-positive Bacterial Infections in Cancer patients. Leuk Lymphoma. Jul. 6, 2011.

Kuijper EJ et al., Emergence of *Clostridium difficile*-associated disease in North America and Europe. Clin Microbiol Infect. Oct. 2006; 12 Suppl 6: 2-18.

Kuijper EJ et al., *Clostridium difficile*: changing epidemiology and new treatment options. Curr Opin Infect Dis. Aug. 2007; 20(4): 376-83.

Kuijper EJ et al., Decreased effectiveness of metronidazole for the treatment of *Clostridium difficile* infection? Clin Infect Dis. Jul. 1, 2008; 47(1): 63-5.

Kyne L, *Clostridium difficile*—beyond antibiotics. N Engl J Med. Jan. 21, 2010; 362(3): 264-5.

Langley JM et al., The role of *Clostridium difficile* and viruses as causes of nosocomial diarrhea in children. Infect Control Hosp Epidemiol. Nov. 2002; 23(11): 660-4.

Lautenbach E et al., Resistant gram-negative bacilli: A neglected healthcare crisis? Am J Health Syst Pharm. Dec. 1, 2007; 64(23 Suppl 14): S3-21; quiz S22-4.

Lefebvre Sl et al., Prevalence of zoonotic agents in dogs visiting hospitalized people in Ontario: implications for infection control. J Hosp Infect. Apr. 2006; 62(4): 458-66. Epub Feb. 7, 2006.

Lepainteur M. et al., Phenotypic and genotypic characterisation of coagulase negative *Staphylococci bacteraemic* isolates from infected very low birth weight neonates: Antibiotic and antiseptic susceptibility biofilm production and clonality. Clinical Microbiology and Infection. 2012; 18: 283.

Lightowler M. et al., Outcomes of antimicrobial stewardship intervention in a Spanish university hospital. Clinical Microbiology and Infection. 2012; 18: 771.

Lim T.P. et al., Comparative activity of various antibiotics alone and in combination against high inocula methicillin-resistant *Staphylococcus aureus* with reduced susceptibilities to vancomycin. Clinical Microbiology and Infection. 2012; 18: 539.

Loo VG et al., A predominantly clonal multi-institutional outbreak of *Clostridium difficile*-associated diarrhea with high morbidity and mortality. N Engl J Med. Dec. 8, 2005; 353(23): 2442-9. Epub Dec. 1, 2005.

Louie T et al., Results of a phase III trial comparing tolevamer vancomycin and metronidazole in patients with *Clostridium difficile*-associated diarrhoea (CDAD) [abstract K-425a]. In: Program and abstracts of the 47th Annual Interscience Conference on Antimicrobial Agents and Chemotherapy (Chicago). Program and abstracts of the 47th Annual Interscience Conference on Antimicrobial Agents and Chemotherapy (Chicago) 2007.

Louie T., Antimicrobial stewardship: A review. Infectious Diseases in Clinical Practice. 2011; 19(6): 382-387.

Louie T. et al., Clinical outcomes safety and pharmacokinetics of OPT-80 in a phase 2 trial with patients with *Clostridium difficile* infection. Antimicrobial Agents and Chemotherapy. 2009; 53(1): 223-228.

Louie TJ, How should we respond to the highly toxogenic NAP1/ribotype 027 strain of *Clostridium difficile*? CMAJ. Oct. 25, 2005; 173(9): 1049-50.

Louie TJ et al., Tolevamer a novel nonantibiotic polymer compared with vancomycin in the treatment of mild to moderately severe *Clostridium difficile*-associated diarrhea. Clin Infect Dis. Aug. 15, 2006; 43(4): 411-20. Epub Jul. 11, 2006.

Lu C. et al., Microbiologic and clinical characteristics of vancomycin resistant *Enterococcus faecium* bacteraemia in Taiwan: a retrospective cohort study. Clinical Microbiology and Infection. 2012; 18: 329.

Luna RA et al., Rapid stool-based diagnosis of *Clostridium difficile* infection by real-time PCR in a children's hospital. J Clin Microbiol. Mar. 2011; 49(3): 851-7. Epub Jan. 5, 2011.

Luo R. et al., Resource utilization and costs of treating complicated skin and skin structure infections with daptomycin or telavancin Value in Health. 2012; 15(4): A239.

Lyras D et al., Toxin B is essential for virulence of *Clostridium difficile*. Nature. Apr. 30, 2009; 458(7242): 1176-9. Epub Mar. 1, 2009.

Malmberg C. et al., Colistin in combination with daptomycin enhances the effect against *A. baumannii*. Clinical Microbiology and Infection. 2012; 18: 511-512.

Marculescu CE et al., Unusual aerobic and anaerobic bacteria associated with prosthetic joint infections. Clin Orthop Relat Res. Oct. 2006; 451: 55-63.

Mascio C et al., Mechanism of Action Acquisition of Resistance and Post Antibiotic Effect of Lipopeptide Antibiotic CB-183 315. ICCAC Sep. 12-15, 2010; Boston MA C1-097.

Mascio C.T.M. et al., In Vitro and in Vivo characterization of CB-183 315 a novel lipopeptide antibiotic for treatment of *Clostridium difficile*. Antimicrobial Agents and Chemotherapy. 2012; 56(10): 5023-5030.

McCormack P. et al., Influence of demographic and pathophysiological factors on the probability of target attainment for intravenous antibiotics used in the treatment of methicillin-resistant *Staphylococcus aureus* complicated skin and soft-tissue infections Clinical Microbiology and Infection. 2012; 18: 436.

McDonald LC, Trends in antimicrobial resistance in health care-associated pathogens and effect on treatment. Clin Infect Dis. Jan. 15, 2006; 42 Suppl 2: S65-71.

McDonald LC et al., An epidemic toxin gene-variant strain of *Clostridium difficile*. N Engl J Med. Dec. 8, 2005; 353(23): 2433-41. Epub Dec. 1, 2005.

McFarland LV, Alternative treatments for *Clostridium difficile* disease: what really works? J Med Microbiol. Feb. 2005; 54(Pt 2): 101-11.

McFarland LV, Update on the changing epidemiology of *Clostridium difficile*-associated disease. Nat Clin Pract Gastroenterol Hepatol. Jan. 2008; 5(1): 40-8.

McFarland LV, Emerging therapies for *Clostridium difficile* infections. Expert Opin Emerg Drugs. Mar. 28, 2011.

Mendes R. et al., Genotypic and phenotypic characterisation of methicillinresistant *Staphylococcus aureus* strains recovered from a phase IV clinical trial for linezolid vs. vancomycin for the treatment of nosocomial pneumonia. Clinical Microbiology and Infection. 2012; 18: 343.

Mendes R. et al., Oritavancin activity tested against *Staphylococcus aureus* responsible for documented infections in European hospitals. Clinical Microbiology and Infection. 2012; 18: 536-537.

Mezzatesta M.L. et al., In vitro evaluation of daptomycin in combination with other drugs against difficult to treat *Staphylococci* and *Enterococci*. Clinical Microbiology and Infection. 2012; 18: 437.

Mihailescu R. et al., High efficacy of fosfomycin-rifampin combination against methicillin-resistant *Staphylococcus aureus* in an experimental model of foreign-body infection. Clinical Microbiology and Infection. 2012; 18: 596.

Miller M, Fidaxomicin (OPT-80) for the treatment of *Clostridium difficile* infection. Expert Opin Pharmacother. Jun. 2010; 11(9): 1569-78.

Morreale C.A. et al., The relationship between inpatient fluoroquinolone use and *Clostridium difficile*-associated diarrhea. Annals of Pharmacotherapy. 2010; 44(5): 826-831.

Morrissey I. et al., Activity of oritavancin against recent clinical isolates of methicillin-resistant *Staphylococci* from Western Europe. Clinical Microbiology and Infection. 2012; 18: 536.

Mullane KM et al., Fidaxomicin: first-in-class macrocyclic antibiotic. Expert Rev Anti Infect Ther. Jul. 2011; 9(7): 767-77.

Munita J.M. et al., Is daptomycin susceptibility breakpoint appropriate for *Enterococci*? Clinical Microbiology and Infection. 2012; 18: 735.

Musher DM et al., Nitazoxanide for the treatment of *Clostridium difficile* colitis. Clin Infect Dis. Aug. 15, 2006; 43(4): 421-7. Epub Jul. 11, 2006.

Nathwani D. et al., Pan-European study of real-world treatment patterns and early switch/early discharge opportunities in patients with complicated skin and soft tissue infections due to meticillin-resistant *Staphylococcus aureus*: Study methodology and interim results. Clinical Microbiology and Infection. 2012; 18: 711.

Nelson R., Antibiotic treatment for *Clostridium difficile*-associated diarrhea in adults. Cochrane Database Syst Rev. 2007; (3): CD004610.

Ng J et al., *Clostridium difficile* toxin-induced inflammation and intestinal injury are mediated by the inflammasome. Gastroenterology. Aug. 2010; 139(2): 542-52 552. e1-3. Epub Apr. 13, 2010.

Nikolaidis P. et al., Results from an observational study: Daptomycin is effective in the treatment of catheter-related bacteraemia. Clinical Microbiology and Infection. 2012; 18: 770-771.

No Authors, Hospital Medicine and Infectious Diseases; 2005; 9(2): 4-60.

Nomura K et al., Absence of pseudomembranes in *Clostridium difficile*-associated diarrhea in patients using immunosuppression agents. Scand J Gastroenterol. 2009; 44(1): 74-8.

Odenholt I et al., Pharmacodynamic studies of vancomycin metronidazole and fusidic acid against *Clostridium difficile*. Chemotherapy. 2007; 53(4): 267-74. Epub Jun. 25, 2007.

Oguz F et al., The role of *Clostridium difficile* in childhood nosocomial diarrhea. Scand J Infect Dis. 2001; 33(10): 731-3.

Ohl CA et al., Antimicrobial stewardship for inpatient facilities. J Hosp Med. Jan. 2011; 6(S1): S4-S15. doi: 10.1002/jhm.881.

Okumu F et al., Safety and pharmacokinetics of OPT-80 a novel antibiotic for treatment of *Clostridium difficile* associated diarrhea (CDAD). 44th Intersci Conf Antimicrob Agents Chemother (ICAAC) Oct. 30-Nov. 2 Washington DC. 2004; Abst F-726.

Ota K et al., Molecular epidemiology of quinolone-resistant *Neisseria gonorrhoeae* in Ontario Canada. Canadian Journal of Infectious Diseases & Medical Microbiology. 2010; 21: 37A.

Otto M.P. et al., Effect of antibiotics on virulence expression by community-acquired methicillin-resistant *Staphylococcus aureus*. Clinical Microbiology and Infection. 2012; 18: 633.

Owens RC, *Clostridium difficile*-associated disease: an emerging threat to patient safety: insights from the Society of Infectious Diseases Pharmacists. Pharmacotherapy. Mar. 2006; 26(3): 299-311.

Owens, Robert C. et al., Impact of Interventions on Non-Evidence Based Treatment Strategies (NETS) During an Outbreak of *Clostridium difficile*-Associated Disease (CDAD) Due to BI/NAP1. Oral Session presented at IDSA 2006; 0(0): 0.

Owens RC Jr et al., Antimicrobial-associated risk factors for *Clostridium difficile* infection. Clin Infect Dis. Jan. 15, 2008; 46 Suppl 1: S19-31.

Partridge DG et al., Outpatient parenteral antibiotic therapy for infective endocarditis: a review of 4 years' experience at a UK centre. Postgrad Med J. Jul. 2012; 88(1041): 377-81. Epub Feb. 25, 2012.

Patino H et al., Efficacy and Safety of the Lipopeptide CB-183 315 for the Treatment of *Clostridum difficile* infection. 51st Interscience Conference on Antmicrobial Agents and Chemotherapy; ICAAC; Sep. 17-20, 2011; Chicago IL K-205a.

Pena-Monje a. et al., In vitro activities of fosfomicin and gentamicin combinations against clinical isolates of *Staphylococcus aureus*. Clinical Microbiology and Infection. 2012; 18: 438.

Pepin J et al., Increasing risk of relapse after treatment of *Clostridium difficile* colitis in Quebec Canada. Clin Infect Dis. Jun. 1, 2005; 40(11): 1591-7. Epub Apr. 25, 2005.

Pepin J et al., Management and outcomes of a first recurrence of *Clostridium difficil*-associated disease in Quebec Canada. Clin Infect Dis. Mar. 15, 2006; 42(6): 758-64. Epub Feb. 7, 2006.

Perri M. et al., In vitro susceptibility trends for MSSA bloodstream isolates over a 3.5 year period in Detroit. Clinical Microbiology and Infection. 2012; 18: 754-755.

Pillar CM et al., Activity Profile of CB-183 315 against *S. aureus* Including Enterotoxin Expressing Isolates Tested Anaerobically. ICCAC Sep. 12-15, 2010; Boston MA [Poster #:] 1972.

Pinto L.J. et al., Incidence and importance of *Clostridium difficile* in paediatric diarrhoea in Brazil. J Med Microbiol. Dec. 2003; 52(Pt 12): 1095-9.

Pituch H, *Clostridium difficile* is no longer just a nosocomial infection or an infection of adults. Int J Antimicrob Agents. Mar. 2009; 33 Suppl 1: S42-5.

Polgreen P.M. et al., An outbreak of severe *Clostridium difficile*-associated disease possibly related to inappropriate antimicrobial therapy for community-acquired pneumonia. Infect Control Hosp Epidemiol. Feb. 2007; 28(2): 212-4. Epub Jan. 25, 2007.

Prantera C et al., Antibiotics and probiotics in inflammatory bowel disease: why when and how. Curr Opin Gastroenterol. Jul. 2009; 25(4): 329-33.

Razaq N et al., Infection of hamsters with historical and epidemic BI types of *Clostridium difficile*. J Infect Dis. Dec. 15, 2007; 196(12): 1813-9.

Redelings M.D. et al., Increase in *Clostridium difficile*-related mortality rates United States 1999-2004. Emerg Infect Dis. Sep. 2007; 13(9): 1417-9.

Rege S et al., Risk Factors for *Clostridium Difficile* Infection Recurrence: Comparison of CB-183 315 and Oral Vancomycin. Eccmid. Mar. 31-Apr. 3, 2012; London England P2251.

Rexach CE et al., Epidemiologic surveillance of *Clostridium difficile* diarrhea in a freestanding pediatric hospital and a pediatric hospital at a university medical center. Diagn Microbiol Infect Dis. Oct. 2006; 56(2): 109-14. Epub May 4, 2006.

Riddle DJ et al., *Clostridium difficile* infection in solid organ transplant recipients. Curr Opin Organ Transplant. Dec. 2008; 13(6): 592-600.

Rodemann JF et al., Incidence of *Clostridium difficile* infection in inflammatory bowel disease. Clin Gastroenterol Hepatol. Mar. 2007; 5(3): 339-44.

Rodney JR et al., Difficulties with *Clostridium difficile*. Surg Infect (Larchmt). Dec. 2007; 8(6): 553-6.

Rolston K. et al., *Staphylococcus aureus* susceptibility to vancomycin and alternative agents at a comprehensive cancer centre. Clinical Microbiology and Infection. 2012; 18: 416-417.

Rouphael NG et al., *Clostridium difficile*-associated diarrhea: an emerging threat to pregnant women. Am J Obstet Gynecol. Jun. 2008; 198(6): 635 .e1-6. Epub Apr. 8, 2008.

Ryder NS, Discontinued drugs in 2008: anti-infectives. Expert Opin Investig Drugs. Jan. 2010; 19(1): 1-21.

Sader H. et al., Activity of the novel antimicrobial ceftolozane/tazobactam (CXA-201) tested against contemporary clinical strains from European hospitals. Clinical Microbiology and Infection. 2012; 18: 382.

Sader H. et al., Antimicrobial activity of PTK 0796 (omadacycline) tested against Gram-positive organisms isolated from European hospitals in 2011. Clinical Microbiology and Infection. 2012; 18: 384.

Sader H. et al, Update on daptomycin activity and spectrum tested against Gram-positive organisms collected in 2011 from European medical centres. Clinical Microbiology and Infection. 2012; 18: 540.

Sader H. et al Antimicrobial susceptibility and species identification of *Corynebacterium spp.* strains collected in Europe and USA medical centres 2006-2010. Clinical Microbiology and Infection. 2012; 18: 261.

Sahm D.F. et al., Dalbavancin maintains potent in vitro activity against *S. aureus* resistant to currently utilised anti-MRSA therapeutics. Clinical Microbiology and Infection. 2012; 18: 539.

Scheinfeld N. et al., Tolevamer an orally administered toxin-binding polymer for *Clostridium difficile*-associated diarrhea. Curr Opin Investig Drugs. Aug. 2008; 9(8): 913-24.

Seo da H et al., More bad news on *Clostridium difficile* in inflammatory bowel disease. Inflamm Bowel Dis. Apr. 2009; 15(4): 641-2.

Sethi A.K. et al., Skin and environmental contamination with vancomycin-resistant *Enterococci* in patients receiving oral metronidazole or oral vancomycin treatment for *Clostridium difficile*-associated disease. Infect Control Hosp Epidemiol. Jan. 2009; 30(1): 13-7.

Shangle S. et al., Safety and pharmacokinetics of OPT-80 in human volunteers. 44th Intersci Conf Antimicrob Agents Chemother (ICAAC) (Oct. 30-Nov. 2 Washington DC). 2004; Abst A-5.

Shue Y.K. et al., Safety tolerance and pharmacokinetic studies of OPT-80 in healthy volunteers following single and multiple oral doses. Antimicrob Agents Chemother. Apr. 2008; 52(4): 1391-5. Epub Feb. 11, 2008.

Smith LC et al., *Clostridium difficile* hospitalizations in Louisiana: a 10 year review. J La State Med Soc. Jul.-Aug. 2011; 163(4): 192-5.

Snydman D.R. et al., Activity of ceftolozane/tazobactam (CXA-201) against 270 recent isolates from the Bacteroides group. Clinical Microbiology and Infection. 2012; 18: 382.

Snydman D.R. et al., Activity of a novel cyclic lipopeptide CB-183 315 against Gram-positive aerobic and anaerobic enteric isolates including vancomycin-resistant enterococci and *C. difficile* strains with elevated MICs to metronidazole vancomycin and fluoroquinolones. Clinical Microbiology and Infection 2011 17 Suppl. 4 (S300).

Spiliopoulou I. et al., Activity of vancomycin linezolid and daptomycin against *Staphylococci* and *Enterococci* isolated in Greek hospitals 2008-2010. Clinical Microbiology and Infection. 2012; 18: 305.

Stein GE, Safety of newer parenteral antibiotics. Clin Infect Dis. Sep. 1, 2005; 41 Suppl 5: S293-302.

Stepan C et al., Treatment strategies for recurrent and refractory *Clostridium difficile*-associated diarrhea. Expert Rev Gastroenterol Hepatol. Dec. 2007; 1(2): 295-305.

Stevens D.L. et al., Successful treatment of *Staphylococcal* toxic shock syndrome with linezolid: a case report and in vitro evaluation of the production of toxic shock syndrome toxin type 1 in the presence of antibiotics. Clin Infect Dis. Mar. 1, 2006; 42(5): 729-30.

Stundick M.V. et al., State-of-the-art therapeutic medical countermeasures for bacterial threat agents. Drug Development Research. 2011; 72: 361-378.

Stylianakis A. et al., A 4-year study of coagulase-negative *Staphylococcus* resistance profile in a Greek tertiary hospital. Clinical Microbiology and Infection. 2012; 18: 344-345.

Sun X et al., Chapter 16 recent development treatment *Clostridium difficile* associated disease (cdad). Annual Reports in Medicinal Chemistry. 2008; 43(43): 269.

Sunderland J. et al., Therapeutic drug monitoring of daptomycin: A 4-year audit of levels from a UK clinical antibiotic service. Clinical Microbiology and Infection. 2012; 18: 445.

Surawicz C.M. et al., Treatment of refractory and recurrent *Clostridium difficile* infection. Nature Reviews Gastroenterology and Hepatology. 2011; 8(6): 330-339.

Surowiec D. et al., Past present and future therapies for *Clostridium difficile*-associated disease. Annals of Pharmacotherapy. 2006; 40(12): 2155-2163.

Taglietti F. et al., Telavancin and daptomicin activity against methicillin resistant *Staphylococcus aureus* strains after vancomycin resistance selection in vitro. Clinical Microbiology and Infection. 2012; 18: 538.

Thomas K.L. et al., A Cost Comparison of Metronidazole and Vancomycin in the Treatment of *Clostridium Difficile* Associated Diarrhea; Abstract 417.

Trezza C et al., An Evaluation of the Combination of Daptomycin and Rifampin against vancomycin-resistant *Enterococci* isolated from the bloodstream of neutropenic patients. Pharmacotherapy. 2012; 32(10): PE291-292.

Utili R. et al., Safety of high-dose long-term daptomycin treatment (>=8 mg/kg/day over more than 2 or 4 weeks) in the European Cubicin(r) Outcome Registry and Experience (EU-CORE). Clinical Microbiology and Infection. 2012; 18: 523.

Van Der Donk C. et al., Antimicrobial resistance of *Staphylococcus aureus* isolates from primary care patients and nursing home residents in the Netherlands and Germany. Clinical Microbiology and Infection. 2012; 18: 417.

Van Nispen Tot et al., Recurrent *Clostridium difficile* Infection: What are the Treatment Options? Drugs. May 7, 2011; 71(7): 853-68.

Vesta K.S. et al., Specific risk factors for *Clostridium difficile*-associated diarrhea: a prospective multicenter case control evaluation. Am J Infect Control. Oct. 2005; 33(8): 469-72.

Vivas M. et al., Experimental study of the efficacy of daptomycin in the therapy of high cephalosporin-resistant pneumococcal meningitis. Clinical Microbiology and Infection. 2012; 18: 596.

Walker K, Interscience Conference on Antimicrobial Agents and Chemotherapy—50th Annual Meeting—Research on Promising New Agents: Part 1. IDrugs. Nov. 2010; 13(11): 743-5.

Warny M et al., Toxin production by an emerging strain of *Clostridium difficile* associated with outbreaks of severe disease in North America and Europe. Lancet. Sep. 24-30, 2005; 366(9491): 1079-84.

Willey B.M. et al., Evaluation of Vitek 2 AST-P612 card for daptomycin susceptibility testing of *Staphylococcus aureus* and coagulase-negative staphylococci. Clinical Microbiology and Infection. 2012; 18: 456.

Willey B.M. et al., Snapshot of an inner-city emergency room (ER): Surveillance of patients staff and stethoscopes for community-acquired methicillin-resistant *Staphylococcus aureus* (CA-MRSA). Canadian Journal of Infectious Diseases & Medical Microbiology. 2010; 21: 36A.

Yapar N. et al., Nosocomial outbreak of *Corynebacterium striatum* infection in a surgical intensive care unit. Clinical Microbiology and Infection. 2012; 18: 640.

Yin N. et al., Structure Activity Relationship Studies of Aromatic Tail Containing Lipopeptides Leading to CB-183 315 a Novel Cyclic Lipopeptide Being Developed for the Treatment of *Clostridium difficile* Infection. ICCAC Sep. 12-15, 2010; Boston MA F1-1612.

Yin N. et al., In Vitro and in Vivo Studies of a Series of Aliphatic Tail-Containing Semi-Synthetic Lipopeptides Against *Clostridium difficile*. ICCAC Sep. 12-15, 2010; Boston MA F1-1618.

Yousuf K et al., *Clostridium difficile*—Associated diarrhea and chronic renal insufficiency. Southern Medical Journal. 2002; 95(7): 681-683.

Zerey M et al., The burden of *Clostridium difficile* in surgical patients in the United States. Surg Infect (Larchmt). Dec. 2007; 8(6): 557-66.

Zilberberg M.D. et al., Epidemiology and outcomes of *Clostridium difficile*-associated disease among patients on prolonged acute mechanical ventilation. Chest. 2009; 136(3): 752-758.

Zilberberg M.D. et al., Increase in adult *Clostridium difficile*-related hospitalizations and case-fatality rate United States 2000-2005. Emerg Infect Dis. 2008; 14(6): 929-931.

Zilberberg M.D. et al., Growth and geographic variation in hospitalizations with resistant infections United States 2000-2005. Emerg Infect Dis. 2008; 14(11): 1756-1758.

Zilberberg M.D. et al., Increase in *Clostridium difficile*-related hospitalizations among infants in the United States 2000-2005. Pediatr Infect Dis J. 2008; 27(12): 1111-1113.

Zilberberg MD et al., Growth in the incidence of hospitalizations with resistant infections in elderly people in the United States: 2000 to 2006. J Am Geriatr Soc. Dec. 2008; 56(12): 2356-8.

Zilberberg MD et al., Using Electronic Health Information to Risk-Stratify Rates of *Clostridium difficile* Infection in US Hospitals. Infect Control Hosp Epidemiol. Jul. 2011; 32(7): 649-55.

Poster Sessions Clinical Microbiology and Infection. 2012; 18: 114-715.

Abstracts of the British Society of Gastroenterology Annual General Meeting. Mar. 23-26, 2009. Glasgow Scotland. Gut. Apr. 2009; 58 Suppl 1: A1-156.

Alborn, W.E. Jr. et al., "Daptomycin Disrupts Membrane Potential in Growing *Staphylococcus aureus*," Antimicrobial Agents and Chemotherapy 35: 2282-2287 (1991).

Allen, N.E. et al. "Inhibition of Peptidoglycan Biosynthesis in Gram-Positive Bacteria by LY146032," Antimicrobial Agents and Chemotherapy 31: 1093-1099 (1987).

Allen, N.E. et al. "Inhibition of Membrane Potential-Dependent Amino Acid Transport by Daptomycin," Antimicrobial Agents and Chemotherapy 35: 2639-2642 (1991).

Baltz, R.H., "Lipopeptide Anibiotics Produced by *Streptomyces reseosporus* and *Streptomyces fradiae*," in Biotechnology of Antibiotics, 2d Ed., 415-435 (1997).

Bingen, E. et al. "Bactericidal Activity of Daptomycin Against Vancomycin-Resistant *Enterococcus faecium* in an in Vitro Pharmacokinetic Model," Eur. J. Clin. Microbiol. Infect. Dis. 10: 1062-1065 (1991).

Boeck, LaVerne D. et al., "Deacylation of A21978C, an Acidic Lipopeptide Antibiotic Complex, by *Actinoplanes utahensis*," Journal of Antibiotics XLI: 1085-1092 (1988).

Boeck, L. D. et al. "A54145, A New Lipopeptide Antibiotic Complex: Discovery, Taxonomy, Fermentation and HPLC," Journal of Antibiotics XLIII: 587-593 (1990).

Champlin, Franklin R. et al. "Cell Envelope Impermeability to Daptomycin in *Pseudomonas aeruginosa* and *Pasteurella multocida*," Current Microbiology 21: 367-372 (1990).

Chong, Pei Pei et al. "Physical Identification of a Chromosomal Locus Encoding Biosynthetic Genes for the Lipopeptide Calcium-Dependent Antibiotic (CDA) of *Streptomyces coelicolor* A3(2)," Microbiology 144: 193-199 (1998).

Clinical and Laboratory Standards Institute. Methods for Dilution Antimicrobial Susceptibility Tests for Bacteria That Grow Aerobically; Approved Standard—Seventh Edition. Clinical and Laboratory Standards Institute document M7-A7; ISBN 1-56238-587-9; (2006).

Debono, M. et al. "A21978C, A Complex of New Acidic Peptide Antibiotics: Isolation, Chemistry, and Mass Spectral Structure Elucidation," Journal of Antibiotics XL: 761-777 (1987).

Debono, M. et al. "Enzymatic and Chemical Modifications of Lipopeptide Antibiotic A21978C: The Synthesis and Evaluation of Daptomycin (LY146032)," Journal of Antibiotics XLI: 1093-1105 (1988).

Debono, M. et al. "Synthesis of New Analogs of Echinocandin B by Enzymatic Deacylation and Chemical Reacylation of the Echinocandin B Peptide: Synthesis of the Antifungal Agent Cilofungin (LY121 019)," Journal of Antibiotics XLII: 389-397 (1989).

Dong, Mei-Yan et al. "Treatment of *Clostridium difficile* Colitis in Hamsters with a Lipopeptide Antibiotic, LY146032," Antimicrobial Agents and Chemotherapy 31: 1135-1136 (1987).

Eid, Pascale et al. "Effect of Daptomycin on the Barotropic Behavior of Dioleoylphosphatidylglycerol: An Infrared Spectroscopic Investigation," Chemistry and Physics of Lipids 83: 131-140 (1996).

Eliopoulos, George M. et al. "In Vitro Activity and Mechanism of Action of A21978C1, a Novel Cyclic Lipopeptide Antibiotic," Antimicrobial Agents and Chemotherapy 27: 357-362 (1985).

Fostel, J.M. et al. "Emerging novel antifungal agents" *Drug Discovery Today* 5(1):25-32 (2000).

Gennaro, Alfonso R., Editor, *Remington's Pharmaceutical Sciences*, Chapter 64, 17$^{th}$ edition, 1176-1213 (1985).

Huber, F. M. et al. The Formation of Daptomycin by Supplying Decanoic Acid to *Streptomyces roseosporus* Cultures Producing the Antibiotic Complex A21978C, Journal of Biotechnology 7: 283-292 (1988).

Huber, F. M. et al. "The Synthesis of A21978C Analogs by *Streptomyces roseosporus* Cultivated Under Carbon Limitation and Fed Fatty Acids," Biotechnology Letters 12: 789-792 (1990).

Inokoshi, Junji et al. "Cloning and Sequencing of the Aculeacin A Acylase-Encoding Gene From *Actinoplanes utahensis* and Expression in *Streptomyces lividans*," Gene 119: 29-35 (1992).

Inokoshi, Junji et al. "Efficient Production of Aculeacin A Acylase in Recombinant *Streptomyces* strains," Appl. Microbiol. Biotechnol. 39: 532-536 (1993).

International Preliminary Report on Patentability for International Application No. PCT/US2009/068747, mailed Feb. 4, 2011.

International Search Report and Written Opinion for International Application No. PCT/US2009/068747, mailed Mar. 16, 2010.

Kempter, Christoph et al. "CDA: Calcium-Dependent Peptide Antibiotics from *Streptomyces coelicolor* A3(2) Containing Unusual Residues," Angew. Chem. Int. Ed. Engl. 36: 498-501 (1997).

Kirsch, Lee E. et al. "Kinetics of the Aspartyl Transpeptidation of Daptomycin, a Novel Lipopeptide Antibiotic," Pharmaceutical Research 6: 387-393 (1989).

Lakey, Jeremy H. et al. "The Role of Acyl Chain Character and Other Determinants on the Bilayer Activity of A21978C an Acidic Lipopeptide Antibiotic," Biochimica et Biophysica Acta 859: 219-226 (1986).

Lakey, Jeremy H. et al. "Fluorescence Indicates a Calcium-Dependent Interaction Between the Lipopeptide Antibiotic LY146032 and Phospholipid Membranes," Biochemistry 27: 4639-4645 (1988).

Lakey, Jeremy H. et al. The Lipopeptide Antibiotic A21978C Has a Specific Interaction With DMPC Only in the Presence of Calcium Ions, Biochimica et Biophysica Acta 985: 60-66 (1989).

Lee, Belle L. et al. "Effect of Protein Binding of Daptomycin on MIC and Antibacterial Activity," Antimicrobial Agents and Chemotherapy 35: 2505-2508 (1991).

Liebowitz, Lynne D. et al. "In Vitro Selection of Bacteria Resistant to LY146032, a New Cyclic Lipopeptide," Antimicrobial Agents and Chemotherapy 32: 24-26 (1988).

Maget-Dana, Regine et al. "A Comparative Monomolecular Film Study of Antibiotic A21978C Homologues of Various Lipid Chain Length," Biochimica et Biophysica Acta 962: 201-207 (1988).

Tally, F.P. et al. "Daptomycin: a novel agent for Gram-positive infections" *Exp. Opin. Invest. Drugs* 8(8):1223-1238 (1999).

Vallinayagam, R. et al. "Synthesis of Novel and Stable 5-Aminolevulinic Acid Derivatives for the Efficient Synthesis of 5-Aminolevulinic Acid Based Prodrugs" *Synthesis* 23:3731-3735 (2007).

Zambias, Robert A. et al. "Preparation and Structure-Activity Relationships of Simplified Analogues of the Antifungal Agent Cilofungin: A Total Synthesis Approach," Journal of Medicinal Chemistry 35: 2843-2855 (1992).

Zmijewski, M.J. et al. "Role of Branched Chain Fatty Acid Precursors in Regulating Factor Profile in the Biosynthesis of A21978 C Complex," Journal of Antibiotics XXXIX: 1483-1485 (1986).

Lu, J. et al. "Molecular typing and phenotype characterisation of methicillin-resistant *Staphylococcus aureus* Isolates from blood in Taiwan," Clinical Microbiology and Infection. 2012; 18: 336-337.

Gerding, D.N. et al. "Management of *Clostridium difficile* infection: Thinking inside and outside the box," Clinical Infectious Diseases. 2010; 51(11): 1306-1313.

Prous, J.R., "Annual Updated 2003/2004—Treatment of Gastrointestinal Disorders", Drugs of the Future 2004, 29(5): 493-556 (2004).

National Library of Medicine, "Medical Letter on Drugs and Therapeutics", v. 50, No. 1300, Dec. 1, 2008.

Badger, Victor O. et al., "*Clostridium difficile*: Epidemiology, Pathogenesis, Management and Prevention of a Recalcitrant Healthcare-Associated Pathogen", Journal of Parenteral and Enteral Nutrition, vol. 36, No. 6, Nov. 2012.

Barbut F. et al., "Epidemiology of *Clostridium difficile*-associated infections", European Society of Clinical Microbiology and Infectious Diseases, Clin. Microbiol Infect 2001; 7:405-410.

Fishman, Neil, "Antimicrobial stewardship", Infect Control 2006; 34:S55-63.

ANTIBACTERIAL AGENTS FOR THE TREATMENT OF GRAM POSITIVE INFECTIONS

This application claims the benefit of U.S. Provisional patent application 61/139,875, filed Dec. 22, 2008, incorporated herein by reference in its entirety.

The present invention relates to novel lipopeptide compounds. The invention also relates to pharmaceutical compositions of these compounds and methods of using these compounds as antibacterial agents. The invention also relates to methods of producing these novel lipopeptide compounds and intermediates used in producing these compounds, as well as compositions using the same.

The rapid increase in the incidence of gram-positive infections, including those caused by resistant bacteria, has sparked renewed interest in the development of novel classes of antibiotics. A class of compounds which have shown potential as useful antibiotics includes the A-21978C lipopeptides described in, for example, U.S. Pat. Nos. RE 32,333; RE 32,455; RE 32,311; RE 32,310; 4,482,487; 4,537,717; 6,911,525; 7,335,725; 7,408,025; 6,794,490; 7,262,268; 7,335,726; and RE 39,071. Daptomycin, a member of this class, has potent bactericidal activity in vitro and in vivo against clinically relevant gram-positive bacteria that cause serious and life-threatening diseases. These bacteria include resistant pathogens, such as vancomycin-resistant enterococci (VRE), methicillin-resistant *Staphylococcus aureus* (MRSA), glycopeptide intermediate susceptible *Staphylococcus aureus* (GISA), coagulase-negative staphylococci (CNS), and penicillin-resistant *Streptococcus pneumoniae* (PRSP), for which there are few therapeutic alternatives. See, e.g., Tally et al., 1999, *Exp. Opin. Invest. Drugs* 8:1223-1238.

Despite the promise that antibacterial agents such as daptomycin offer, the need for novel antibiotics continues. Many pathogens have been repeatedly exposed to commonly-used antibiotics. This exposure has led to the selection of variant antibacterial strains resistant to a broad spectrum of antibiotics. The loss of potency and effectiveness of an antibiotic caused by resistant mechanisms renders the antibiotic ineffective and consequently can lead to life-threatening infections that are virtually untreatable. As new antibiotics come to market pathogens may develop resistance or intermediate resistance to these new drugs, effectively creating a need for a stream of new antibacterial agents to combat these emerging strains. In addition compounds that exhibit bacteriacidal activity would offer advantages over present bacteriastatic compounds. Thus, novel synthetic antibacterial agents would be expected to be useful to treat not only "natural" pathogens, but also intermediate drug resistant and drug resistant pathogens because the pathogen has never been exposed to the novel antibacterial agent. Additionally, new antibacterial agents may exhibit differential effectiveness against different types of pathogens.

One pathogen of particular concern is *Clostridium difficile*. *C. difficile* has become a huge public health concern, and in recent years has become the most common cause of nosocomial infectious diarrhea. Current *Clostridium difficile*-associated disease treatment options are often suboptimal, with treatment failure and a high incidence of relapse in some patients. In addition, new highly virulent strains of *C. difficile* are continually developing. One new epidemic strain (PFGE type BI/NAP1, also called Nap1, ribotype 027 or NAP1/027) appears to be more virulent than many other strains. As the incidence of *Clostridium difficile*-associated disease continues to increase and highly virulent strains develop, new antibacterial agents to treat or prevent this disease are needed.

The present invention addresses this problem by providing novel lipopeptide compounds which have antibacterial activity against a broad spectrum of bacteria, including drug-resistant bacteria and *C. difficile*. Further, the compounds of the present invention exhibit bacteriacidal activity.

The present invention comprises, in one aspect, antibacterial compounds of Formula (I):

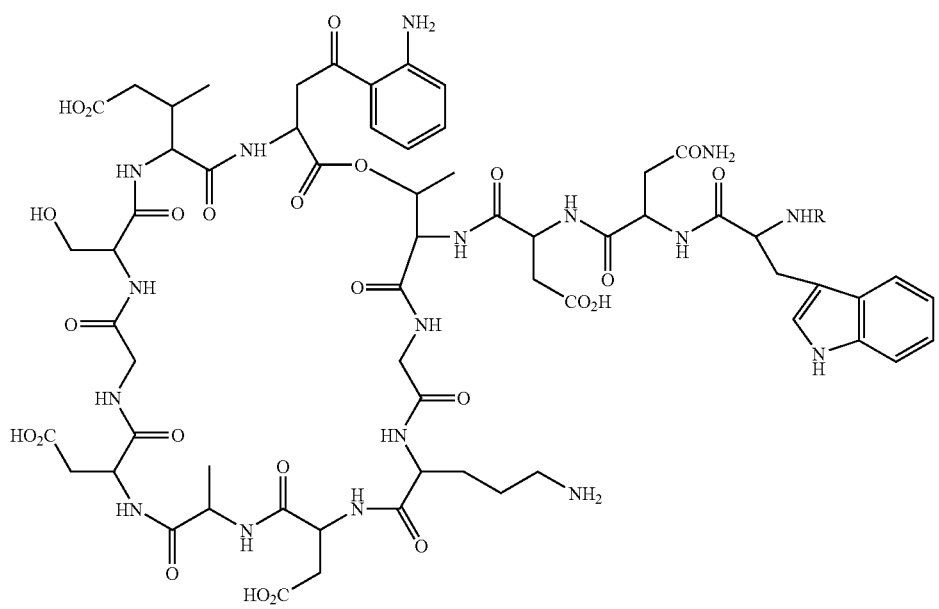

(I)

and pharmaceutically acceptable salts thereof, wherein:
R is:

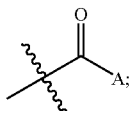

and
A is chosen from alkyl, alkenyl, cycloalkyl, aryl, heteroaryl, and NHR$^A$,
wherein R$^A$ is chosen from alkyl and cycloalkyl.

In another embodiment, the invention also provides pharmaceutical compositions comprising compounds of Formula I and methods of use thereof.

In a further embodiment, the invention provides methods of making compounds of Formula I and pharmaceutical compositions thereof.

In a still further embodiment, the invention provides methods of use of the compounds of Formula I to treat bacterial infections in humans.

It is to be understood that both the foregoing general description and the following detailed description are exemplary and explanatory only and are not restrictive of the invention, as claimed.

Molecular terms, when used in this application, have their common meaning unless otherwise specified.

The term "acyl" is defined as a carbonyl radical attached to an alkyl, alkenyl, alkynyl, cycloalkyl, heterocycyl, aryl or heteroaryl group, examples including, without limitation, such radicals as acetyl and benzoyl.

The term "amino" denotes a nitrogen radical containing two substituents independently selected from the group consisting of H, alkyl, cycloalkyl, carboalkoxy, heterocyclyl, aryl, heteroaryl and sulfonyl. Subsets of the term "amino" are (1) the term "unsubstituted amino" which denotes an NH$_2$ radical, (2) the term "mono substituted amino" which is defined as a nitrogen radical containing a hydrogen atom and a substituent group selected from alkyl, cycloalkyl, heterocyclyl, aryl, or heteroaryl, and (3) the term "disubstituted amino" which is defined as a nitrogen radical containing two substituent groups independently selected from, alkyl, cycloalkyl, heterocyclyl, aryl, and heteroaryl. Exemplary mono substituted amino radicals are "lower mono substituted amino" radicals, whereby the substituent group is a lower alkyl group. Exemplary disubstituted amino radicals are "lower disubstituted amino" radicals, whereby the substituent groups are lower alkyl.

The term "acyloxy" denotes an oxygen radical adjacent to an acyl group.

The term "acylamino" denotes a nitrogen radical adjacent to an acyl group.

The term "carboalkoxy" is defined as a carbonyl radical adjacent to an alkoxy or aryloxy group.

The term "carboxyamido" denotes a carbonyl radical adjacent to an amino group.

The term "halo" is defined as a bromo, chloro, fluoro or iodo radical.

The term "thio" denotes a divalent sulfur radical containing a substituent group independently selected from H, alkyl, cycloalkyl, heterocyclyl, aryl and heteroaryl. Examples include methylthio and phenylthio.

The term "alkyl" is defined as a linear or branched, saturated radical having one to about twenty carbon atoms unless otherwise specified. Exemplary alkyl radicals include $C_1$-$C_{12}$, $C_1$-$C_8$, $C_1$-$C_6$, and $C_4$-$C_6$ alkyl groups. One or more hydrogen atoms can also be replaced by a substitutent group selected from acyl, amino, acylamino, acyloxy, carboalkoxy, carboxy, carboxyamido, cyano, halo, hydroxyl, nitro, thio, alkenyl, alkynyl, cycloalkyl, heterocyclyl, aryl, heteroaryl, alkoxy, aryloxy, sulfinyl, sulfonyl, oxo, guanidino, formyl and an amino acid side chain. Examples of alkyl groups include, without limitation, methyl, tert-butyl, isopropyl, and methoxymethyl. Subsets of the term "alkyl" are (1) "unsubstituted alkyl" which is defined as an alkyl group that bears no substituent groups (2) "substituted alkyl" which denotes an alkyl radical in which (a) one or more hydrogen atoms is replaced by a substitutent group selected from acyl, acyloxy, carboalkoxy, carboxy, carboxyamido, cyano, nitro, thio, alkenyl, alkynyl, cycloalkyl, heterocyclyl, aryl, heteroaryl, alkoxy, aryloxy, sulfinyl, sulfonyl, N-sulfonylcarboxyamido, N-acylaminosulfonyl or (b) two or more hydrogen atoms are each replaced by a substituent group independently selected from hydroxyl, carboxy, $C_1$-$C_3$ alkoxy, amino, acylamino, oxo or guanidino; and (3) the term "selected substituted alkyl" which denotes an alkyl radical in which (a) one proton is replaced by a group selected from hydroxyl, carboxy $C_1$-$C_3$ alkoxy, unsubstituted amino, acylamino, or acylamino phenyl or (b) one to three protons is replaced by a halo substituent.

An alkyl can also be "interrupted" by at least one "interrupting functional groups" selected from aryl, cycloalkyl, heterocycloalkyl, O, S, and N. As used herein, the phrase "interrupted" means that an internal methylene unit is replaced by at least one of the functional groups as defined above. Examples of alkyl chains that have been "interrupted" with O include —CH$_2$OCH$_2$—, —CH$_2$O(CH$_2$)$_2$—, —CH$_2$O (CH$_2$)$_3$—, —CH$_2$O(CH$_2$)$_4$—, —(CH$_2$)$_2$OCH$_2$, —(CH$_2$)$_2$O (CH$_2$)$_2$—, —(CH$_2$)$_2$O(CH$_2$)$_3$—, —(CH$_2$)$_3$O(CH$_2$)—, —(CH$_2$)$_3$O(CH$_2$)$_2$—, and —(CH$_2$)$_4$O(CH$_2$)—. Other examples of alkylene chains that are "interrupted" with functional groups include —CH$_2$ZCH$_2$—, —CH$_2$Z(CH$_2$)$_2$—, —CH$_2$Z(CH$_2$)$_3$—, —CH$_2$Z(CH$_2$)$_4$—, —(CH$_2$)$_2$ZCH$_2$—, —(CH$_2$)$_2$Z(CH$_2$)$_2$—, —(CH$_2$)$_2$Z(CH$_2$)$_3$—, —(CH$_2$)$_3$Z (CH$_2$)—, —(CH$_2$)$_3$Z(CH$_2$)$_2$—, and —(CH$_2$)$_4$Z(CH$_2$)—, wherein Z is one of the "interrupting functional groups" listed above.

The term "alkenyl" is defined as linear or branched radicals having two to about twenty carbon atoms, such as three to about ten carbon atoms, and containing at least one carbon-carbon double bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. The double bond portion(s) of the unsaturated hydrocarbon chain may be either in the cis or trans configuration. Examples of alkenyl groups include, without limitation, ethylenyl or phenyl ethylenyl.

The term "alkynyl" denotes linear or branched radicals having from two to about ten carbon atoms, and containing at least one carbon-carbon triple bond. One or more hydrogen atoms can also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, formyl, oxo and guanidino. An example of alkynyl group includes, without limitation, propynyl.

"Alkyl," "alkenyl," and "alkynyl" can also be "interrupted" by at least one group selected from aryl, cycloalkyl, heterocycloalkyl, O, S, and N.

The term "aryl" or "aryl ring" denotes aromatic radicals in a single or fused carbocyclic ring system, having from five to fourteen ring members. In one embodiment, the ring system has from six to ten ring members. One or more hydrogen atoms may also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of aryl groups include, without limitation, phenyl, naphthyl, biphenyl, terphenyl. Subsets of the term aryl are (1) the term "phenyl" which denotes a compound of the formula:

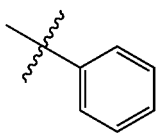

(2) the term "substituted phenyl" which is defined as a phenyl radical in which one or more hydrogen atoms are replaced by a substituent group selected from acyl, amino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino phenyl" denotes a phenyl radical in which one hydrogen atom is replaced by an acylamino group. One or more additional hydrogen atoms can also be replaced by a substituent group selected from acyl, amino, acylamino, acyloxy, azido, alkylthio, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

"Heteroaryl" or "heteroaryl ring" denotes an aromatic radical which contain one to four hetero atoms or hetero groups selected from O, N, S,

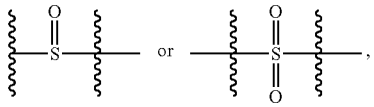

in a single or fused heterocyclic ring system, having from five to fifteen ring members. In one embodiment, the heteroaryl ring system has from six to ten ring members. One or more hydrogen atoms may also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, and formyl. Examples of heteroaryl groups include, without limitation, pyridinyl, thiazolyl, thiadiazoyl, isoquinolinyl, pyrazolyl, oxazolyl, oxadiazoyl, triazolyl, and pyrrolyl groups. Subsets of the term heteroaryl are (1) the term "pyridinyl" which denotes compounds of the formula:

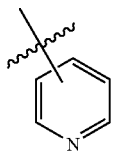

(2) the term "substituted pyridinyl" which is defined as a pyridinyl radical in which one or more hydrogen atoms is replaced by a substituent group selected from acyl, amino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl and (3) the term "acylamino pyridinyl" which denotes a pyridinyl radical in which one hydrogen atom is replaced by an acylamino group, additionally, one or more additional hydrogen atoms can also be replaced by a substituent group selected from acyl, amino, acylamino, acyloxy, carboalkoxy, carboxy, carboxyamido, cyano, halo, hydroxyl, nitro, thio, thiocarbonyl, alkyl, alkenyl, alkynyl, cycloalkyl, heterocyclyl, aryl, heteroaryl, alkoxy, aryloxy, sulfinyl, sulfonyl, N-sulfonylcarboxyamido, and N-acylaminosulfonyl.

The term "cycloalkyl" or "cycloalkyl ring" is defined as a saturated or partially unsaturated carbocyclic ring in a single or fused carbocyclic ring system having from three to twelve ring members. In one embodiment, a cycloalkyl is a ring system having three to twelve ring members. One or more hydrogen atoms may also be replaced by a substituent group selected from acyl, amino, acylamino, acyloxy, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a cycloalkyl group include, without limitation, cyclopropyl, cyclobutyl, cyclohexyl, and cycloheptyl.

The term "heterocyclyl," "heterocyclic" or "heterocyclyl ring" is defined as a saturated or partially unsaturated ring containing one to four hetero atoms or hetero groups selected from O, N, NH,

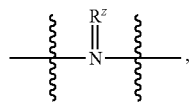

wherein $R^z$ is as defined for $R^x$,

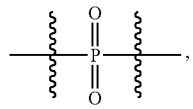

S,

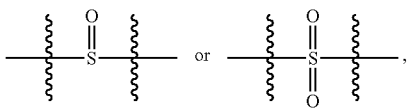

in a single or fused heterocyclic ring system having from three to twelve ring members. In one embodiment, a heterocyclyl is a ring system having three to seven ring members. One or more hydrogen atoms may also be replaced by a substituent group selected from acyl, amino, acylamino, acyloxy, oxo, thiocarbonyl, imino, carboalkoxy, carboxy, carboxyamido, cyano, halo, hydroxyl, nitro, thio, alkyl, alkenyl, alkynyl, cycloalkyl, heterocyclyl, aryl, heteroaryl, alkoxy, aryloxy, sulfinyl, sulfonyl and formyl. Examples of a heterocyclyl group include, without limitation, morpholinyl, piperidinyl, and pyrrolidinyl.

The term "alkoxy" denotes oxy-containing radicals substituted with an alkyl, cycloalkyl or heterocyclyl group. Examples include, without limitation, methoxy, tert-butoxy, benzyloxy and cyclohexyloxy.

The term "aryloxy" denotes oxy-containing radicals substituted with an aryl or heteroaryl group. Examples include, without limitation, phenoxy.

The term "amino acid side chain" denotes any side chain (R group) from a naturally-occurring or a non-naturally occurring amino acid.

The term "sulfinyl" is defined as a tetravalent sulfur radical substituted with an oxo substituent and a second substituent selected from the group consisting of alkyl, cycloalkyl, heterocyclyl, aryl, or heteroaryl group.

The term "sulfonyl" is defined as a hexavalent sulfur radical substituted with two oxo substituents and a third substituent selected from alkyl, cycloalkyl, heterocyclyl aryl, or heteroaryl.

The term "carbamate amino protecting group" is defined as a recognized amino protecting group that when bound to an amino group forms a carbamate. Examples of carbamate amino protecting groups can be found in "Protective Groups in Organic Synthesis" by Theodora W. Greene, John Wiley and Sons, New York, 1981. Examples of carbamate amino protecting groups include benzyloxycarbonyl, t-butoxycarbonyl, t-amyloxycarbonyl, isobornyloxycarbonyl, adamantyloxycarbonyl, chlorobenzyloxycarbonyl, nitrobenzyloxycarbonyl or the like.

The salts of the compounds of the invention include acid addition salts and base addition salts. In one embodiment, the salt is a pharmaceutically acceptable salt of the compound of Formula I. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of the compounds of the invention may be prepared from an inorganic acid or an organic acid. Examples of such inorganic acids include, without limitation, hydrochloric, hydrobromic, hydroiodic, nitric, carbonic, sulfuric and phosphoric acid. Examples of appropriate organic acids may be selected from aliphatic, cycloaliphatic, aromatic, arylaliphatic, heterocyclic, carboxylic and sulfonic classes of organic acids, examples of which include, without limitation, formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, R-hydroxybutyric, malonic, galactic, and galacturonic acid. Suitable pharmaceutically-acceptable base addition salts of compounds of the invention include, but are not limited to, metallic salts made from aluminum, calcium, lithium, magnesium, potassium, sodium and zinc or organic salts made from N,N'-dibenzylethylenediamine, chloroprocaine, choline, diethanolamine, ethylenediamine, N-methylglucamine, lysine and procaine. All of these salts may be prepared by conventional means from the corresponding compound of the invention by treating, for example, the compound of the invention with the appropriate acid or base.

The compounds of the invention can possess one or more asymmetric carbon atoms and are thus capable of existing in the form of optical isomers as well as in the form of racemic or non-racemic mixtures thereof. The compounds of the invention can be utilized in the present invention as a single isomer or as a mixture of stereochemical isomeric forms. Diastereoisomers, i.e., nonsuperimposable stereochemical isomers, can be separated by conventional means such as chromatography, distillation, crystallization or sublimation. The optical isomers can be obtained by resolution of the racemic mixtures according to conventional processes, for example by formation of diastereoisomeric salts by treatment with an optically active acid or base. Examples of appropriate acids include, without limitation, tartaric, diacetyltartaric, dibenzoyltartaric, ditoluoyltartaric and camphorsulfonic acid. The mixture of diastereomers can be separated by crystallization followed by liberation of the optically active bases from these salts. An alternative process for separation of optical isomers includes the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to obtain the enantiomerically pure compound. The optically active compounds of the invention can likewise be obtained by utilizing optically active starting materials. These isomers may be in the form of a free acid, a free base, an ester or a salt.

The invention also embraces isolated compounds. An isolated compound refers to a compound which represents at least 10%, such as at least 20%, such as at least 50% and further such as at least 80% of the compound present in the mixture. In one embodiment, the compound, a pharmaceutically acceptable salt thereof, or a pharmaceutical composition comprising the compound exhibits a detectable (i.e. statistically significant) antimicrobial activity when tested in conventional biological assays such as those described herein.

In one embodiment, the invention relates to compounds having the Formula (I):

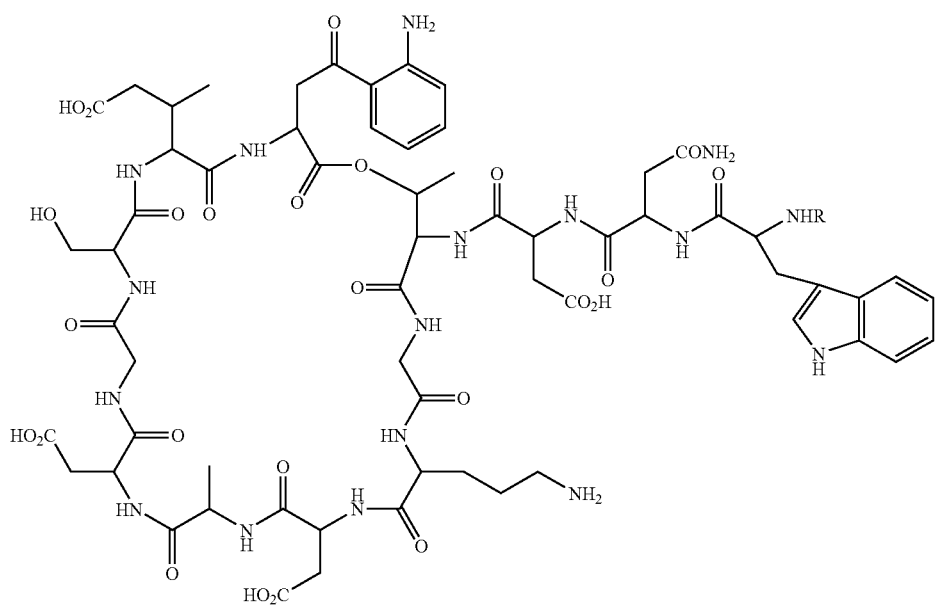

and pharmaceutically acceptable salts thereof, wherein:
R is:

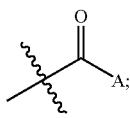

and
A is chosen from alkyl, alkenyl, cycloalkyl, aryl, heteroaryl, and $NHR^4$,
wherein $R^4$ is chosen from alkyl and cycloalkyl.

In one embodiment, A is chosen from alkyl, such as $C_{1-14}$ alkyl, such as $C_{1-6}$ alkyl, and further such as $C_{4-6}$ alkyl. In a further embodiment, A is chosen from alkyl substituted by one or more cycloalkyl or aryl.

In another embodiment, A is chosen from:
a) unsubstituted $C_1$-$C_{14}$ alkyl;
b) $C_4$-$C_6$ alkyl substituted with one or more cycloalkyl;
c) $C_4$-$C_6$ alkyl interrupted by one or more aryl;
d) $C_1$-$C_6$ alkyl substituted with one or more aryl; and
e) $C_6$ alkyl interrupted by one or more cycloalkyl.

In another embodiment, A is a $C_1$-$C_6$ alkyl substituted with one or more cyclohexyl. In another embodiment, A is a $C_1$-$C_6$ alkyl interrupted by one or more phenyl. In another embodiment, A is a $C_1$-$C_6$ alkyl substituted with one or more phenyl.

In one embodiment, A is chosen from:
a) unsubstituted $C_1$-$C_{12}$ alkenyl; and
b)

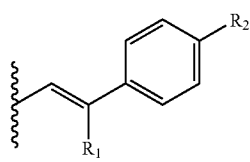

wherein $R_1$ is chosen from hydrogen or methyl; and $R_2$ is chosen from phenyl, unsubstituted $C_3$-$C_7$ alkyl, and $OR_3$, wherein $R_3$ is unsubstituted $C_1$-$C_6$ alkyl. In another embodiment, $R_1$ is methyl and $R_2$ is unsubstituted $C_3$-$C_7$ alkyl.

In one embodiment, A is chosen from:
a) $C_3$-$C_8$ cycloalkyl substituted with one or more unsubstituted $C_1$-$C_{10}$ alkyl;
b) unsubstituted $C_{10}$-$C_{12}$ cycloalkyl;
c) $C_3$-$C_8$ cycloalkyl substituted with $C_3$-$C_8$ cycloalkyl; and
d) $C_3$-$C_8$ cycloalkyl substituted with phenyl, wherein said phenyl may be optionally substituted with one or more halogens. In another embodiment, A is chosen from cyclohexyl and cyclopropyl, each of which may be substituted with one or more unsubstituted $C_1$-$C_{10}$ alkyl. In another embodiment, A is $C_3$-$C_8$ cycloalkyl substituted with one or more phenyl, wherein said phenyl may be optionally substituted with one or more chlorine atoms.

In one embodiment, A is chosen from:
a) phenyl substituted with unsubstituted $C_1$-$C_8$ alkyl;
b) phenyl substituted with $OR_4$, wherein $R_4$ is unsubstituted $C_1$-$C_{15}$ alkyl;
c) phenyl substituted with cycloalkyl, wherein said cycloalkyl is substituted with one or more unsubstituted $C_1$-$C_8$ alkyl;
d) phenyl substituted with phenyl-$OR_{4*}$, wherein $R_{4*}$ is unsubstituted $C_1$-$C_8$ alkyl;

e) phenyl substituted with phenyl, optionally substituted with one or more halogen atoms; and
f) phenyl substituted with one or more phenyl.

In another embodiment, A is phenyl substituted with cyclohexyl, wherein said cyclohexyl is substituted with unsubstituted $C_1$-$C_8$ alkyl. In another embodiment, A is phenyl substituted with phenyl, optionally substituted with one or more chlorine atoms.

In one embodiment, A is chosen from:
a) thiophenyl substituted with unsubstituted $C_1$-$C_8$ alkyl; and
b) thiophenyl substituted with phenyl-$R_5$ where $R_5$ is chosen from hydrogen, chloro, phenyl-$OR_6$, and $SR_6$ wherein $R_6$ is unsubstituted $C_1$-$C_6$ alkyl.

In one embodiment, A is chosen from $NHR^4$, wherein $R^4$ is chosen from unsubstituted $C_1$-$C_{12}$ alkyl, cyclohexyl substituted with one or more unsubstituted $C_1$-$C_6$ alkyl or

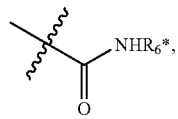

wherein $R_{6*}$ is phenyl optionally substituted with $C_1$-$C_7$ unsubstituted alkyl.

In one embodiment, R is chosen from a substituent of Table I:

TABLE I

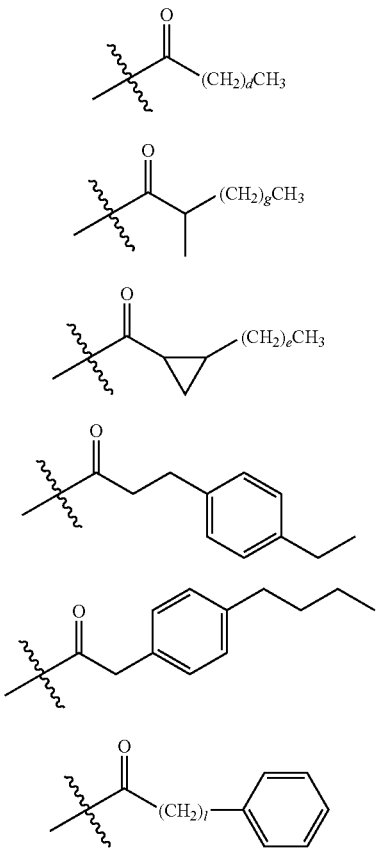

TABLE I-continued
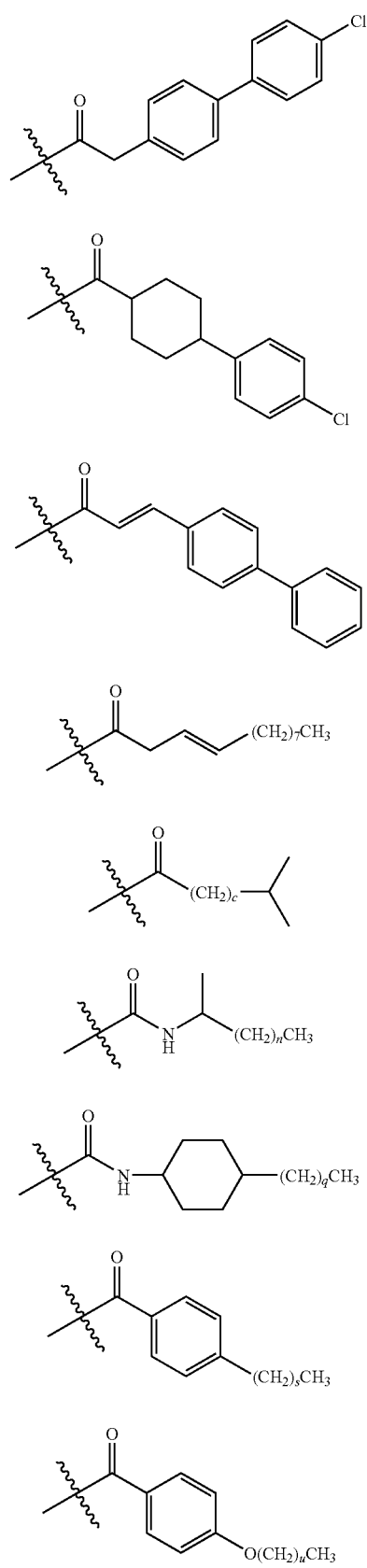
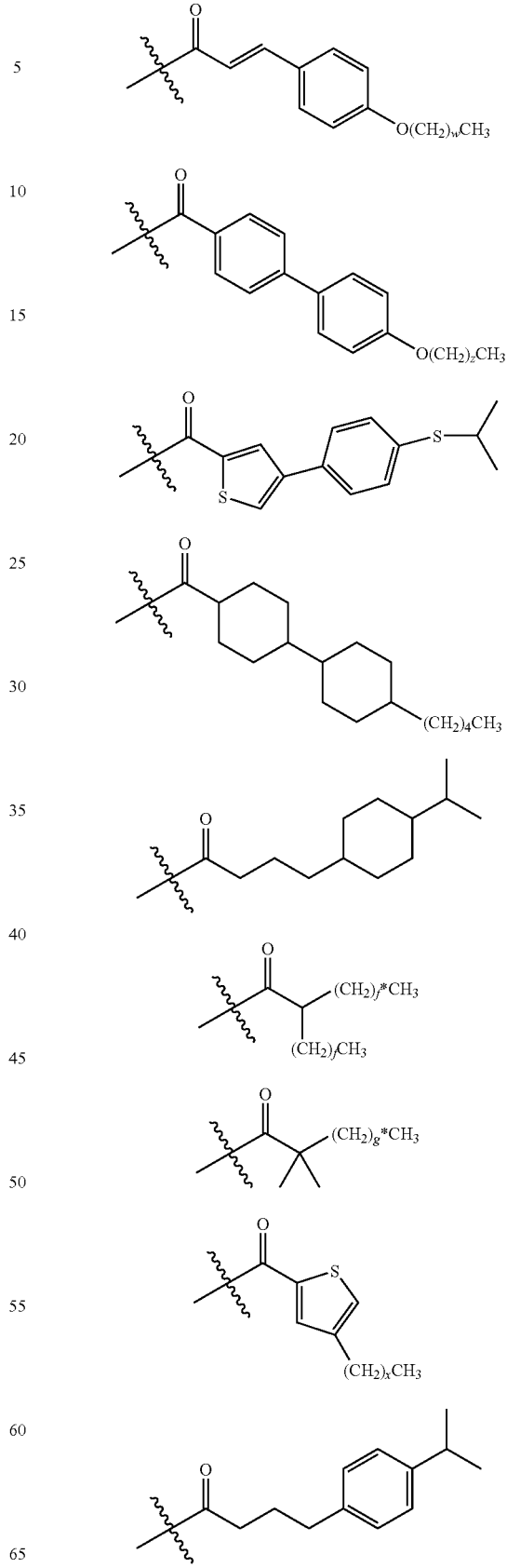

TABLE I-continued
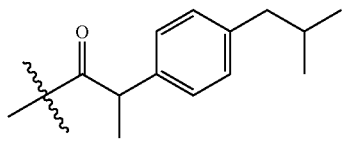 [SMILES: *C(=O)C(C)c1ccc(CC(C)C)cc1]
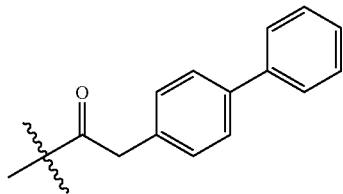 [SMILES: *C(=O)Cc1ccc(-c2ccccc2)cc1]
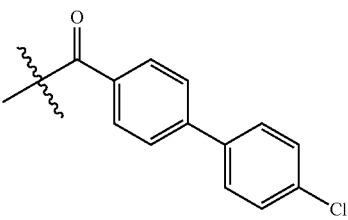 [SMILES: *C(=O)c1ccc(-c2ccc(Cl)cc2)cc1]
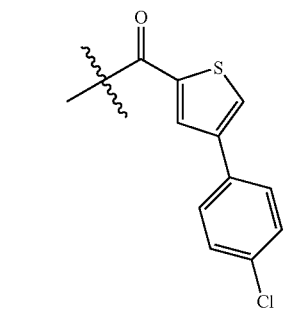 [SMILES: *C(=O)c1cc(-c2ccc(Cl)cc2)cs1]
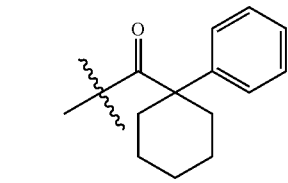 [SMILES: *C(=O)C1(c2ccccc2)CCCCC1]
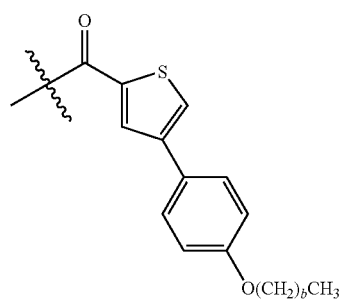
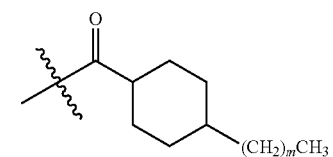
TABLE I-continued
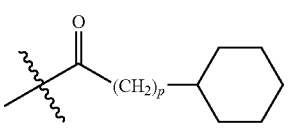
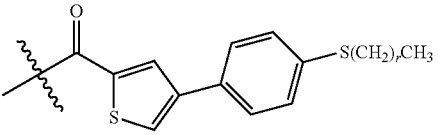
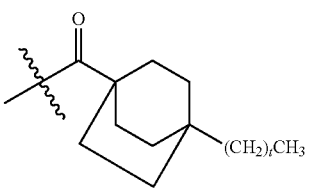
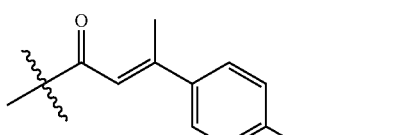
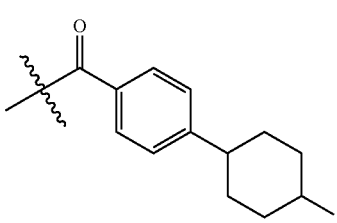
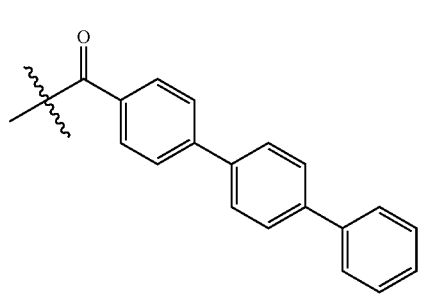 [SMILES: *C(=O)c1ccc(-c2ccc(-c3ccccc3)cc2)cc1]
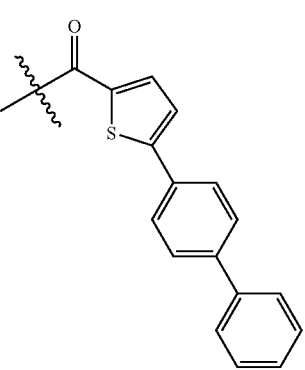 [SMILES: *C(=O)c1ccc(-c2ccc(-c3ccccc3)cc2)s1]

TABLE I-continued

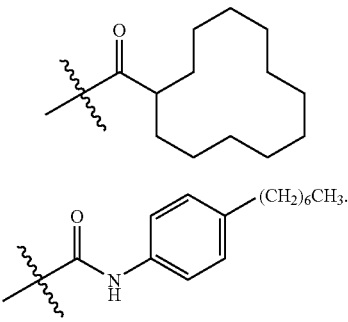

In one embodiment, variable b of Table I is an integer chosen from 0 to 7. In another embodiment, variable b is 0, 1, 2, 3, 4, 5, 6, or 7. In a further embodiment, variable b is 5. In one embodiment, variable c of Table I is an integer chosen from 6 to 10. In another embodiment, variable c is 6, 7, 8, 9, or 10. In a further embodiment, variable c is 6, 9, or 10. In one embodiment, variable d in Table 1 is an integer chosen from 6 to 14. In another embodiment, variable d is 6, 7, 8, 9, 10, 11, 12, 13, or 14. In another embodiment, variable d is 7, 9, 10, 11, 12, or 13. In a further embodiment, variable d is 10, 11, 12 or 13. In one embodiment, variable e of Table I is an integer chosen from 6 to 8. In another embodiment, e is 6, 7, or 8. In a further embodiment, variable e is 7. Each of variables f and f* of Table I is independently an integer chosen from 2 to 6. In one embodiment, each of variables f and f* is 2, 3, 4, 5, or 6. In another embodiment, each of variables f and f* is independently 3, 4, or 5. In a further embodiment variable f is 3 and variable f* is 5. In one embodiment, variable g of Table I is an integer chosen from 6 to 10. In another embodiment, variable g is 6, 7, 8, 9, or 10. In another embodiment, variable g is 6. In one embodiment, variable g* is an integer chosen from 6 to 10. In another embodiment, variable g* is 6, 7, 8, 9, or 10. In a further embodiment, variable g* is 8. In one embodiment, variable I of Table I is an integer chosen from 5 or 6. In one embodiment, variable m of Table I is an integer chosen from 3 to 9. In another embodiment, variable m is 3, 4, 5, 6, 7, 8, or 9. In a further embodiment, variable m is 3, 4, 5, or 6. In one embodiment, variable n of Table I is an integer chosen from 8 to 10. In another embodiment, variable n is 8, 9, or 10. In a further embodiment, variable n is 8. In one embodiment, variable p is an integer chosen from 4 to 8. In a another embodiment, variable p is 4, 5, 6, 7, or 8. In a further embodiment, variable p is 4, 5, or 6. In one embodiment, variable q of Table I is an integer chosen from 4 to 7. In another embodiment, variable q is 4, 5, 6, or 7. In a further embodiment, variable q is 4. In one embodiment, variable r of Table I is an integer chosen from 2 to 6. In another embodiment, variable r is 2, 3, 4, 5, or 6. In another embodiment, variable r is 2, 3, 4, or 5. In a further embodiment, variable r is 2 or 5. In one embodiment, variable s is an integer chosen from 4 to 9. In another embodiment, variable s is 4, 5, 6, 7, 8 or 9. In another embodiment, variable s is 4, 5, 6 or 7. In a further embodiment variable s is 6 or 7. In one embodiment, variable t of Table I is an integer chosen from 4 to 9. In another embodiment, variable t is 4, 5, 6, 7, 8, or 9. In a further embodiment variable t is 4 or 5. In one embodiment, variable u of Table I is an integer chosen from 4 to 14. In another embodiment, variable u is 4, 5, 6, 7, 8, 9, 10, 11, 12, 13, or 14. In another embodiment, variable u is 5, 7, 8, 9, 11, or 14. In a further embodiment, variable u is 5, 7, 8, 9, and 14. In one embodiment, variable v of Table I is an integer chosen from 3 to 7. In another embodiment, variable v is 3, 4, 5, 6, or 7. In another embodiment, variable v is 3, 4, or 5. In one embodiment, variable w of Table I is an integer chosen from 3 to 7. In another embodiment, variable w is 3, 4, 5, 6, or 7. In another embodiment, variable w is 4 or 5. In one embodiment, variable x of Table I is an integer chosen from 6 to 10. In another embodiment, variable x is 6, 7, 8, 9, or 10. In another embodiment variable x is 6. In one embodiment, variable y of Table I is an integer chosen from 1 to 5. In another embodiment, variable y is 1, 2, 3, 4, or 5. In another embodiment, variable y is 2, 3, or 4. In a further embodiment, variable y is 2 or 4. In one embodiment, variable z of Table I is an integer chosen from 0 to 7. In another embodiment, variable z is 0, 1, 2, 3, 4, 5, 6, or 7. In a further embodiment, variable z is 2, 3, 4, 5, 6, or 7.

In another embodiment, R is chosen from a substituent of Table II:

TABLE II

| Compound Number | R |
| --- | --- |
| 1 | |
| 2 | |
| 3 | |

TABLE II-continued

| Compound Number | R |
|---|---|
| 4 | (acyl group with C=C double bond, long chain) |
| 5 | (saturated acyl long chain) |
| 6 | (saturated acyl long chain) |
| 7 | (saturated acyl long chain) |
| 8 | (branched acyl group with butyl and hexyl branches) |
| 9 | (acyl group with iso-terminal methyl branch) |
| 10 | (acyl group with iso-terminal methyl branch, longer) |
| 11 | (acyl group with iso-terminal methyl branch, longer) |
| 12 | (acyl group with gem-dimethyl at α-carbon) |

TABLE II-continued
| Compound Number | R |
|---|---|
| 13 | 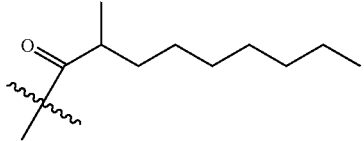 [SMILES: *C(=O)C(C)CCCCCCC] |
| 14 | 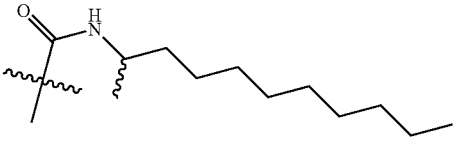 [SMILES: *C(=O)NC(C)CCCCCCCCC] |
| 15 | 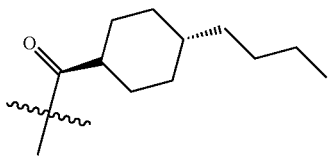 |
| 16 | 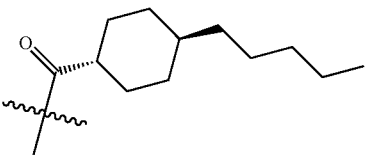 [SMILES: *C(=O)[C@H]1CC[C@H](CCCCC)CC1] |
| 17 | 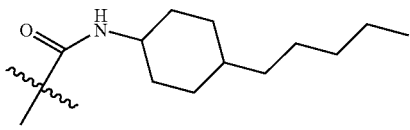 [SMILES: *C(=O)NC1CCC(CCCCC)CC1] |
| 18 | 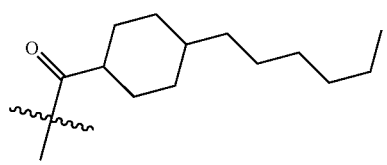 [SMILES: *C(=O)C1CCC(CCCCCC)CC1] |
| 19 | 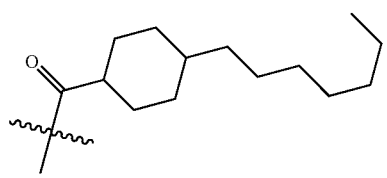 [SMILES: *C(=O)C1CCC(CCCCCCC)CC1] |
| 20 | 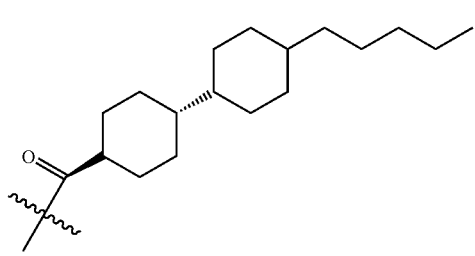 |

TABLE II-continued
| Compound Number | R |
|---|---|
| 21 | 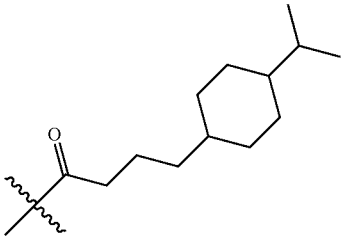 [SMILES: *C(=O)CCCC1CCC(C(C)C)CC1] |
| 22 | 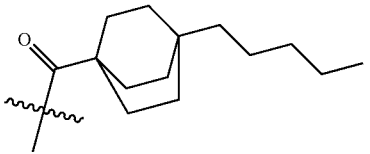 [SMILES: *C(=O)C12CCC(CCCCC)(CC1)CC2] |
| 23 | 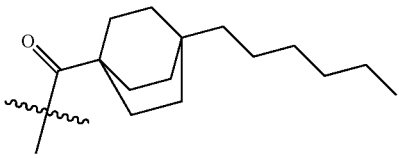 [SMILES: *C(=O)C12CCC(CCCCCC)(CC1)CC2] |
| 24 | 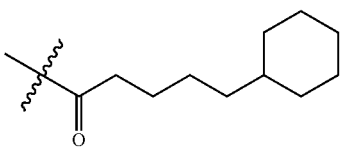 [SMILES: *C(=O)CCCCC1CCCCC1] |
| 25 | 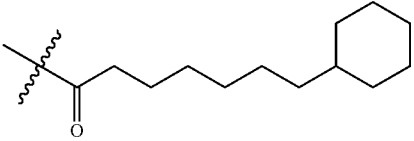 [SMILES: *C(=O)CCCCCCC1CCCCC1] |
| 26 | 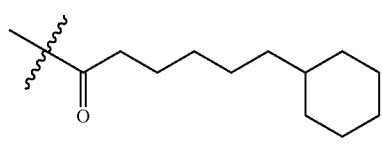 [SMILES: *C(=O)CCCCCC1CCCCC1] |
| 27 | 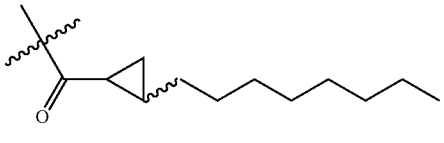 [SMILES: *C(=O)C1CC1CCCCCCCC] |
| 28 | 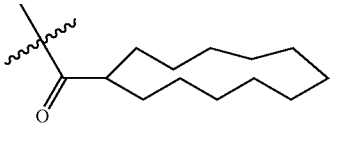 |
| 29 | 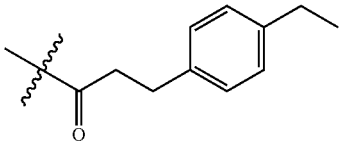 [SMILES: *C(=O)CCc1ccc(CC)cc1] |

TABLE II-continued
| Compound Number | R |
|---|---|
| 30 | 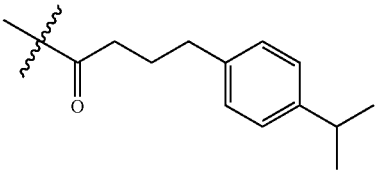 [SMILES: *C(=O)CCCc1ccc(C(C)C)cc1] |
| 31 | 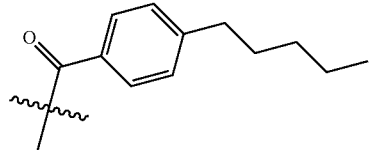 [SMILES: *C(=O)c1ccc(CCCCC)cc1] |
| 32 | 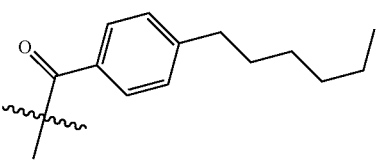 [SMILES: *C(=O)c1ccc(CCCCCC)cc1] |
| 33 | 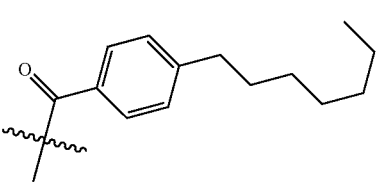 [SMILES: *C(=O)c1ccc(CCCCCCC)cc1] |
| 34 | 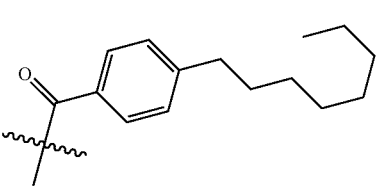 |
| 35 | 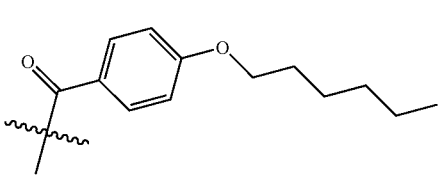 [SMILES: *C(=O)c1ccc(OCCCCCC)cc1] |
| 36 | 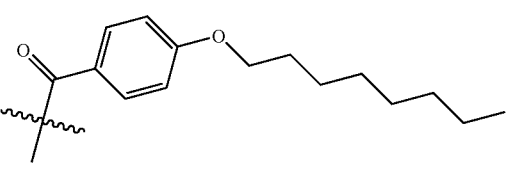 [SMILES: *C(=O)c1ccc(OCCCCCCCC)cc1] |
| 37 | 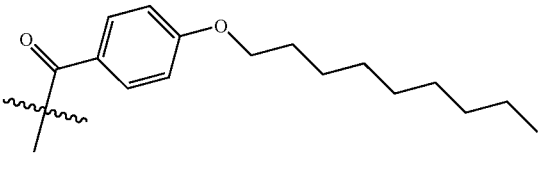 [SMILES: *C(=O)c1ccc(OCCCCCCCCC)cc1] |
| 38 | 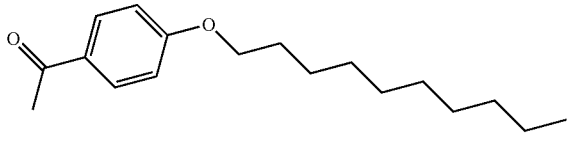 |

TABLE II-continued
| Compound Number | R |
|---|---|
| 39 | 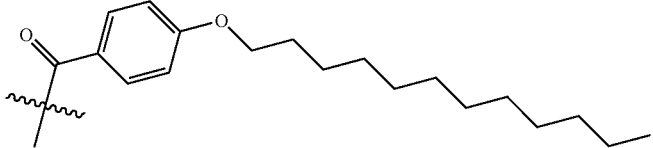 [SMILES: *C(=O)c1ccc(OCCCCCCCCCCCC)cc1] |
| 40 | 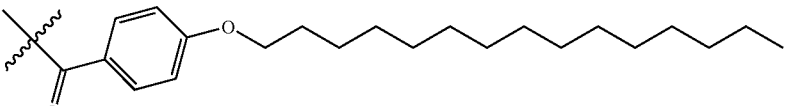 |
| 41 | 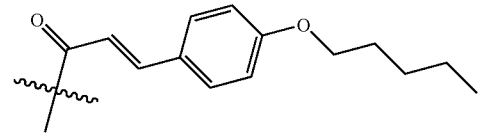 [SMILES: *C(=O)/C=C/c1ccc(OCCCCC)cc1] |
| 42 | 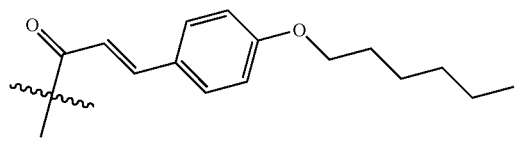 [SMILES: *C(=O)/C=C/c1ccc(OCCCCCC)cc1] |
| 43 | 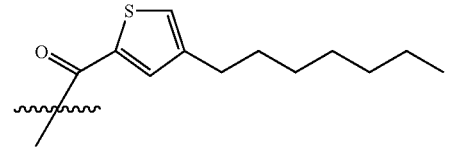 |
| 44 | 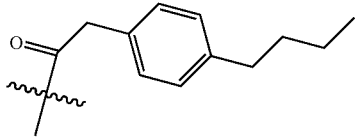 [SMILES: *C(=O)Cc1ccc(CCCC)cc1] |
| 45 | 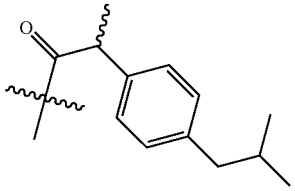 [SMILES: *C(=O)C(C)c1ccc(CC(C)C)cc1] |
| 46 | 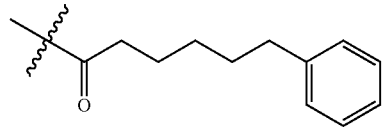 [SMILES: *C(=O)CCCCCc1ccccc1] |
| 47 | 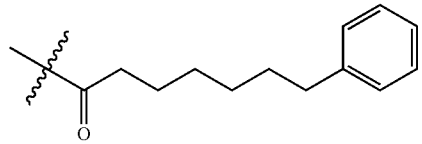 [SMILES: *C(=O)CCCCCCc1ccccc1] |
| 48 | 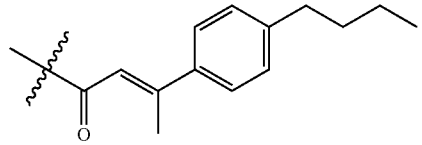 [SMILES: *C(=O)/C=C(\C)c1ccc(CCCC)cc1] |

TABLE II-continued
| Compound Number | R |
|---|---|
| 49 | 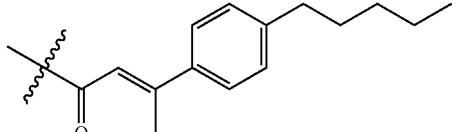 |
| 50 | 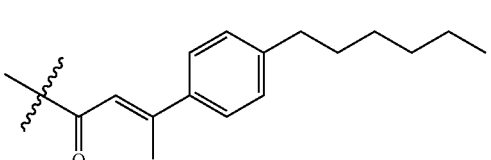 |
| 51 | 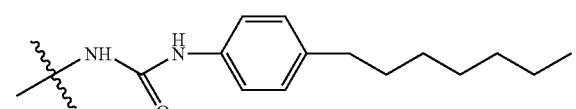 |
| 52 | 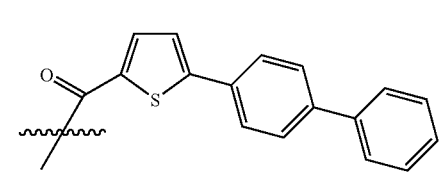 [SMILES: *C(=O)c1ccc(-c2ccc(-c3ccccc3)cc2)s1] |
| 53 | 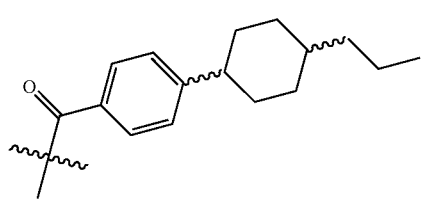 [SMILES: *C(=O)c1ccc(C2CCC(CCC)CC2)cc1] |
| 54 | 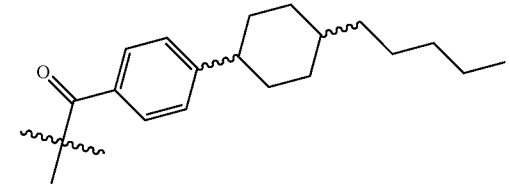 [SMILES: *C(=O)c1ccc(C2CCC(CCCCC)CC2)cc1] |
| 55 | 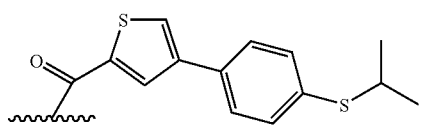 [SMILES: *C(=O)c1cc(-c2ccc(SC(C)C)cc2)cs1] |
| 56 | 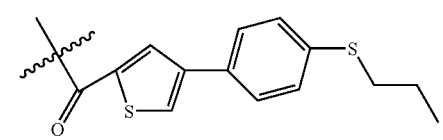 [SMILES: *C(=O)c1cc(-c2ccc(SCCC)cc2)cs1] |
| 57 | 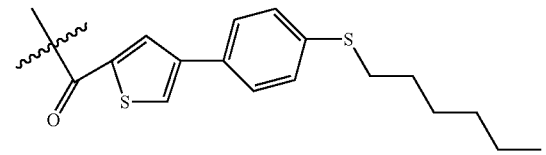 [SMILES: *C(=O)c1cc(-c2ccc(SCCCCCC)cc2)cs1] |

TABLE II-continued
| Compound Number | R |
|---|---|
| 58 | 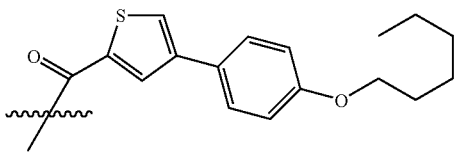 |
| 59 | 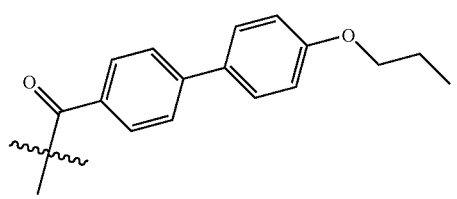 [SMILES: *C(=O)c1ccc(-c2ccc(OCCC)cc2)cc1] |
| 60 | 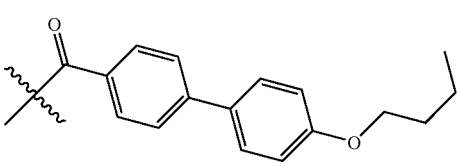 [SMILES: *C(=O)c1ccc(-c2ccc(OCCCC)cc2)cc1] |
| 61 | 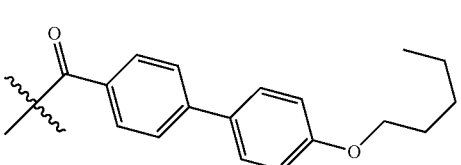 |
| 62 | 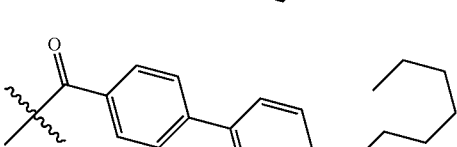 |
| 63 | 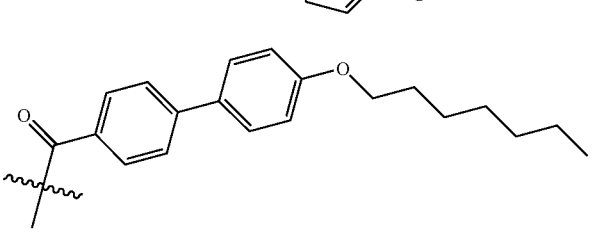 |
| 64 | 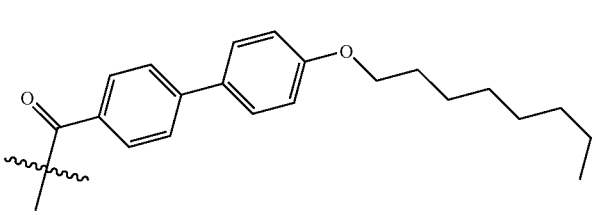 [SMILES: *C(=O)c1ccc(-c2ccc(OCCCCCCCC)cc2)cc1] |
| 65 | 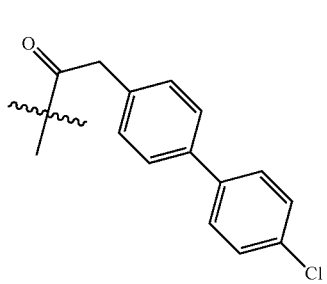 [SMILES: *C(=O)Cc1ccc(-c2ccc(Cl)cc2)cc1] |

TABLE II-continued
| Compound Number | R |
|---|---|
| 66 | 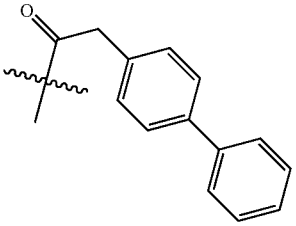 [SMILES: *C(=O)Cc1ccc(-c2ccccc2)cc1] |
| 67 | 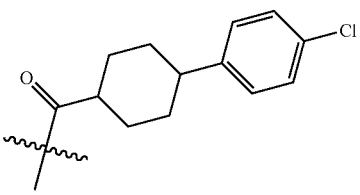 [SMILES: *C(=O)C1CCC(c2ccc(Cl)cc2)CC1] |
| 68 | 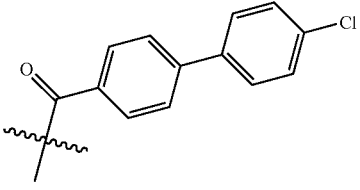 [SMILES: *C(=O)c1ccc(-c2ccc(Cl)cc2)cc1] |
| 69 | 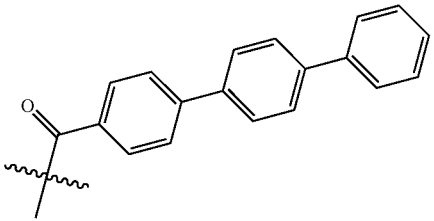 [SMILES: *C(=O)c1ccc(-c2ccc(-c3ccccc3)cc2)cc1] |
| 70 | 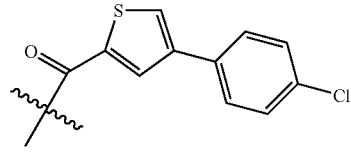 [SMILES: *C(=O)c1cc(-c2ccc(Cl)cc2)cs1] |
| 71 | 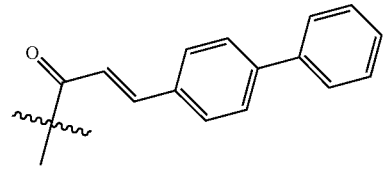 [SMILES: *C(=O)/C=C/c1ccc(-c2ccccc2)cc1] |
| 72 | 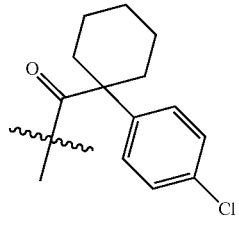 [SMILES: *C(=O)C1(c2ccc(Cl)cc2)CCCCC1] |

In another embodiment, R is chosen from a substituent of Table III:
TABLE III
| Compound Number | R |
|---|---|
| 10 | 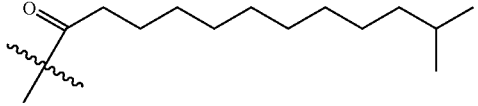 [SMILES: *C(=O)CCCCCCCCCC(C)C] |
| 11 | 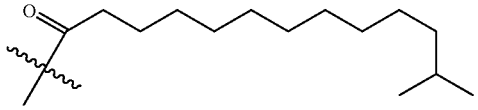 [SMILES: *C(=O)CCCCCCCCCCC(C)C] |
| 14 | 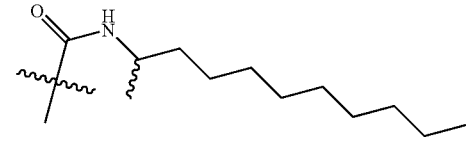 [SMILES: *C(=O)NC(C)CCCCCCCCC] |
| 16 | 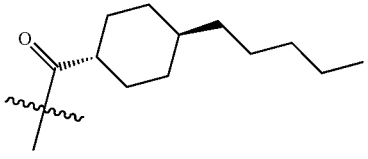 [SMILES: *C(=O)[C@H]1CC[C@H](CCCCC)CC1] |
| 17 | 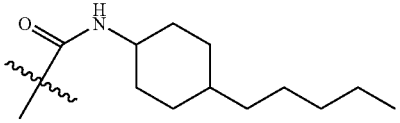 [SMILES: *C(=O)NC1CCC(CCCCC)CC1] |
| 18 | 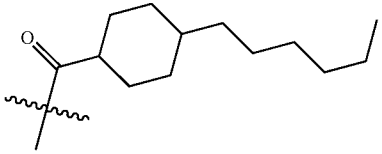 [SMILES: *C(=O)C1CCC(CCCCCC)CC1] |
| 19 | 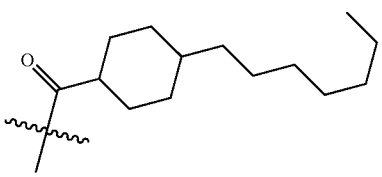 [SMILES: *C(=O)C1CCC(CCCCCCC)CC1] |
| 20 | 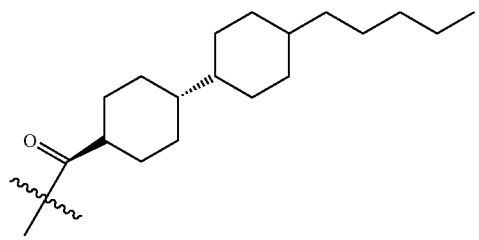 |
| 22 | 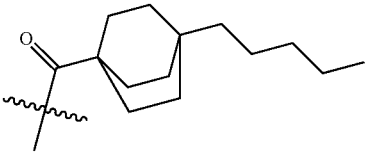 [SMILES: *C(=O)C12CCC(CCCCC)(CC1)CC2] |

TABLE III-continued
| Compound Number | R |
|---|---|
| 23 | 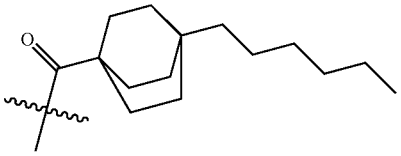 [SMILES: *C(=O)C12CCC(CCCCCC)(CC1)CC2] |
| 25 | 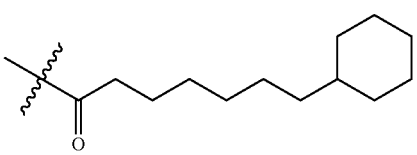 [SMILES: *C(=O)CCCCCCC1CCCCC1] |
| 28 | 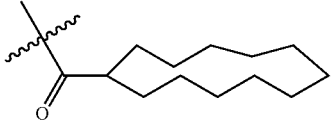 [SMILES: *C(=O)C1CCCCCCCCCCC1] |
| 33 | 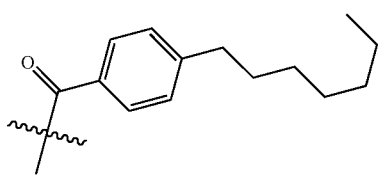 [SMILES: *C(=O)c1ccc(CCCCCCC)cc1] |
| 34 | 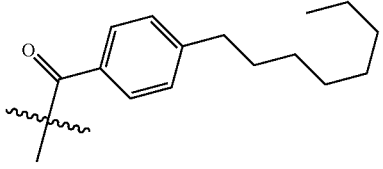 [SMILES: *C(=O)c1ccc(CCCCCCCC)cc1] |
| 36 | 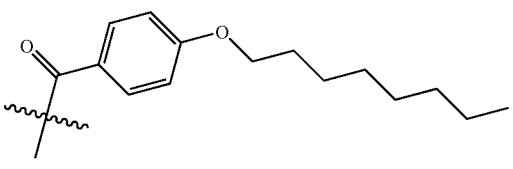 [SMILES: *C(=O)c1ccc(OCCCCCCCC)cc1] |
| 37 | 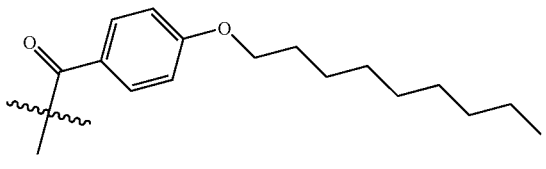 [SMILES: *C(=O)c1ccc(OCCCCCCCCC)cc1] |
| 38 | 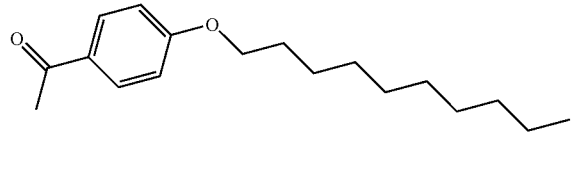 |
| 42 | 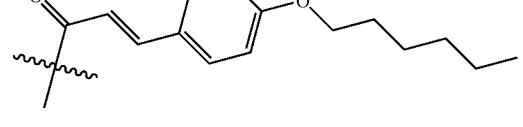 |

TABLE III-continued
| Compound Number | R |
|---|---|
| 43 | 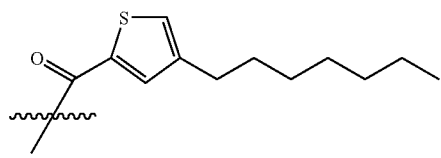 [SMILES: *C(=O)c1cc(CCCCCCC)cs1] |
| 49 | 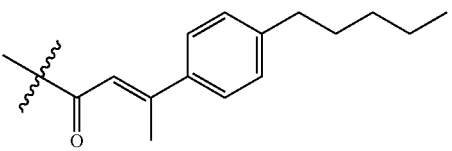 [SMILES: *C(=O)/C=C(\C)c1ccc(CCCCC)cc1] |
| 50 | 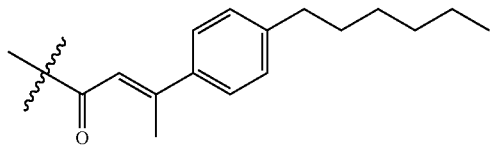 [SMILES: *C(=O)/C=C(\C)c1ccc(CCCCCC)cc1] |
| 51 | 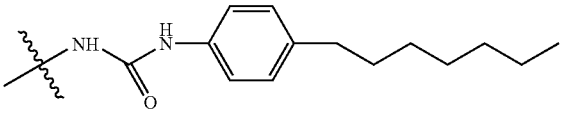 [SMILES: *NC(=O)Nc1ccc(CCCCCCC)cc1] |
| 52 | 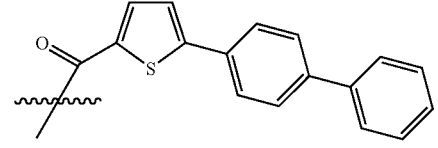 [SMILES: *C(=O)c1ccc(-c2ccc(-c3ccccc3)cc2)s1] |
| 53 | 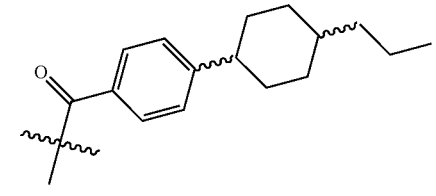 [SMILES: *C(=O)c1ccc(C2CCC(CCC)CC2)cc1] |
| 58 | 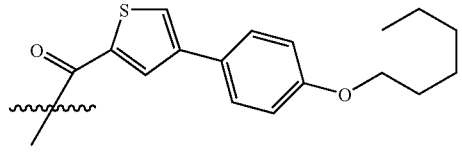 [SMILES: *C(=O)c1cc(-c2ccc(OCCCCCC)cc2)cs1] |
| 61 | 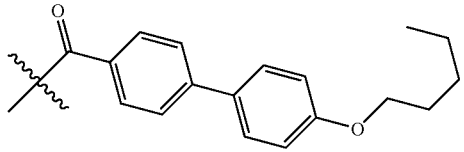 |
| 62 | 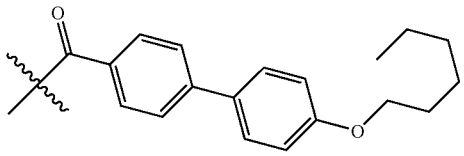 [SMILES: *C(=O)c1ccc(-c2ccc(OCCCCCC)cc2)cc1] |

TABLE III-continued

| Compound Number | R |
|---|---|
| 63 | 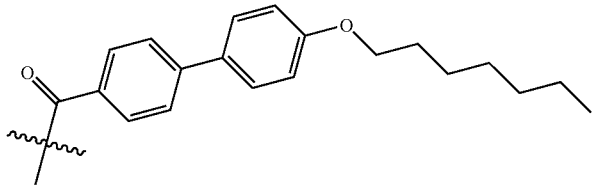 [SMILES: *C(=O)c1ccc(-c2ccc(OCCCCCCC)cc2)cc1] |
| 64 | 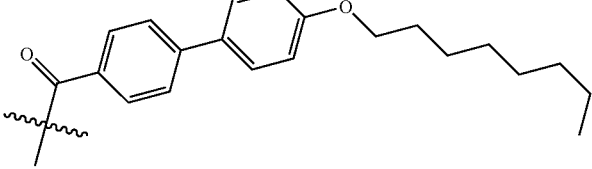 |
| 69 | 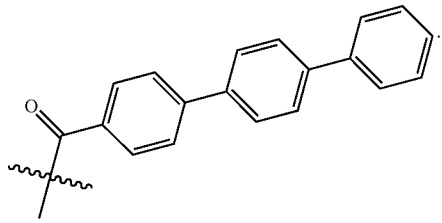 [SMILES: *C(=O)c1ccc(-c2ccc(-c3ccccc3)cc2)cc1] |

In a further embodiment, R is chosen from a substituent of Table IV:

TABLE IV

| Compound Number | R |
|---|---|
| 33 | 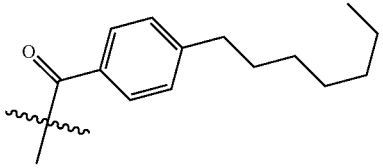 [SMILES: *C(=O)c1ccc(CCCCCCC)cc1] |
| 49 | 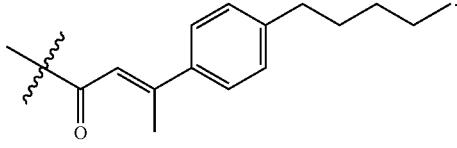 [SMILES: *C(=O)/C=C(\C)c1ccc(CCCCC)cc1] |

A further object of the invention is pharmaceutical compositions or formulations comprising compounds disclosed herein, or salts thereof.

The pharmaceutical compositions can be formulated for oral, intravenous, intramuscular, subcutaneous or parenteral administration for the therapeutic or prophylactic treatment of diseases, such as bacterial infections.

The pharmaceutical preparations disclosed herein may be prepared in accordance with standard procedures and are administered at dosages that are selected to reduce, prevent or eliminate infection (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the compounds disclosed herein in association with one or more nontoxic, pharmaceutically-acceptable carriers and/or diluents and/or adjuvants and/or excipients. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art. Nonlimiting examples of carriers and excipients include corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral or parenteral administration, compounds of the present invention can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs, preparations of the invention may contain conventional additives such as suspending agents, emulsifying agents, non-aqueous agents, preservatives, coloring agents and flavoring agents. Nonlimiting examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, the pharmaceutical composition can be dissolved or suspended in any of the commonly used intravenous fluids and administered by infusion. Intravenous fluids include, without limitation, physiological saline or Ringer's solution. Intravenous administration may be accomplished by using, without limitation, syringe, minipump or intravenous line.

Pharmaceutical compositions of this invention for parenteral injection comprise pharmaceutically-acceptable aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, benzyl alcohol, polyols (such as glycerol, propylene glycol, and polyethylene glycol), and suitable mixtures thereof, vegetable oils (such as corn oil or olive oil), and injectable organic esters such as ethyl oleate. Proper fluidity can be maintained, for example, by the use of coating materials such as lecithin, by the maintenance of the required particle size in the case of dispersions, and by the use of surfactants. The compositions can include various buffers.

These compositions may also contain adjuvants such as preservatives, wetting agents, emulsifying agents, and dispersing agents. They may also contain taggants or other anti-counterfeiting agents, which are well known in the art. Prevention of the action of microorganisms may be ensured by the inclusion of various antibacterial and antifungal agents, for example, paraben, chlorobutanol, and phenol sorbic acid. It may also be desirable to include isotonic agents such as sugars and sodium chloride. Prolonged absorption of the injectable pharmaceutical form may be brought about by the inclusion of agents which delay absorption, such as aluminum monostearate and gelatin.

Injectable depot forms can be made by forming microencapsulating matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations can also be prepared by entrapping the drug in liposomes or microemulsions, which are compatible with body tissues.

The injectable formulations can be sterilized, for example, by filtration through a bacterial-retaining filter, or by incorporating sterilizing agents in the form of sterile solid compositions, which can be dissolved or dispersed in sterile water or other sterile injectable medium just prior to use.

Solid dosage forms for oral administration include capsules, tablets, pills, powders, and granules. Such forms may include forms that dissolve or disintegrate quickly in the oral environment. In such solid dosage forms, the active compound can be mixed with at least one inert, pharmaceutically-acceptable excipient or carrier. Suitable excipients include, for example, (a) fillers or extenders such as starches, lactose, sucrose, glucose, mannitol, and silicic acid; (b) binders such as cellulose and cellulose derivatives (such as hydroxypropylmethylcellulose, hydroxypropylcellulose, and carboxymethylcellulose), alginates, gelatin, polyvinylpyrrolidone, sucrose, and acacia; (c) humectants such as glycerol; (d) disintegrating agents such as sodium starch glycolate, croscarmellose, agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents, such as cetyl alcohol and glycerol monostearate, fatty acid esters of sorbitan, poloxamers, and polyethylene glycols; (h) absorbents such as kaolin and bentonite clay; (i) lubricants such as talc, calcium stearate, magnesium stearate, solid polyethylene glycols, sodium lauryl sulfate, and mixtures thereof; and (j) glidants such as talc, and silicone dioxide. Other suitable excipients include, for example, sodium citrate or dicalcium phosphate. The dosage forms may also comprise buffering agents.

Solid dosage forms, including those of tablets, dragees, capsules, pills, and granules, can be prepared with coatings and shells such as functional and aesthetic enteric coatings and other coatings well known in the pharmaceutical formulating art. They may optionally contain opacifying agents and colorants. They may also be in a form capable of controlled or sustained release. Examples of embedding compositions that can be used for such purposes include polymeric substances and waxes.

The pharmaceutical compositions can be delivered using controlled (e.g., capsules) or sustained release (e.g., bioerodable matrices) delivery systems. Exemplary delayed release delivery systems for drug delivery that are suitable for administering the pharmaceutical compositions are described in U.S. Pat. Nos. 4,452,775 (issued to Kent), 5,039,660 (issued to Leonard), and 3,854,480 (issued to Zaffaroni).

In some cases, in order to prolong the effect of the drug, it may be desirable to slow the absorption of the drug following subcutaneous or intramuscular injection. This may be accomplished by the use of a liquid suspension of crystalline or amorphous material with poor water solubility. Amorphous material may be used alone or together with stabilizers as necessary. The rate of absorption of the drug then depends upon its rate of dissolution, which in turn, may depend upon crystal size and crystalline form.

Alternatively, delayed absorption of a parenterally administered drug form can be accomplished by dissolving or suspending the drug in an oil vehicle.

For intramuscular preparations, a sterile formulation of compounds according to Formula I, or suitable soluble salt forms thereof, for example hydrochloride salts, can be dissolved and administered in a pharmaceutical diluent such as Water-for-Injection (WFI), physiological saline or 5% glucose. A suitable insoluble form of the compound may be prepared and administered as a suspension in an aqueous base or a pharmaceutically acceptable oil base, e.g., an ester of a long chain fatty acid such as ethyl oleate.

A dose of an intravenous, intramuscular, or parental formulation of compounds according to Formula I may be administered as a bolus or by slow infusion. A bolus is a dose that is administered in less than 30 minutes. In one embodiment, a bolus is administered in less than 15 or less than 10 minutes. In another embodiment, a bolus is administered in less than 5 minutes. In yet another embodiment, a bolus is administered in one minute or less. An infusion is a dose that is administered at a rate of 30 minutes or greater. In one embodiment, the infusion is one hour or greater. In another embodiment, the infusion is substantially constant.

For topical use the pharmaceutical compositions can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient.

For application to the eyes or ears, the pharmaceutical composition can be presented in liquid or semiliquid form formulated in hydrophobic or hydrophilic bases as ointments, creams, lotions, paints or powders.

For rectal administration, the pharmaceutical compositions can be administered in the form of suppositories admixed with conventional carriers such as cocoa butter, polyethylene glycol or a suppository wax or other glyceride that are solid at room temperature but liquid at body temperature and therefore melt in the rectum or vaginal cavity and release the active compound.

Alternatively, the pharmaceutical compositions can be in powder form for reconstitution in the appropriate pharmaceutically acceptable carrier at the time of delivery. In another embodiment, the unit dosage form of compounds according to Formula I can be a solution of one or more compounds, or salts thereof, in a suitable diluent, in sterile hermetically sealed ampoules or sterile syringes. The concentration of the compounds according to Formula I in the unit dosage may vary, e.g. from about 1 percent to about 50 percent, depending on the compound used and its solubility and the dose desired by the physician. If the compositions contain dosage units, each dosage unit can contain from 1-500 mg of the active material. For adult human treatment, the dosage employed can range from 5 mg to 10 g, per day, depending on the route and frequency of administration.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols. Likewise, methods for using the claimed compositions for treating cells in culture, for example, to eliminate or reduce the level of bacterial contamination of a cell culture, utilize art-recognized protocols for treating cell cultures with antibacterial agent(s) with the only substantial procedural modification being the substitution of the compounds of the present invention for the drugs in the art-recognized protocols.

In one embodiment, the invention provides a method for treating an infection in a subject by administering a therapeutically-effective amount of one or more compounds of Formula I or compositions thereof. In one embodiment, the method comprises administering to a subject in need thereof a pharmaceutical composition comprising at least one of the compounds described herein. In one embodiment, the pharmaceutical composition can comprise any one of the compounds described herein as the sole active compound or in combination with another compound, composition, or biological material.

The terms "treatment," "therapeutic method," and their cognates refer to both therapeutic treatment and prophylactic/preventative measures. Those in need of treatment may include individuals already having a particular medical disease as well as those at risk for the disease (i.e., those who are likely to ultimately acquire the disorder). A therapeutic method results in the prevention or amelioration of symptoms or an otherwise desired biological outcome and may be evaluated by improved clinical signs, delayed onset of disease, reduced/elevated levels of lymphocytes and/or antibodies, etc.

Exemplary procedures for delivering an antibacterial agent are described in U.S. Pat. Nos. 6,468,967; 6,852,689; and 5,041,567, issued to Rogers and in PCT patent application number EP94/02552 (publication no. WO 95/05384), the disclosures of which are incorporated herein by reference in their entirety. In one embodiment, one or more compounds of Formula I or pharmaceutical compositions thereof are administered orally, rectally or via injection (intravenous, intramuscular or subcutaneous). In another embodiment, one or more compounds of Formula I or pharmaceutical compositions thereof are administered orally, rectally or via injection (intravenous, intramuscular or subcutaneous) to treat an infection caused by the pathogen *C. difficile*. In another embodiment, one or more compounds of Formula I or pharmaceutical compositions thereof are administered orally to treat an infection caused by the pathogen *C. difficile*. As used herein, the phrases "therapeutically effective dose" and "therapeutically-effective amount" refer to an amount of a compound that prevents the onset, alleviates the symptoms, stops the progression of a bacterial infection, or results in another desired biological outcome such as, e.g., improved clinical signs or reduced/elevated levels of lymphocytes and/or antibodies. The term "treating" is defined as administering, to a subject, a therapeutically-effective amount of one or more compounds both to prevent the occurrence of an infection and to control or eliminate an infection. The term "subject," as used herein, refers to a mammal, a plant, a lower animal, or a cell culture. In one embodiment, a subject is a human or other animal patient in need of antibacterial treatment.

The methods of the present invention comprise administering one or more compounds of Formula I or pharmaceutical compositions thereof to a subject in need thereof in an amount that is efficacious in reducing or eliminating the bacterial infection. The compound may be administered orally, parenterally, by inhalation, topically, rectally, nasally, buccally, vaginally, or by an implanted reservoir, external pump or catheter. The compound may be prepared for ophthalmic or aerosolized uses. The compounds of the present invention can be administered as an aerosol for the treatment of pneumonia or other lung-based infections. In one embodiment, the aerosol delivery vehicle is an anhydrous or dry powder inhaler. One or more compounds of Formula I or pharmaceutical compositions thereof also may be directly injected or administered into an abscess, ventricle or joint. Parenteral administration includes subcutaneous, intravenous, intramuscular, intra-articular, intra-synovial, cisternal, intrathecal, intrahepatic, intralesional and intracranial injection or infusion. In one embodiment, one or more compounds of Formula I are administered intravenously, subcutaneously or orally. In one embodiment for administering one or more compounds according to Formula I to a cell culture, the one or more compounds may be administered in a nutrient medium.

In one embodiment, one or more compounds according to Formula I may be used to treat a subject having a bacterial infection in which the infection is caused or exacerbated by any type of bacteria, such as gram-positive bacteria. In one embodiment, one or more compounds according to Formula I or pharmaceutical compositions thereof are administered to a patient according to the methods of this invention. In another embodiment, the bacterial infection may be caused or exacerbated by gram-positive bacteria. These gram-positive bacteria include, but are not limited to, methicillin-susceptible and methicillin-resistant staphylococci (including *Staphylococcus aureus, S. epidermidis, S. haemolyticus, S. hominis, S. saprophyticus*, and coagulase-negative staphylococci), glycopeptide intermediary-susceptible *S. aureus* (GISA), vancomycin-resistant *Staphylococcus aureus* (VRSA), penicillin-susceptible and penicillin-resistant streptococci (including *Streptococcus pneumoniae, S. pyogenes, S. agalactiae, S. avium, S. bovis, S. lactis, S. sangius* and Streptococci Group C, Streptococci Group G and viridans streptococci), enterococci (including vancomycin-susceptible and vancomycin-resistant strains such as *Enterococcus faecalis* and *E. faecium*), *Clostridium difficile, C. clostridiiforme, C. innocuum, C. perfringens, C. ramosum, Listeria monocytogenes, Corynebacterium jeikeium, Bifidobacterium* spp., *Eubacterium aerofaciens, E. lentum, Lactobacillus acidophilus, L. casei, L. plantarum, Lactococcus* spp., *Leuconostoc* spp., *Pediococcus, Peptostreptococcus anaerobius, P. asaccarolyticus, P. magnus, P. micros, P. prevotii, P. productus, Propionibacterium acnes, Actinomyces* spp., *Moraxella* spp. (including *M. catarrhalis*).

In one embodiment, the compounds of Formula I are as active or more active than daptomycin. Compounds of this embodiment include 3, 4, 5, 6, 7, 9, 10, 11, 14, 16, 17, 18, 19, 20, 21, 22, 23, 25, 26, 27, 28, 32, 33, 34, 35, 36, 37, 38, 39, 42, 43, 48, 49, 50, 51, 52, 53, 54, 55, 57, 58, 61, 62, 63, 64, and 69.

In one embodiment, the compounds of Formula I are unexpectedly more active against bacteria than daptomycin. Compounds that are more effective than daptomycin are, for example, compounds 3, 5, 6, 7, 10, 11, 14, 17, 19, 20, 23, 25, 32, 33, 34, 36, 37, 38, 39, 43, 49, 50, 51, 52, 53, 54, 58, 61, 62, 63, 64, and 69.

In one embodiment, the bacterial infection may be caused or exacerbated by *Clostridium difficile*. Compounds that are useful against *Clostridium difficile* bacteria are, for example, compounds 10, 11, 14, 16, 17, 18, 19, 22, 23, 25, 26, 27, 28, 33, 34, 36, 37, 38, 42, 43, 48, 49, 50, 51, 52, 53, 61, 62, 63, 64, and 69.

Compounds that are particularly useful against *Clostridium difficile* are, for example, compounds 16, 18, 19, 22, 23, 28, 33, 34, 36, 42, 43, 49, 50, and 51.

In another embodiment, the compounds of Formula I are unexpectedly active against bacteria that are resistant to daptomycin, including daptomycin resistant *Staph. aureus* (DRSA), daptomycin resistant *E. faecium* (DREfm) and daptomycin resistance *E. faecalis* (DREfs). Compounds of the invention that are useful against daptomycin resistant strains of bacteria are, for example, compounds 3, 4, 5, 6, 7, 10, 11, 14, 17, 18, 19, 20, 21, 22, 23, 25, 26, 27, 32, 33, 34, 36, 37, 38, 39, 41, 42, 43, 48, 49, 50, 51, 52, 53, 54, 55, 57, 58, 61, 62, 63, 64, and 69.

In one embodiment, compounds of Formula I are active against mutant strains of *Clostridium difficile*, such as, Nucleosome Assembly Protein 1 (NAP-1). Compounds of this embodiment include, for example, compound 49.

Compounds of Formula I that are unexpectedly more active than daptomycin, are useful against *Clostridium difficile*, and are unexpectedly active against bacteria that are resistant to daptomycin are compounds 33 and 49. In addition, compounds 33 and 49 showed excellent results both in vitro and in vivo.

A compound of Formula I that is unexpectedly more active than daptomycin, is useful against *Clostridium difficile*, is unexpectedly active against bacteria that are resistant to daptomycin, and is useful against NAP1 is compound 49. In addition, compound 49 showed excellent results both in vitro and in vivo.

In another embodiment, the antibacterial activity of compounds of Formula I against classically "resistant" strains are comparable to that against classically "susceptible" strains in in vitro experiments. In one embodiment, one or more compounds of Formula I or pharmaceutical compositions thereof are administered according to the methods of this invention to a patient who exhibits a bacterial infection that is resistant to other compounds, including vancomycin or daptomycin. In addition, unlike glycopeptide antibiotics, lipopeptide compounds exhibit rapid, concentration-dependent bactericidal activity against gram-positive organisms. Thus, in one embodiment, one or more compounds of Formula I or pharmaceutical compositions thereof are administered according to the methods of this invention to a patient in need of rapidly acting antibiotic therapy.

The method of the instant invention may be used for any bacterial infection of any organ or tissue in the body. In one, the bacterial infection is caused by gram-positive bacteria. These organs or tissue include, without limitation, skeletal muscle, skin, bloodstream, kidneys, heart, lung and bone. The method of the invention may be used to treat, without limitation, skin and soft tissue infections, bacteremia and urinary tract infections. The method of the invention may be used to treat community acquired respiratory infections, including, without limitation, otitis media, sinusitis, chronic bronchitis and pneumonia, including pneumonia caused by drug-resistant *S. pneumoniae* or *H. influenzae*. The method of the invention also may be used to treat mixed infections that comprise different types of gram-positive bacteria, or which comprise both gram-positive and gram-negative bacteria. These types of infections include intra-abdominal infections and obstetrical/gynecological infections. The method of the invention also may be used to treat an infection including, without limitation, endocarditis, nephritis, septic arthritis, intra-abdominal sepsis, bone and joint infections. and osteomyelitis. The method of the invention may also be used to treat *Clostridium difficile*-associated disease (CDAD). In one embodiment, the method of the invention may be used to treat CDAD that emerges from or is exacerbated by NAP-1. In one embodiment, the method of the invention may be used to treat *C. difficile* associated colitis and *C. difficile* associated diarrhea. In one embodiment, any of the above-described diseases may be treated using lipopeptide compounds according to this invention or pharmaceutical compositions thereof.

The method of the instant invention may also be practiced while concurrently administering one or more other antimicrobial agents, such as antibacterial agents (antibiotics) or antifungal agents. In one aspect, the method may be practiced by administering one or more compounds according to Formula I. In another embodiment, the method may be practiced by administering one or more compounds of Formula I with another lipopeptide compound, such as daptomycin.

Antibacterial agents and classes thereof that may be co-administered with one or more compounds of Formula I include, without limitation, penicillins carbapenems, cephalosporins, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents, trimethoprim pyrimethamine, synthetic antibacterials nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, everninomicin, glycopeptide glycylcycline, ketolides, oxazolidinones, imipenen, amikacin, netilmicin, fosfomycin, gentamicin, ceftriaxone, Ziracin (56-deacetyl-57-demethyl-45-O-de(2-methyl-1-oxopropyl)-12-O-(2,3,6-trideoxy-3-C-methyl-4-O-methyl-3-nitro-alpha-L-arabino-hexopyranosyl)flambamycin), LY333328 (oritavancin), Linezolid (N-[[(5S)-3-[3-fluoro-4-(4-morpholinyl)phenyl]-2-oxo-5-oxazolidinyl]methyl]acetamide), Synercid (dalfopristin-quinupristin), Aztreonam (2-[[(Z)-[1-(2-amino-4-thiazolyl)-2-[[(2S,3S)-2-methyl-4-oxo-1-sulfo-3-azetidinyl]amino]-2-oxoethylidene]amino]oxy]-2-methyl-propanoic acid), Metronidazole (2-methyl-5-nitro-1H-imidazole-1-ethanol), Epiroprim (5-[[3,5-diethoxy-4-(1H-pyrrol-1-yl)phenyl]methyl]-2,4-pyrimidinediamine), OCA-983 (1-[[(2S)-2-amino-3-methyl-1-oxobutyl]amino]-2,5-anhydro-3-S-[(4R,5S,6S)-2-carboxy-6-[(1R)-1-hydroxyethyl]-4-methyl-7-oxo-1-azabicyclo[3.2.0]hept-2-en-3-yl]-1,4-dideoxy-3-thio-D-threo-pentitol), GV-143253 (trinem), Sanfetrinem ((1S,5S, 8aS,8bR)-1,2,5,6,7,8,8a,8b-octahydro-1-[(1R)-1-hydroxyethyl]-5-methoxy-2-oxo-azeto[2,1-a]isoindole-4-carboxylic acid), CS-834 ((4R,5S,6S)-6-[(1R)-1-hydroxyethyl]-4-methyl-7-oxo-3-[[(3R)-5-oxo-3-pyrrolidinyl]thio]-1-azabicyclo[3.2.0]hept-2-ene-2-carboxylic acid (2,2-dimethyl-1-oxopropoxy)methyl ester), Biapenem (6-[[(4R,5S,6S)-2-carboxy-6-[(1R)-1-hydroxyethyl]-4-methyl-7-oxo-1-azabicyclo[3.2.0]hept-2-en-3-yl]thio]-6,7-dihydro-5H-pyrazolo[1,2-a][1,2,4]triazol-4-ium inner salt), KA 159 (stipiamide), Dynemicin A ((1S,4R,4aR,14S,14aS,18Z)-1,4,7,12,13,14-hexahydro-6,8,11-trihydroxy-3-methoxy-1-methyl-7,12-dioxo-4a,14a-epoxy-4,14-[3]hexene[1,5]diynonaphtho[2,3-c]phenanthridine-2-carboxylic acid), DX8739 ((4R,5S,6S)-3-[[(3S,5S)-5-[[4-[(2S)-5-amino-2-hydroxy-1-oxopentyl]-1-piperazinyl]carbonyl]-3-pyrrolidinyl]thio]-6-[(1R)-1-hydroxyethyl]-4-methyl-7-oxo-1-azabicyclo[3.2.0]hept-2-ene-2-carboxylic acid), DU 6681 ((4R,5S,6S)-3-[[(6S)-6,7-dihydro-5H-pyrrolo[1,2-a]imidazol-6-yl]thio]-6-[(1R)-1-hydroxyethyl]-4-methyl-7-oxo-1-azabicyclo[3.2.0]hept-2-ene-2-carboxylic acid), Cefluprenam ((2E)-N-(2-amino-2-oxoethyl)-3-[(6R,7R)-7-[[(2Z)-(5-amino-1,2,4-thiadiazol-3-yl)[(fluoromethoxy)imino]acetyl]amino]-2-carboxy-8-oxo-5-thia-1-azabicyclo[4.2.0]oct-2-en-3-yl]-N-ethyl-N-methyl-2-propen-1-aminium inner salt), ER 35786 ((4R,5S,6S)-6-[(1R)-1-hydroxyethyl]-3-[[(3S,5S)-5-[(R)-hydroxy(3R)-3-pyrrolidinylmethyl]-3-pyrrolidinyl]thio]-4-methyl-7-oxo-1-azabicyclo[3.2.0]hept-2-ene-2-carboxylic acid monohydrochloride), Cefoselis ((6R,7R)-7-[[(2Z)-(2-amino-4-thiazolyl)(methoxy imino)acetyl]amino]-3-[[2,3-dihydro-2-(2-hydroxyethyl)-3-imino-1H-pyrazol-1-yl]methyl]-8-oxo-5-thia-1-azabicyclo[4.2.0]oct-2-ene-2-carboxylic acid), Sanfetrinem celexetil ((1S,5S,8aS,8bR)-1,2,5,6,7,8,8a,8b-octahydro-1-[(1R)-1-hydroxyethyl]-5-methoxy-2-oxo-azeto[2,1-a]isoindole-4-carboxylic acid 1-[(cyclohexyloxy)carbonyl]oxy]ethyl ester), Cefpirome (1-[[(6R,7R)-7-[[(2Z)-(2-amino-4-thiazolyl)(methoxyimino)acetyl]amino]-2-carboxy-8-oxo-5-thia-1-azabicyclo[4.2.0]oct-2-en-3-yl]methyl]-6,7-dihydro-5H-cyclopenta[b]pyridinium inner salt), HMR-3647 (3-de[(2,6-dideoxy-3-C-methyl-3-O-methyl-alpha-L-ribo-hexopyranosyl)oxy]-11,12-dideoxy-6-β-methyl-3-oxo-12,11-[oxycarbonyl[[4-[4-(3-pyridinyl)-1H-imidazol-1-yl]butyl]imino]]-erythromycin), RU-59863 (C-7 catechol substituted cephalosporin), KP 736 ((6R,7R)-7-[[(2Z)-(2-amino-4-thiazolyl)[[(1,4-dihydro-1,5-dihydroxy-4-oxo-2-pyridinyl)methoxy]imino]acetyl]amino]-8-oxo-3-[(1,2,3-thiadiazol-5-ylthio)methyl]-5-thia-1-azabicyclo[4.2.0]oct-2-ene-2-carboxylic acid disodium salt), Rifalazil (1',4-didehydro-1-deoxy-1,4-dihydro-3'-hydroxy-5'-[4-(2-methylpropyl)-1-piperazinyl]-1-oxo-rifamycin VIII), MEN 10700 ((5R,6S)-3-[[(2-amino-2-oxoethyl)methylamino]methyl]-6-[(1R)-1-hydroxyethyl]-7-oxo-4-thia-1-azabicyclo[3.2.0]hept-2-ene-2-carboxylic acid), Lenapenem ((4R,5S,6S)-6-[(1R)-1-hydroxyethyl]-3-[[(3S,5S)-5-[(1R)-1-hydroxy-3-(methylamino)propyl]-3-pyrrolidinyl]thio]-4-methyl-7-oxo-1-azabicyclo[3.2.0]hept-2-ene-2-carboxylic acid), BO 2502A ((4R,5S,6S)-3-[(2S,3'S,4S)-[2,3'-bipyrrolidin]-4-ylthio]-6-[(1R)-1-hydroxyethyl]-4-methyl-7-oxo-1-azabicyclo[3.2.0]hept-2-ene-2-carboxylic acid), NE-1530 (3'-sialyllacto-N-neotetraose), K130 (5-[[4-[3-[[4-[(4-aminophenyl)sulfonyl]phenyl]amino]propoxy]-3,5-dimethoxyphenyl]methyl]-2,4-pyrimidinediamine), PD 138312 ((R)-7-[3-(1-amino-1-methylethyl)-1-pyrrolidinyl]-1-cyclopropyl-6-fluoro-1,4-dihydro-4-oxo-1,8-naphthyridine-3-carboxylic acid), PD 140248 (7-[(3R)-3-[(1S)-1-aminoethyl]-1-pyrrolidinyl]-1-(2,4-difluorophenyl)-6-fluoro-1,4-dihydro-4-oxo-1,8-naphthyridine-3-carboxylic acid), CP 111905 (5-deoxy-5-[[(2E)-3-[3-hydroxy-4-(2-propenyloxy)phenyl]-2-methyl-1-oxo-2-propenyl]amino]-1,2-O-methylene-D-neo-inositol), Sulopenem ((5R,6S)-6-[(1R)-1-hydroxyethyl]-7-oxo-3-[[(1R,3S)-tetrahydro-1-oxido-3-thienyl]thio]-4-thia-1-azabicyclo[3.2.0]hept-2-ene-2-carboxylic acid), ritipenam acoxyl ((5R,6R)-3-[[(aminocarbonyl)oxy]methyl]-6-[(1R)-1-hydroxyethyl]-7-oxo-4-thia-1-azabicyclo[3.2.0]hept-2-ene-2-carboxylic acid (acetyloxy)methyl ester), RO-65-5788 ((6R,7R)-7-[[(2Z)-(5-amino-1,2,4-thiadiazol-3-yl)(hydroxyimino)acetyl]amino]-3-[(E)-[(3R)-1'-[[(5-methyl-2-oxo-1,3-dioxol-4-yl)methoxy]carbonyl]-2-oxo[1,3'-bipyrrolidin]-3-ylidene]methyl]-8-oxo-5-thia-1-azabicyclo[4.2.0]oct-2-ene-2-carboxylic acid monosodium salt), Sch-40832 (N-[[48-[1-[[2,6-dideoxy-3-O-(2,6-dideoxy-D-arabino-hexopyranosyl)-D-arabino-hexopyranosyl]oxy]ethyl]-15-ethylidene-1,3a,4,5,10,11,12,13,14,15,19,20,21,22,28,29,41,42-octadecahydro-41-hydroxy-12,45-bis(1-hydroxyethyl)-1-(hydroxymethyl)-22-(1-hydroxy-1-methylpropyl)-36-methyl-51,54,57-tris(methylene)-3-(methylthio)-10,13,20,27,38,49,52,55,58-nonaoxo-18H,27H-5a,29-(iminoethaniminoethanimino ethaniminoethanimino[7,2]quinolinomethanoxy methano)-9, 6:19, 16:26, 23:33,30-tetranitrilo-16H,33aH-imidazo[1'5':1,6]pyrido[3,2-m][1,11,17,24,4,7,20,27]tetrathiatetraazacyclotriacontin-1-yl]carbonyl]-2,3-didehydroalanyl-2,3-didehydro-alanine methyl ester stereoisomer), micacocidin A ((OC-6-26-A)-[(4S)-2-[(2S)-2-[(2R,4R)-2-[(4R)-4,5-dihydro-2-[2-(hydroxy-.kappa.O)-6-pentylphenyl]-4-thiazolyl-.kappa.N3]-3-methyl-4-thiazolidinyl-.kappa.N3]-2-(hydroxy-.kappa.O)-1,1-dimethylethyl]-4,5-dihydro-4-methyl-4-thiazolecarboxylato(2-)-.kappa.N3, .kappa.O4]-Zinc), SR-15402 ((1S,5S,8aS,8bR)-1,2,5,6,7,8,8a,8b-octahydro-1-[(1R)-1-hydroxyethyl]-2-oxo-5-[(3S)-3-pyrrolidinylthio]-azeto[2,1-a]isoindole-4-carboxylic acid), TOC 39 (1-(2-amino-2-oxoethyl)-4-[[(1E)-2-[(6R,7R)-7-[[(2Z)-(2-amino-4-thiazolyl)(hydroxyimino)acetyl]amino]-2-carboxy-8-oxo-5-thia-1-azabicyclo[4.2.0]oct-2-en-3-yl]ethenyl]thio]-pyridinium inner salt), carumonam ([[(Z)-[2-[[(2S,3S)-2-

[[(aminocarbonyl)oxy]methyl]-4-oxo-1-sulfo-3-azetidinyl]amino]-1-(2-amino-4-thiazolyl)-2-oxoethylidene]amino]oxy]-acetic acid), Cefozopran (1-[[(6R,7R)-7-[[(2Z)-(5-amino-1,2,4-thiadiazol-3-yl)(methoxy imino)acetyl]amino]-2-carboxy-8-oxo-5-thia-1-azabicyclo[4.2.0]oct-2-en-3-yl]methyl]-imidazo[1,2-b]pyridazinium inner salt), Cefetamet pivoxil ((6R,7R)-7-[[(2Z)-(2-amino-4-thiazolyl)(methoxy imino)acetyl]amino]-3-methyl-8-oxo-5-thia-1-azabicyclo[4.2.0]oct-2-ene-2-carboxylic acid (2,2-dimethyl-1-oxopropoxy)methyl ester), and T 3811 (des-F(6)-quinolone).

Antifungal agents that may be co-administered with one or more compounds according to the invention include, without limitation, caspofungen, voriconazole, sertaconazole, IB-367, FK-463, LY-303366, Sch-56592, sitafloxacin, DB-289 polyenes, such as amphotericin, nystatin, primaricin; azoles, such as fluconazole, itraconazole, and ketoconazole; allylamines, such as naftifine and terbinafine; and anti-metabolites such as flucytosine. Other antifungal agents include without limitation, those disclosed in Fostel, et al., 2000, *Drug Discovery Today* 5: 25-32, herein incorporated by reference. Fostel et al. discloses antifungal compounds including corynecandin, Mer-WF3010, fusacandins, artrichitin/LL 15G256, sordarins, cispentacin, azoxybacillin, aureobasidin and khafrefungin Actual dosage levels of active ingredients in the pharmaceutical compositions of one or more compounds according to Formula I may be varied so as to obtain a therapeutically effective amount of the active compound(s) to achieve the desired therapeutic response for a particular patient, compositions, and mode of administration. The effective amount can be determined as described herein. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans.

The method comprises administering to the subject an effective dose of one or more compounds of Formula I. An effective dose is generally between 125 mg/day to 1000 mg/day. In one embodiment, an effective dose is from about 0.1 to about 100 mg/kg of one or more compounds of Formula I or pharmaceutically acceptable salts thereof. In one embodiment, the dose is from about 0.1 to about 50 mg/kg of one or more compounds of Formula I or pharmaceutically acceptable salts thereof. In another embodiment, the dose is from about 1 to about 25 mg/kg of one or more compounds of Formula I or pharmaceutically acceptable salts thereof. In another embodiment, the dose is from about 1 to about 12 mg/kg of one or more compounds of Formula I. In another embodiment, the dose is about 1, 2, 3, 4, 5, 6, 7, 8, 9, 10, 11, or 12 mg/kg of one or more compounds of Formula I. An effective dose for cell culture is usually between about 0.1 and about 1000 μg/mL. In one embodiment, the effect dose for cell culture is between about 0.1 and about 200 μg/mL.

Generally dosage levels of about 0.1 μg/kg to about 50 mg/kg, such as a level ranging from about 5 to about 20 mg of active compound per kilogram of body weight per day, can be administered topically, orally or intravenously to a mammalian patient. Other dosage levels range from about 1 μg/kg to about 20 mg/kg, from about 1 μg/kg to about 10 mg/kg, from about 1 μg/kg to about 1 mg/kg, from 10 μg/kg to 1 mg/kg, from about 10 μg/kg to about 100 μg/kg, from about 100 μg to about 1 mg/kg, and from about 500 μg/kg to about 5 mg/kg per day. If desired, the effective daily dose may be divided into multiple doses for purposes of administration, e.g., two, three or four separate doses per day. In one embodiment, the pharmaceutical composition can be administered once per day.

One or more compounds of Formula I may also be administered in the diet or feed of a patient or animal. If administered as part of a total dietary intake, the amount of compound employed can be less than 1% by weight of the diet, such as no more than 0.5% by weight. The diet for animals can be normal foodstuffs to which the compound can be added or it can be added to a premix.

One or more compounds of Formula I can be administered as a single daily dose or in multiple doses per day. In one embodiment, one or more compounds of Formula I are administered as a single dose per day. In another embodiment, one or more compounds of Formula I are administered as two equal doses per day. In another embodiment, the compounds of Formula I are administered in three equal doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the compound and the microorganism or microorganisms involved in the infection. The treatment regimen for one type of infection may differ greatly from the treatment regimen of another infection. For example, one type of infection may require administration via intravenous administration once daily, while another infection may require a treatment regimen of multiple dosing orally. A method of administration of daptomycin, another member of the lipopeptide compound class, to a patient is disclosed in U.S. Pat. Nos. 6,468,967 and 6,852,689.

One or more compounds of Formula I may be administered according to this method until the bacterial infection is eradicated or reduced. In one embodiment, one or more compounds of Formula I are administered for a period of time from 3 days to 6 months. In another embodiment, one or more compounds of Formula I are administered for 7 to 56 days. In another embodiment, one or more compounds of Formula I are administered for 7 to 28 days. In a further embodiment, one or more compounds of Formula I are administered for 7 to 14 days. Compounds of the present invention may be administered for a longer or shorter time period if it is so desired.

The embodiments described herein provide compounds of Formula I that are novel and active against gram-positive bacteria. Other embodiments described herein provide novel compounds of Formula I that show increased activity against *Clostridium difficile*. Further embodiments described herein provide novel compounds of Formula I that show unexpected activity against bacteria that are resistant to daptomycin.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

EXAMPLES

In order that this invention may be more fully understood, the following examples are set forth. These examples are for illustrative purposes only and are not to be construed as limiting the scope of the invention in any way.

In the examples below, the following abbreviations have the following meanings unless otherwise indicated. Abbreviations not defined below have their generally accepted meaning.

BOC=tert-butoxycarbonyl
CFU=colony-forming units
DCM=dichloromethane
IPA=isopropanol
DIPEA=diisopropylethylamine
DMF=dimethylformamide
DMSO=dimethyl sulfoxide
EtOAc=ethyl acetate
HOBT=1-hydroxy benzotriazole
HCl=hydrochloric acid
HPLC=High performance liquid chromatography
MIC=Minimum inhibitory concentration
MS=Mass spectrometry
THF=tetrahydrofuran
TFA=trifluoroacetic acid
TLC=thin layer chromatography
TTF=Tangential flow filtration
WFI=Water for injection, which is purified by distillation or reverse osmosis

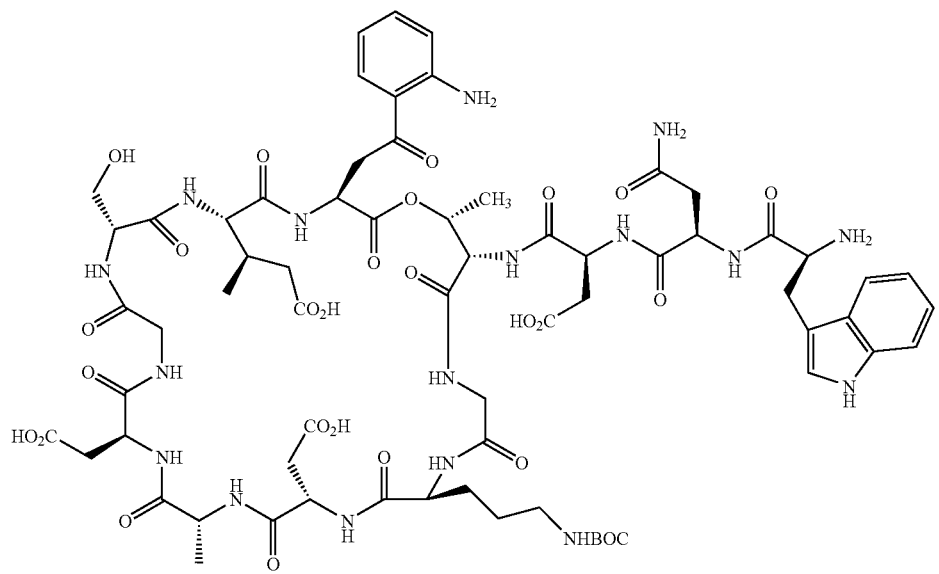

Decylated BOC-protected daptomycin

All temperatures reported in the following examples are in degree Celsius (° C.) unless otherwise indicated. Also, unless noted otherwise, reagents, starting materials and solvents were purchased from commercial suppliers (such as Aldrich, Fluka, Sigma and the like) and were used without further purification. Deacylated BOC-protected daptomycin was prepared based on the method described in U.S. Pat. No. 6,911,525B2.

Final products were typically purified by reverse phase HPLC using a C8 column.

Analytical HPLC conditions for monitoring the reactions were as follows: Waters Alliance HPLC system with SunFire™ C8 (5 um, 4.6×150 mm) column using an increasing gradient (e.g., 10 to 90% B in A in 20 min; A=0.01% TFA in water; B=0.01% TFA in acetonitrile).

Analytical HPLC conditions for purity tests were as follows: Waters Alliance HPLC system with SunFire™ C8 (5 um, 4.6×150 mm) column using an increasing gradient (e.g., 30 to 50% B in A in 20 min; A=0.01% TFA in water; B=0.01% TFA in acetonitrile).

Preparative HPLC conditions: Varian Prep HPLC system with SunFire™ prep C8 OBDTM (10 μm, 19×250 mm) column using an increasing gradient (e.g., 25 to 45% B in A in 20 min; A=0.01% TFA in water; B=0.01% TFA in acetonitrile).

Compounds of the present invention can be prepared according to the procedures described in U.S. Pat. No. 6,911,525B2, which is incorporated by reference in its entirety, and/or as detailed below:

Reaction Scheme I
Deacylated BOC-protected daptomycin →(Step 1)
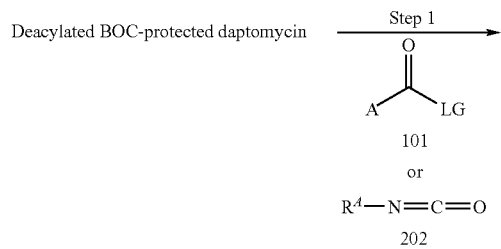
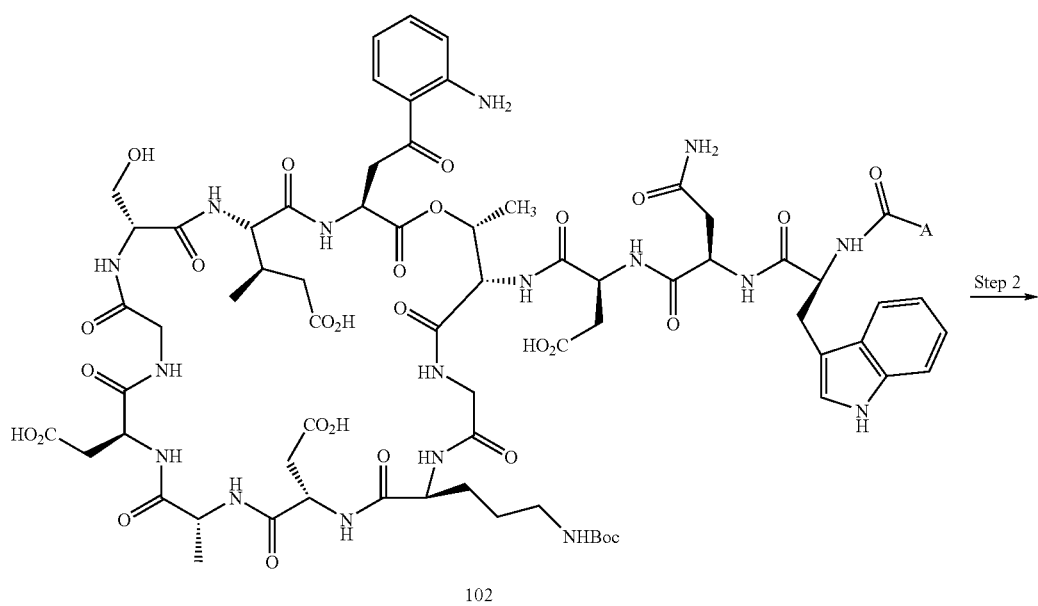
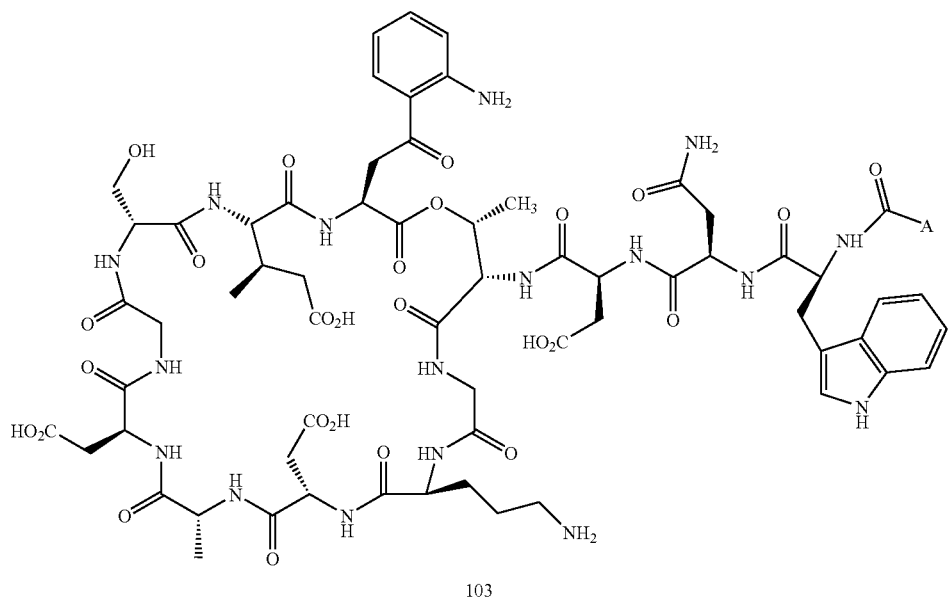

Referring to Reaction Scheme 1, Step 1, Deacylated BOC-protected daptomycin (see U.S. Pat. No. 6,911,525B2) is treated with a modifying agent selected from compounds having the formulae 101, wherein LG is an appropriate leaving group, or 202. The reaction of an amine with modifying agents, as defined herein, is well known to those skilled in the art. For example, treatment of Deacylated BOC-protected daptomycin with an activated ester, lactone or acid chloride, followed by removal of the protecting group (Step 2), yields compounds of the present invention wherein A is alkyl, alkenyl, cylcoalkyl, aryl, or heteroaryl. Alternatively, treatment of Deacylated BOC-protected daptomycin with an isocyanate, such as a compound having the formula 202, followed by removal of the protecting group (Step 2), provides compounds of Formula I wherein A is NHR$^A$.

In one embodiment, the activated ester is a pentafluorophenyl ester (PFP-ester). Pentafluorophenyl (PFP) esters were prepared by treating a carboxylic acid with pentafluorophenol and an acylating agent such as, but not limited to, dicyclohexylcarbodiimide (DCC) in solvent such as dichloromethane (Synthesis, 2007, 23, 3731-3735).

Acyl chlorides were prepared by treating a carboxylic acid with a reagent such as, but not limited to, thionyl chloride or oxalyl chloride with catalytic DMF, in solvent such as dichloromethane.

Preparation of compounds of Formula (I) where R is

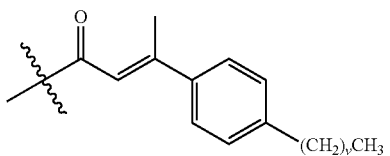

Example 1

Preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (49)

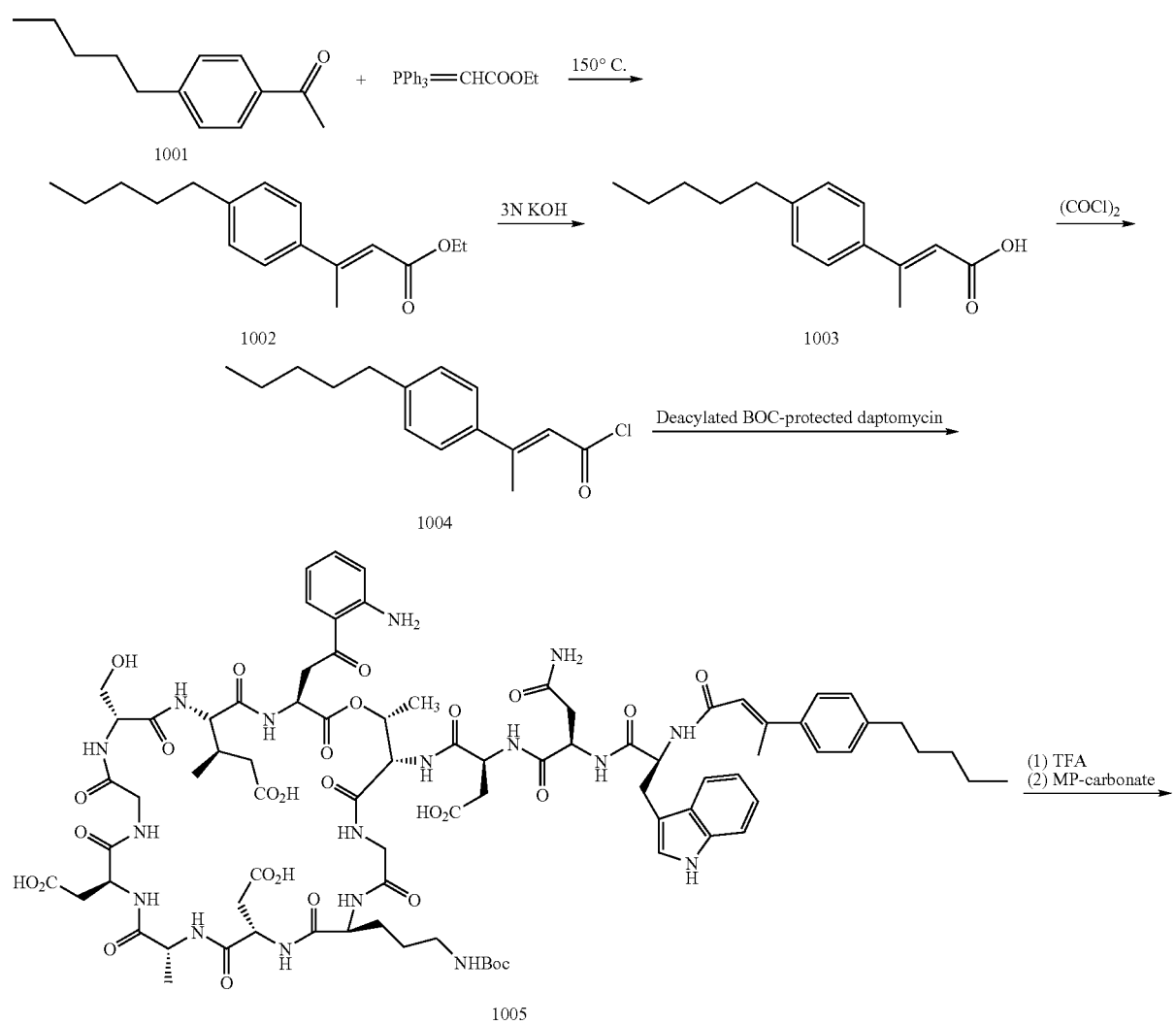

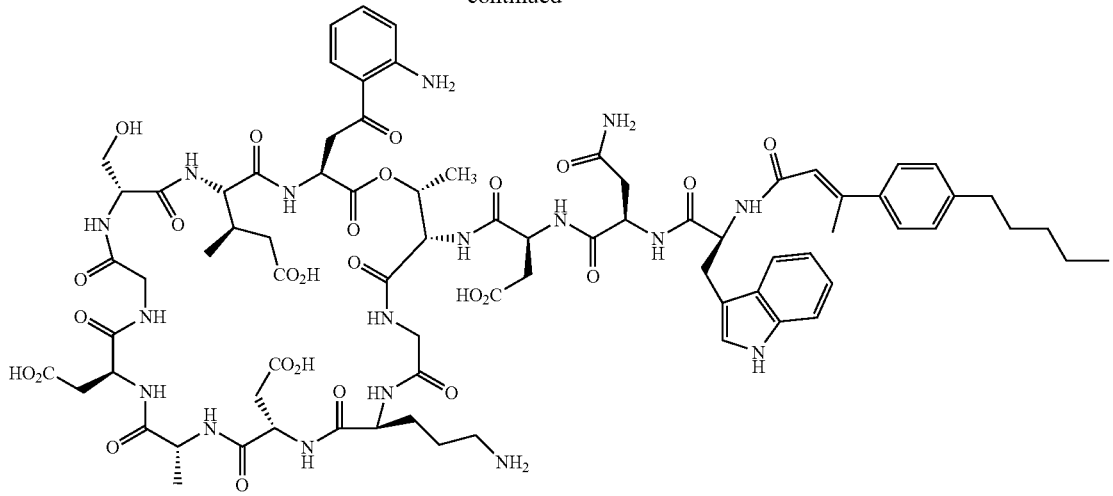

49

Step 1: Preparation of (E)-ethyl 3-(4-pentylphenyl) but-2-enoate (1002)

A mixture of commercially available 1-(4-pentylphenyl) ethanone (5 g, 26.3 mmol) and (ethoxycarbonylmethylene)-triphenylphosphorane (18.3 g, 52.5 mmol) was stirred at 150° C. for 48 hours under a nitrogen atmosphere. The reaction mixture was cooled to ambient temperature and diluted with ethyl acetate (50 mL) and petroleum ether (200 mL). The suspension was filtered through a fritted funnel. The concentrated filtrate was purified by flash column chromatography with silica gel (petroleum ether:ethyl acetate=80:1) to give the title compound (1.6 g) having the following physical data: $^1$H NMR (300 MHz, δ, $CDCl_3$) 0.90 (br, 3H), 1.36 (br, 7), 1.63 (br, 2H), 2.58 (s, 3H), 2.63 (br, 2H), 4.22 (q, 2H), 6.15 (s, 1H), 7.20 (d, 2H), 7.41 (d, 2H).

Step 2: Preparation of (E)-3-(4-pentylphenyl) but-2-enoic acid (1003)

A solution of compound 1002 (1.5 g, 5.77 mmol) in ethanol (50 mL) and 3N potassium hydroxide (25 mL) was stirred at 45° C. for 3 hours. The reaction mixture was concentrated and the resulting residue was diluted with water (50 mL). The aqueous solution was acidified to pH 2 with 1N hydrochloric acid and extracted with EtOAc (2×30 mL). The combined organic layers were dried with anhydrous sodium sulfate, filtered and concentrated. The residue was purified by flash column chromatography (silica gel, petroleum ether:ethyl acetate=10:1) to afford the title compound (0.95 g) having the following physical data: $^1$H NMR (300 MHz, δ, CDCl3) 0.90 (br, 3H), 1.33 (br, 4H), 1.62 (br, 2H), 2.60 (br, 5H), 6.18 (s, 1H), 7.18 (d, 2H), 7.42 (d, 2H).

Step 3: Preparation of (E)-3-(4-pentylphenyl)but-2-enoyl chloride (1004)

Oxalyl chloride (3.2 mL, 36.60 mmol) and DMF (50 µL) were added drop wise to a solution of compound 1003 (5.0 g, 21.52 mmol) in dichloromethane (100 mL) at 0° C. The reaction solution was warmed up to room temperature and stirred for 4 hours. The reaction mixture was concentrated in vacuum and the residue was dried under hi-vacuum for 3 hours. The crude product was used in the next step without further purification.

Step 4: Preparation of N-{1-[(E)-3-(4-pentylphenyl) but-2-enoyl]}-L-tryptophyl-D-asparaginyl-L-α-aspartyl-L-threonylglycyl-L-[(N-tert-butoxycarbonyl)-ornithyl]-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (1005).

Deacylated BOC-protected daptomycin (3.50 g, 2.23 mmol) and sodium bicarbonate (1.13 g, 61.0 mmol) were dissolved in THF (130 mL) and water (50 mL). The deacylated BOC-protected daptomycin sodium bicarbonate solution was cooled to 0° C. and a solution of compound 1004 (1.96 g, 7.82 mmol) in THF (20 mL) was then introduced. The reaction mixture was warmed to room temperature and stirred for 4 hours. The mixture was concentrated in vacuum to remove THF. The remaining aqueous solution was loaded on a C18 flash chromatography column (35 mm×300 mm, Bond-esil HF C18 resin purchased from Varian). The column was first washed with water to remove salt and then with methanol to wash out product. Crude compound 1005 (3.46 g) was afforded as a white solid after removal of methanol. MS m/z 1780.8 $(M+H)^+$.

Steps 5-6: Preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (49).

TFA (10 mL) was added to a solution of compound 1005 (3.46 g) in DCM (50 mL) at room temperature. The reaction mixture was stirred vigorously for 45 minutes and added slowly to vigorously stirring diethyl ether (100 mL). The resulting yellow precipitation was collected by filtration. The crude product was purified by Preparative HPLC to afford the TFA salt of compound 6 (0.75 g). MP carbonate resin (purchased from Biotage) was added to the solution of compound 6 TFA salt (0.70 g, 0.39 mmol) in anhydrous methanol (30.0 mL). The mixture was stirred at room temperature for 4 hours. The resins were removed by filtration and rinsed with methanol. The methanol solution was concentrated under vacuum to give product as off-white solid (408 mg). MS m/z 1680.7 $(M+H)^+$.

Example 1b

Alternative preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (49).

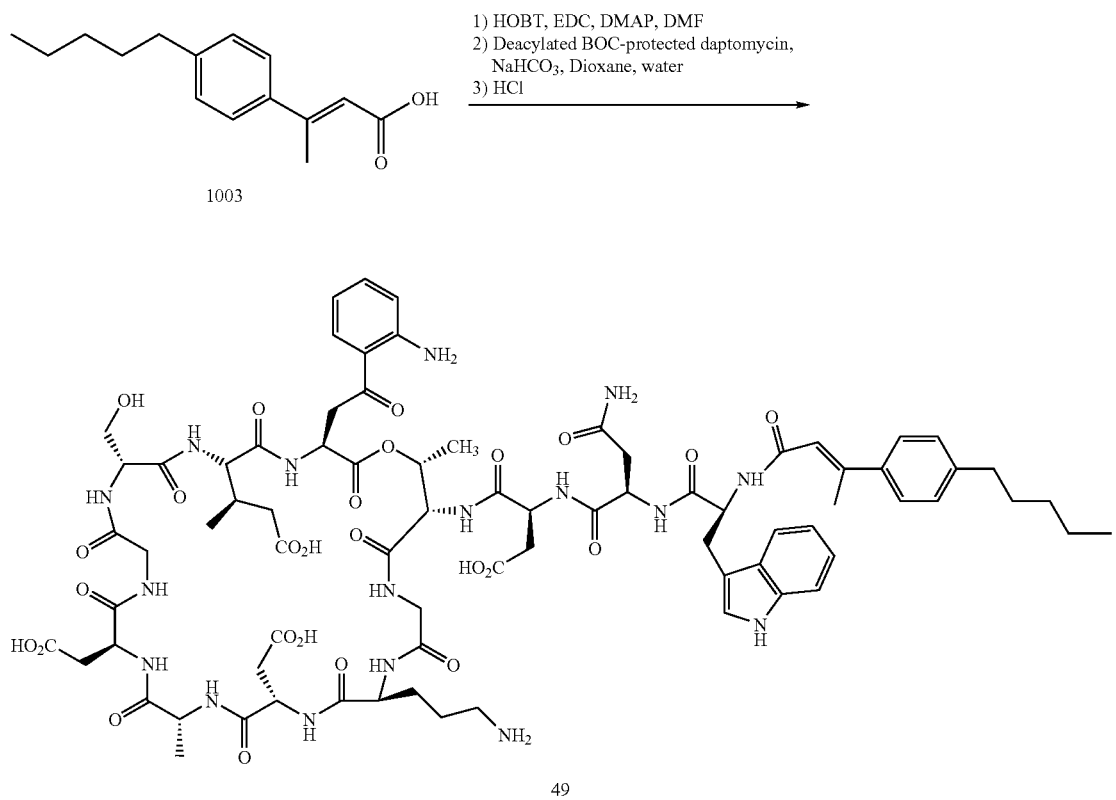

A solution of (E)-3-(4-pentylphenyl)but-2-enoic acid (1100 g, 4.73 mol), N-Ethyl-N'-(3-dimethylaminopropyl)carbodiimide hydrochloride (907 g, 4.73 mol), HOBT (640 g, 4.73 mol) and 4-(dimethylamino)pyridine (22 g, 0.18 mol) in DMF (11 L) was stirred at room temperature for 4 hours at which point the activation of the (E)-3-(4-pentylphenyl)but-2-enoic acid was deemed complete by HPLC. This reaction mixture was added to a suspension of Deacylated BOC-protected daptomycin (2600 g, 1.66 mol), sodium bicarbonate (804 g, 9.57 mol) in water (11.25 L) and 1,4-dioxane (33.75 L). The mixture was stirred at room temperature for 2.5 hours at which time HPLC indicated complete consumption of Deacylated BOC-protected daptomycin. The reaction mixture was diluted with water (22.5 L) and cooled with an ice bath. Concentrated hydrochloric acid (5.25 L) was added while maintaining the internal temperature below 30° C. After the addition, the solution was stirred at room temperature for 5 days at which time HPLC indicated complete consumption of the Boc protected intermediate.

The reaction mixture was washed with methyl tert-butyl ether (90 L then approximately 60 L then approximately 45 L then approximately 45 L) to remove 1,4-dioxane. The remaining solution (approximately 44 L) was adjusted to pH 2.69 with 2N sodium hydroxide (11.3 L) and water (53.4 L). This material was processed by Tangential Flow Filtration (TTF) with a 1K membrane until the total volume was reduced to 54 L. Water (120 L) was added in two portions and the solution was concentrated to 52 L by continued TTF. The aqueous solution (30 L of 52 L) was purified by chromatography using the following protocol: The aqueous solution was brought to three times of its volume (30 L→90 L) with 20% IPA in aqueous ammonium acetate solution (50 mM). The diluted solution was applied to a 38 L HP20SS resin column at 1.5 L/min. The column was eluted with IPA solution in aqueous 50 mM ammonium acetate (25%→30%→>35%, 60 L each concentration). Fractions (approximately 11 L) were collected and analyzed by HPLC. The fractions with HPLC purity less than 80% were combined and purified again using the same method. The key fractions from both chromatographic separations (with HPLC purity >80%) were combined and acidified with concentrated HCl to pH 2-3. The resulting solution was desalted on an ion exchange column (HP20SS resin, 16 L) which was eluted with WFI (until conductivity=4.8 µS) followed by IPA in WFI (36 L 10%→40 L 60%). The yellow band which was eluted with 60% IPA (approximately 19 L) was collected, adjusted to pH 2-3 with concentrated HCl and lyophilized to yield 636.5 g of Compound 49 (HPLC purity of 87.0%). MS m/z 1680.7 (M+H)+.

Example 1c

Preparation of N-{1-[(E)-3-(4-hexylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (50).

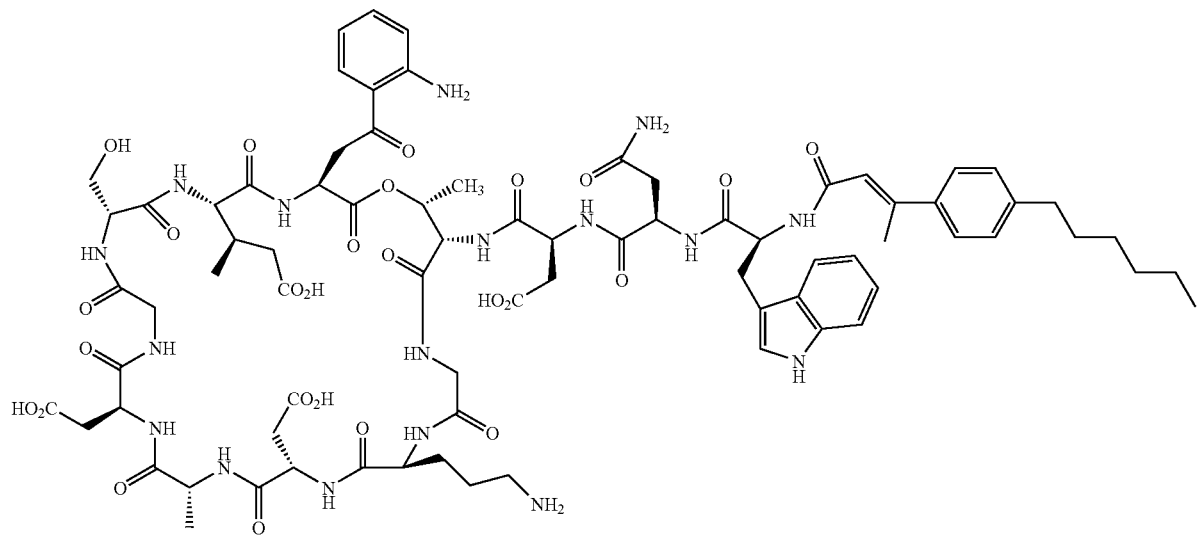

50

The above compound was prepared in a similar manner as described in steps 1-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 1-(4-hexylphenyl)ethanone was used in the place of 1-(4-pentylphenyl)ethanone (in step 1). MS m/z 1694.8 (M+H)$^+$.

Example 1d

Preparation of N-{1-[(E)-3-(4-butylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (48)

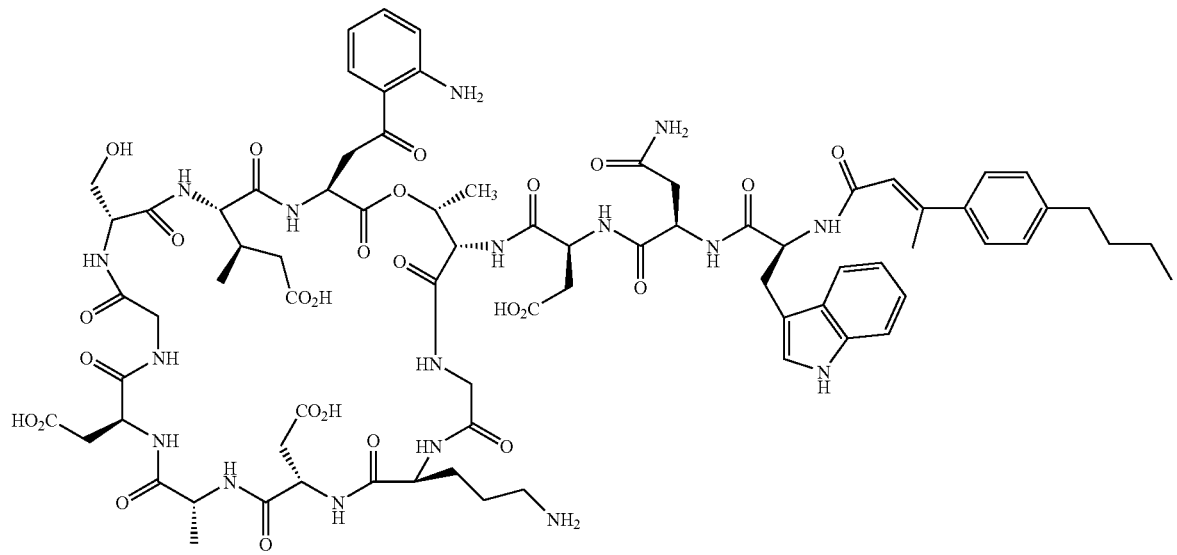

48

The above compound was prepared in a similar manner as described in steps 1-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 1-(4-butylphenyl)ethanone was used in the place of 1-(4-pentylphenyl)ethanone (in step 1). MS m/z 1666.8 (M+H)⁺.

Preparation of compounds of Formula (I) wherein R is

Example 2

Preparation of N-(4-heptylbenzoyl)-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (33)

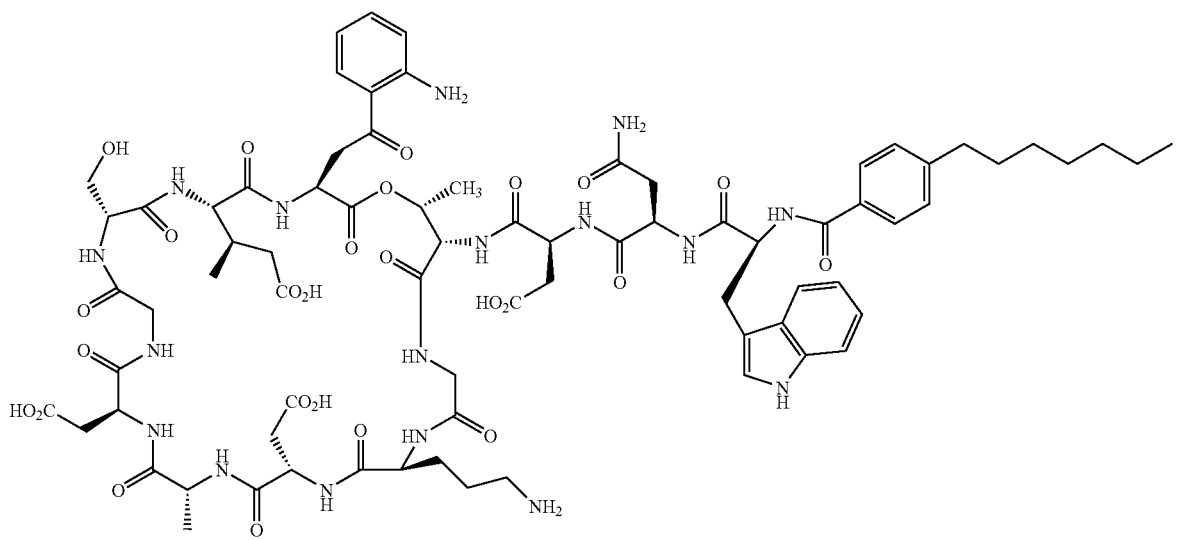

33

The above compound was prepared in a similar manner as described in steps 4-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 4-heptylbenzoyl chloride was used in the place of (E)-3-(4-pentylphenyl)but-2-enoyl chloride. MS m/z 1668.8 (M+H)⁺.

Example 2b

Preparation of N-(4-octylbenzoyl)-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (34)

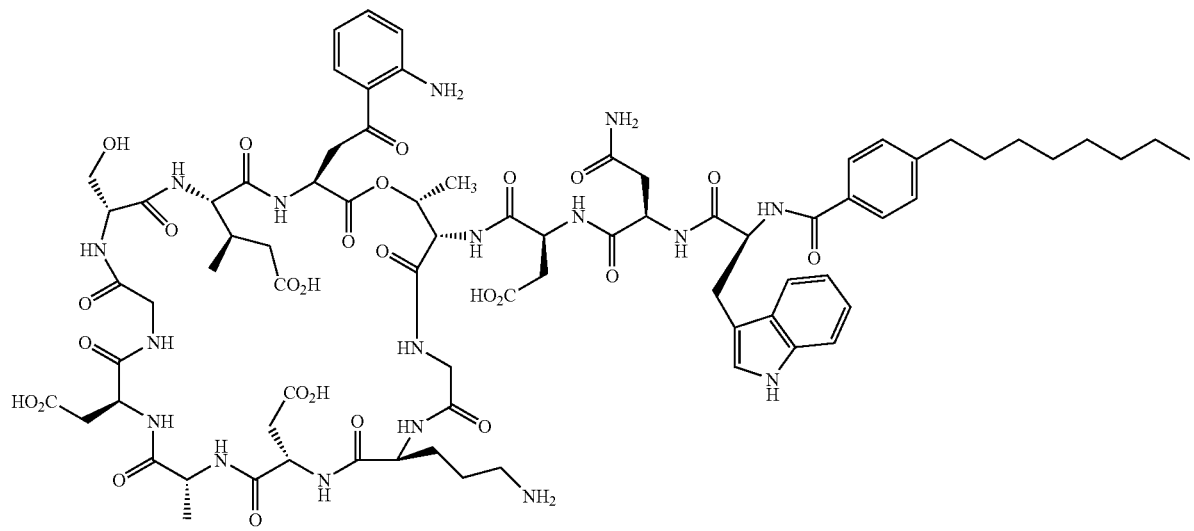

34

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 4-octylbenzoic acid was used in the place of (E)-3-(4-pentylphenyl)but-2-enoic acid. MS m/z 1682.8 (M+H)$^+$.

Preparation of compounds of Formula (I) wherein R is

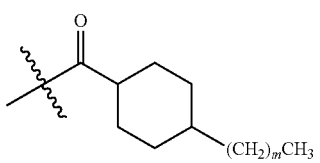

Example 3

Preparation of N-(trans-4-pentylcyclohexanecarbonyl-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (16)

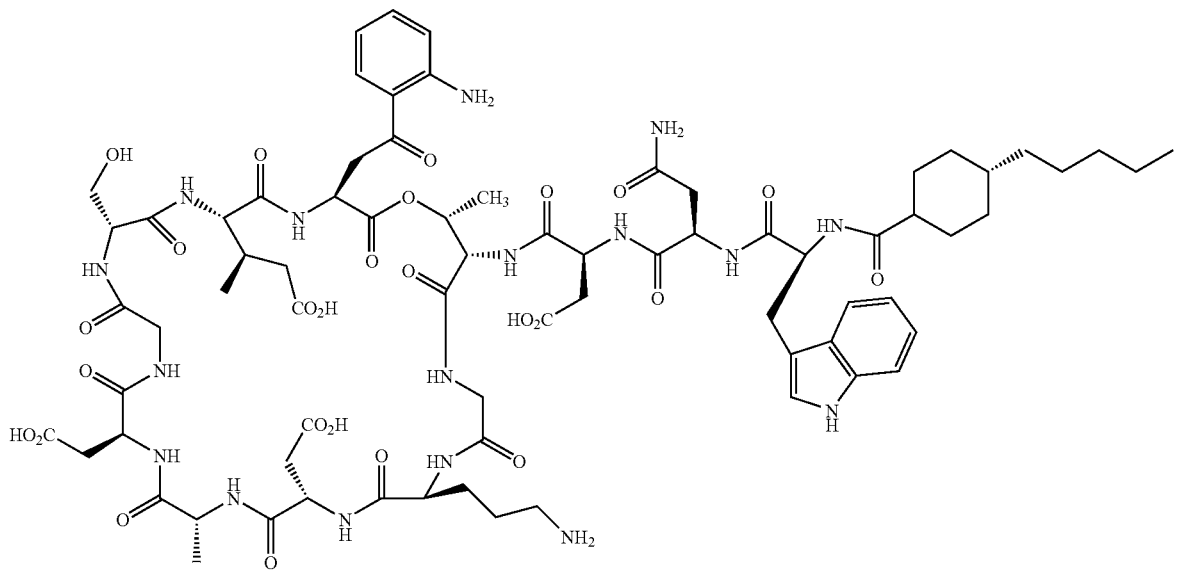

16

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available Trans-4-pentylcyclohexane-carboxylic acid was used in the place of (E)-3-(4-pentylphenyl)but-2-enoic acid. MS m/z 1646.7 (M+H)+.

Preparation of compounds of Formula (I) wherein R is

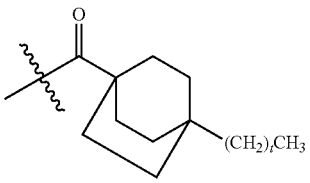

Example 4

Preparation of N-(4-pentylbicyclo[2.2.2]octane-1-carbonyl)-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (22)

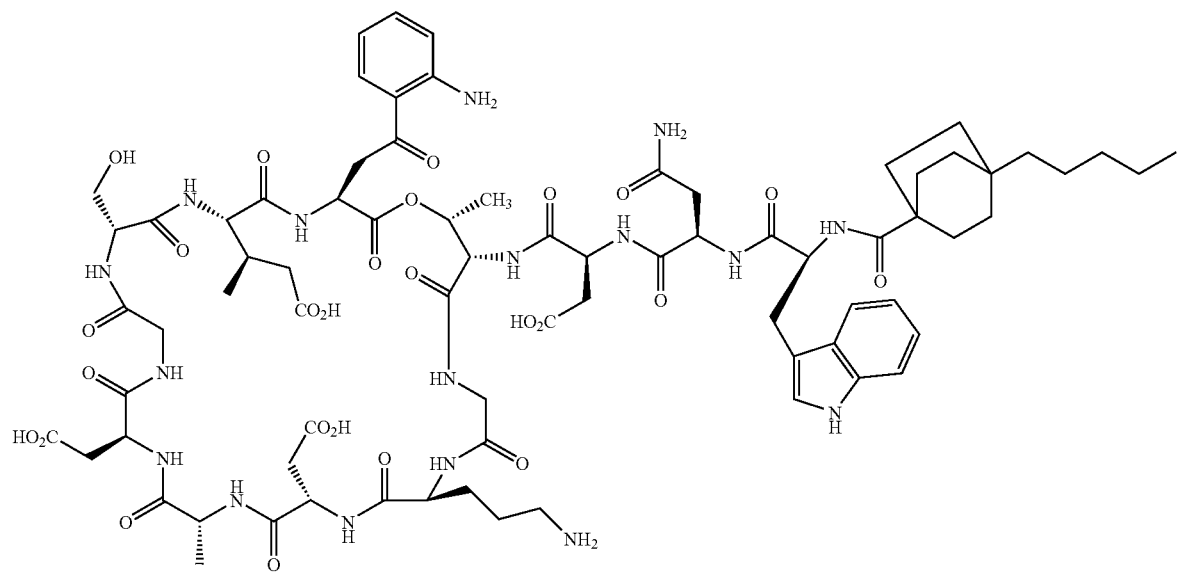

22

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 4-pentylbicyclo[2.2.2]octane-1-carboxylic acid was used in the place of (E)-3-(4-pentylphenyl)but-2-enoic acid. MS m/z 1672.7 (M+H)$^+$.

Preparation of compounds of Formula (I) wherein R is

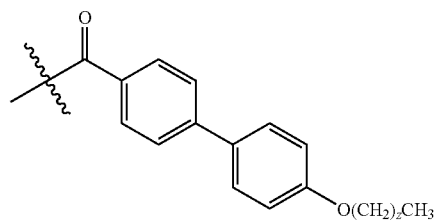

Example 5

Preparation of N4-[4'-(pentyloxy)biphenyl-4-carbonyl]-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (61)

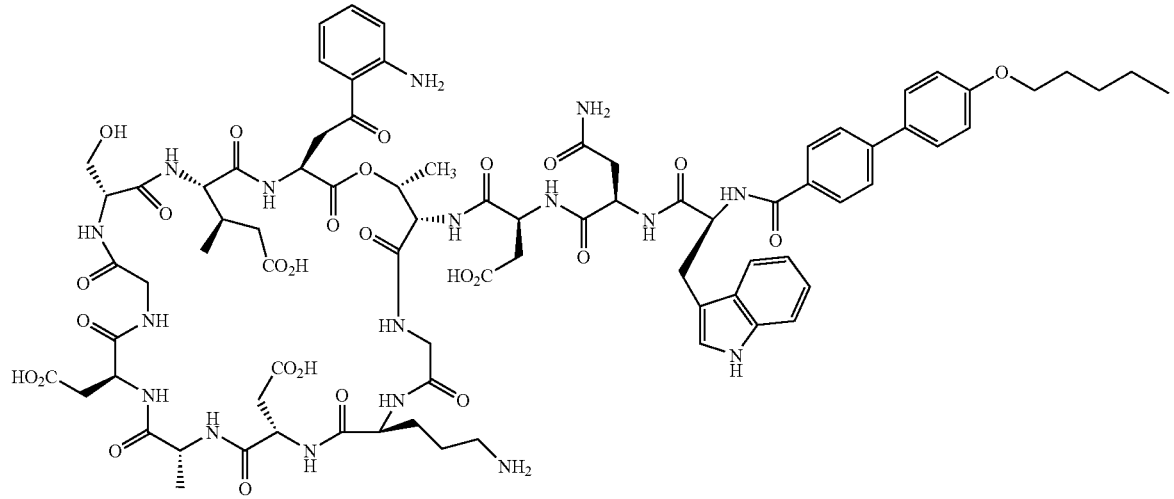

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 4'-(pentyloxy)biphenyl-4-carboxylic acid was used in the place of (E)-3-(4-pentylphenyl)but-2-enoic acid. MS m/z 1732.8 (M+H)+.

Preparation of compounds of Formula (I) wherein R is

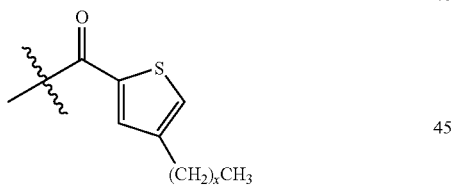

Example 6

Preparation of N-(4-heptylthiophene-2-carbonyl)-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (43)

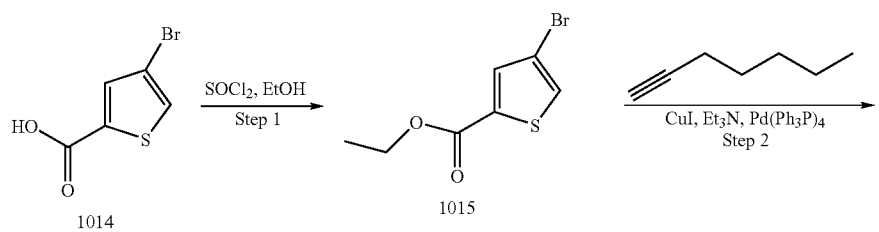

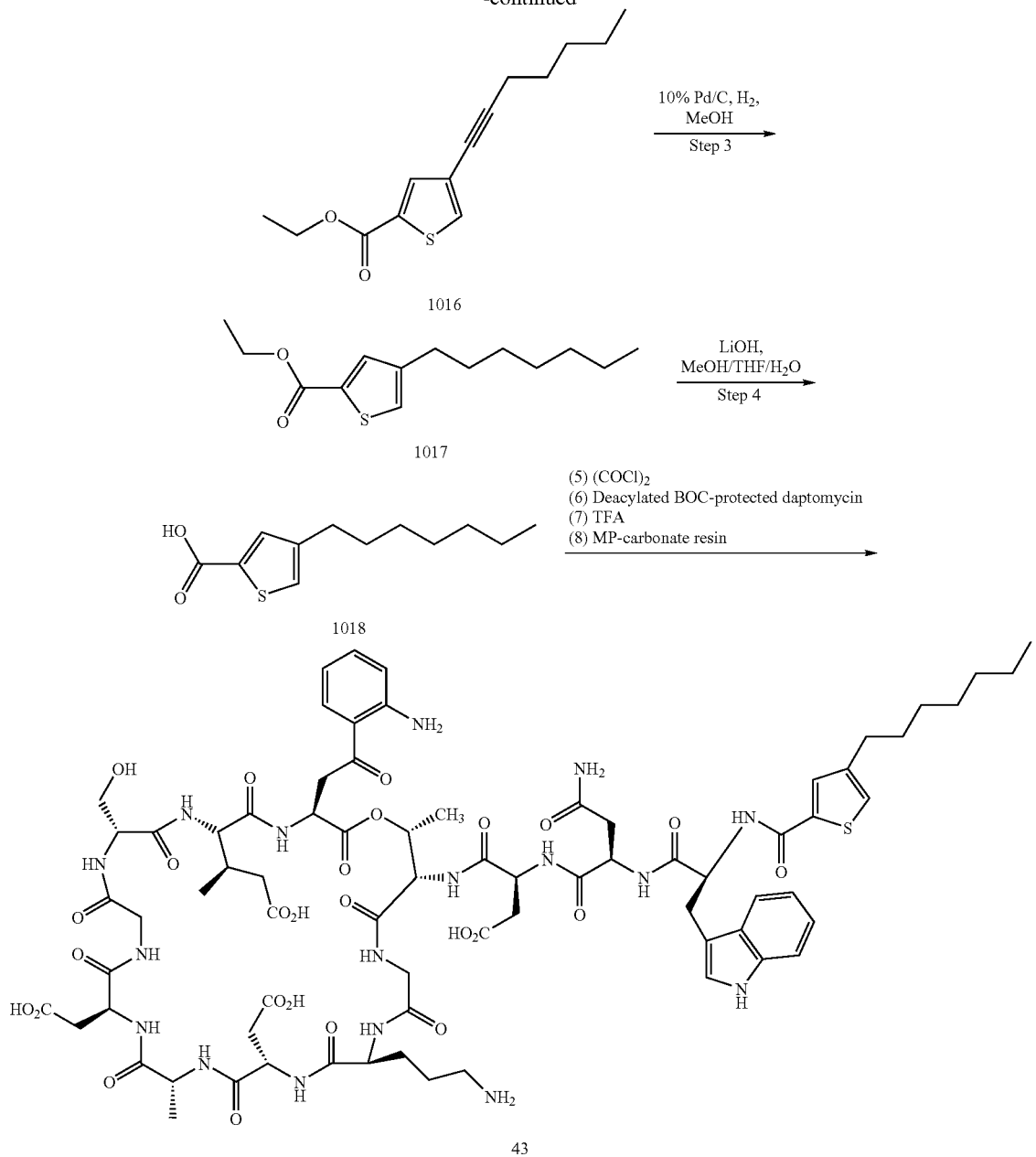

Step 1: Preparation of ethyl 4-bromothiophene-2-carboxylate (1015)

Thionyl chloride (8.8 mL, 121 mmol) was added slowly to a solution of 4-bromothiophene-2-carboxylic acid (5.0 g, 24.2 mmol) in ethanol (30 mL) at room temperature. The reaction mixture was warmed up to 65° C. and stirred for 4 hours. Removal of solvent and excess reagent under vacuum afforded the crude product ethyl 4-bromothiophene-2-carboxylate (1015), which was used in the next step without further purification.

Step 2: Preparation of ethyl 4-(hept-1-ynyl)thiophene-2-carboxylate (1016)

A reaction mixture of compound 1015 (5.64 g, 24.0 mmol), DMF (50 mL), copper (I) iodide (1.37 g, 7.2 mmol), 1-heptyne (9.42 mL, 72.0 mmol), triethylamine (6.70 mL, 48.0 mmol) and tetrakis(triphenylphosphine)palladium(0) (2.77 g, 2.4 mmol) was stirred at 65° C. for 2 hours and then cooled to room temperature. Methyl tert-butyl ether (300 mL) was added to the reaction mixture and the precipitation was removed by filtration. The clear organic solution was washed with saturated sodium chloride, dried over magnesium sulfate and concentrated under vacuum. The crude brown oil was purified with flash silica gel chromatogram (with 0%→5% EtOAc in hexane) to afford ethyl 4-(hept-1-ynyl)thiophene-2-carboxylate (1016, 5.89 g) as a brown oil. $^1$H NMR (300 MHz, δ, CDCl$_3$) 0.89 (t, 3H). 1.28-1.45 (m, 7H), 1.52-1.62 (m, 2H), 2.36 (t, 12.4 Hz, 2H), 4.33 (q, 2H), 7.48 (s, 1H), 7.72 (s, 1H).

Step 3: Preparation of ethyl 4-heptylthiophene-2-carboxylate (1017)

5% Palladium on carbon (2.52 g) was added to a solution of compound 1016 (5.94 g, 23.7 mmol) in methanol (100 mL). The reaction mixture was stirred under a hydrogen atmosphere (1 atm) for 12 hours. The reaction mixture was filtered through celite and the clear solution was concentrated under vacuum to give ethyl 4-heptylthiophene-2-carboxylate (1017, 4.80 g) which was directly used in the next step without further purification. $R_f$=0.78 (10% EtOAc in Hexane).

Step 4: Preparation of 4-heptylthiophene-2-carboxylic acid (1018)

A solution of lithium hydroxide hydrate (1.20 g, 28.3 mmol) in water (50 mL) was added to a solution of compound 1017 (2.4 g, 9.4 mmol) in THF (50 mL) and methanol (30 mL). The reaction mixture was stirred at room temperature for 12 hours. After removal of organic solvent, the aqueous solution was acidified to pH 4.0 with 6 N hydrochloric acid solution and extracted with EtOAc. The organic layer was dried and concentrated to give 4-heptylthiophene-2-carboxylic acid (1018, 2.1 g) which was directly used in the next step without further purification. $R_f$=0.03 (10% EtOAc in hexane).

Steps 5-8: Preparation of N-(4-heptylthiophene-2-carbonyl)-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (43)

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except 4-heptylthiophene-2-carboxylic acid (compound 1018) was used in the place of (E)-3-(4-pentylphenyl)but-2-enoic acid. MS m/z 1674.7 (M+H)$^+$.

Preparation of compounds of Formula (I) wherein R is

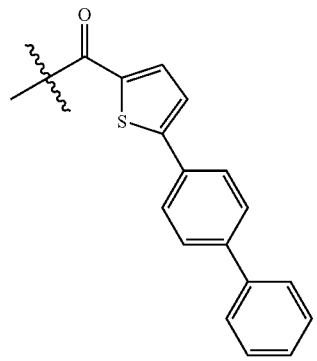 [SMILES: *C(=O)c1ccc(-c2ccc(-c3ccccc3)cc2)s1]

Example 7

Preparation of N-[5-(biphenyl-4-yl)thiophene-2-carbonyl]-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (52)

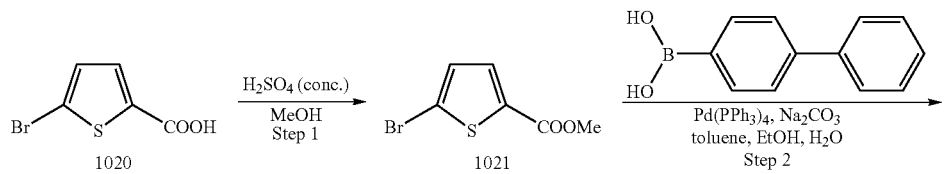

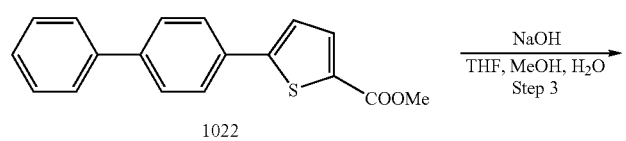

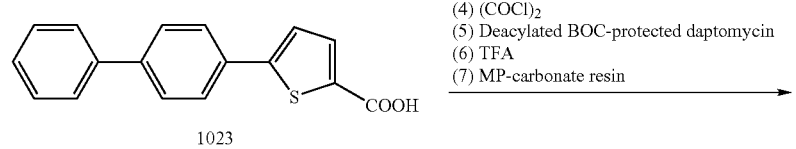

-continued

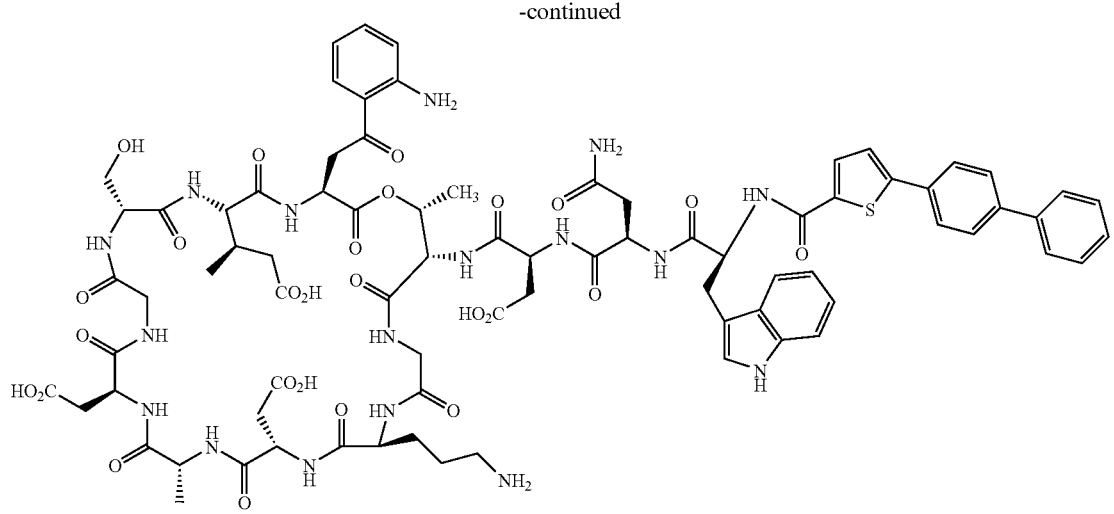

52

Step 1: Preparation of methyl 5-bromothiophene-2-carboxylate (1021)

Concentrated $H_2SO_4$ (3 mL) was added to a solution of 5-bromothiophene-2-carboxylic acid (5.0 g, 2.42 mmol) in methanol (100 mL). The reaction mixture was heated to reflux for 16 hours. After cooling to ambient temperature, the reaction mixture was concentrated to dryness. The residue was dissolved in EtOAc (60 mL), washed with saturated sodium carbonate (60 mL), and saturated sodium chloride (40 mL) and dried over anhydrous sodium sulfate. The solution was concentrated to give the compound 1021 (4.8 g). $^1$H NMR ($CDCl_3$, 300 MHz) δ 3.90 (s, 3H), 7.09-7.10 (d, 1H), 7.57-7.58 (d, 1H).

Step 2: Preparation of methyl 5-(biphenyl-4-yl)thiophene-2-carboxylate (1022)

A mixture of compound 1021 (5.0 g, 22.6 mmol), biphenyl-4-ylboronic acid (5.4 g, 27.1 mmol), sodium carbonate (5.9 g, 56.5 mmol), tetrakis(triphenylphosphine)palladium (0) (2.65 g, 2.3 mmol), toluene (200 mL), ethanol (100 mL) and water (50 mL) was heated to reflux for 12 hours under nitrogen atmosphere. The reaction mixture was cooled to ambient temperature, and extracted with dichloromethane (2×250 mL). The combined organic layers were dried over anhydrous sodium sulfate, filtered and concentrated under vacuum. The residue was purified by flash chromatography with silica gel (5% EtOAc in hexane) to give compound 1022 (5.0 g). $^1$H NMR ($CDCl_3$, 300 MHz) δ 3.92 (s, 3H), 7.32-7.49 (m, 4H), 7.62-7.80 (m, 7H).

Step 3: Preparation of 5-(biphenyl-4-yl)thiophene-2-carboxylic acid (1023)

A solution of sodium hydroxide in water (2N, 50 mL) was added to a suspension of compound 1022 (3.5 g, 11.9 mmol) in THF (50 mL) and methanol (50 mL). The reaction mixture was stirred at room temperature for 14 hours and then concentrated to approximately 1/10 of its original volume (15 mL). The concentrated solution was adjusted to pH 2-3 using 2N aqueous hydrochloric acid solution and extracted with a mixture of DCM and ethanol (7:3 ratio, 200 mL). The organic layer was dried over anhydrous sodium sulfate, filtered and concentrated to give the compound 1023 (2.7 g). $^1$H NMR ($CDCl_3$, 300 MHz) δ 7.39-7.41 (d, 1H), 7.46-7.51 (m, 2H), 7.63-7.64 (d, 1H), 7.71-7.85 (m, 7H).

Steps 4-7: Preparation of N-[5-(biphenyl-4-yl) thiophene-2-carbonyl]-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (52)

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except 5-(biphenyl-4-yl) thiophene-2-carboxylic acid (compound 1023) was used in the place of (E)-3-(4-pentylphenyl)but-2-enoic acid. MS m/z 1728.7 (M+H)$^+$.

Preparation of compounds of Formula (I) wherein R is

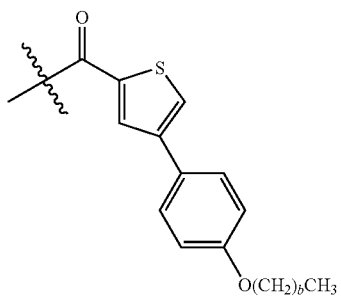

Example 8

Preparation of N-[4-(4-(hexyloxy)phenyl)thiophene-2-carbonyl]-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (58)

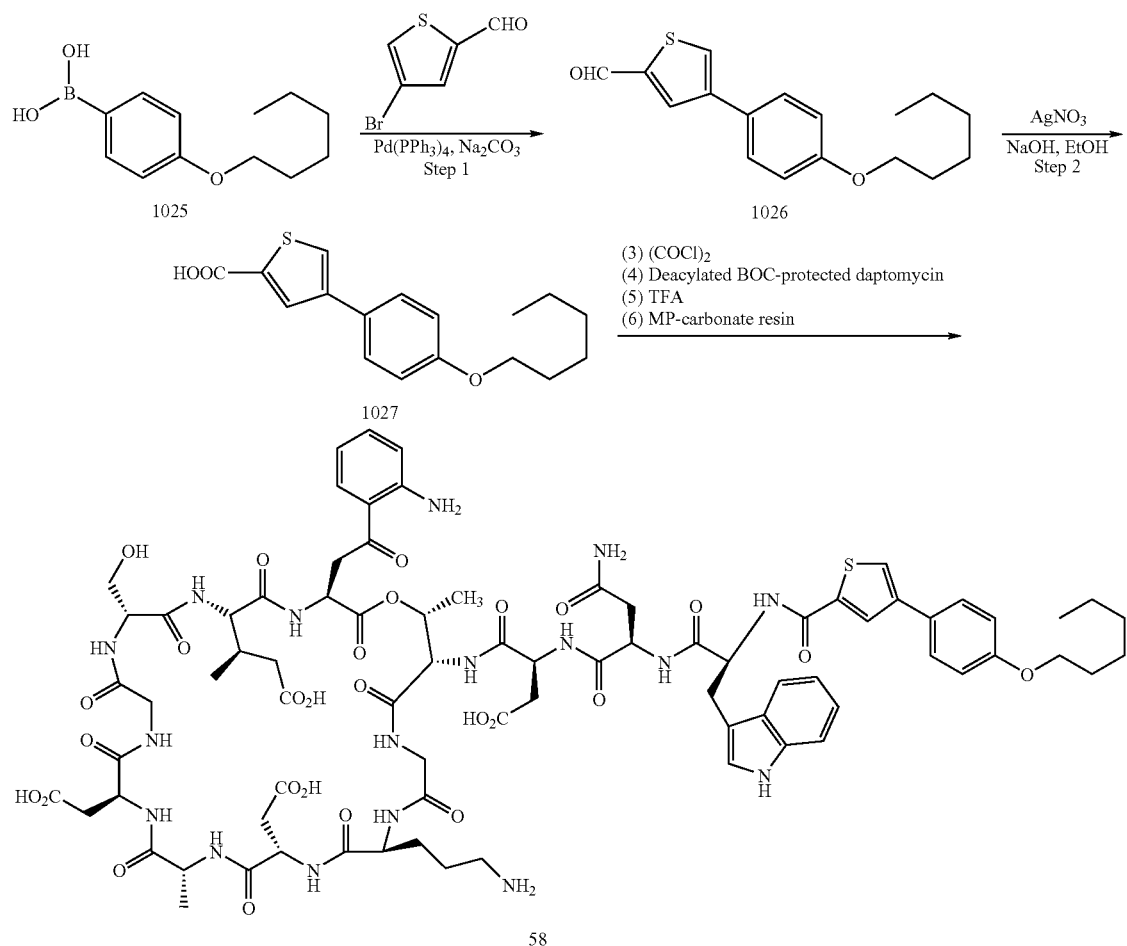

Step 1: Preparation of 4-(4-(hexyloxy)phenyl)thiophene-2-carbaldehyde (1026)

A mixture of commercial available 4-(hexyloxy)phenylboronic acid (25, 5.55 g, 25.0 mmol), 4-bromothiophene-2-carbaldehyde (5.25 g, 27.5 mmol), tetrakis(triphenylphosphine)palladium(0) (0.6 g, 0.13 mmol), toluene (25 mL), ethanol (15 mL) and aqueous sodium carbonate (2 M, 25 mL) was stirred under reflux for 18 hours under a nitrogen atmosphere. The reaction mixture was cooled to ambient temperature and the aqueous layer was extracted with dichloromethane (3×50 mL). The combined organic layers were washed with saturated sodium chloride (50 mL), and dried over magnesium sulfate. After filtration and concentration, the crude material was purified by recrystallization from ethyl acetate/petroleum ether (1/2, v/v) to afford the compound 1026 (3.8 g).

Step 2: Preparation of 4-(4-(hexyloxy)phenyl)thiophene-2-carboxylic acid (1027)

A mixture of silver nitrate (4.07 g, 24 mmol), compound 1026 (1.73 g, 6 mmol), ethanol (30 mL) and aqueous sodium hydroxide solution (1M, 48 mL) was stirred at 40° C. for 3 hours and then diluted with water (150 mL). The aqueous phase was washed with ethyl acetate (2×300 mL) and acidified to pH 1 with 1N aqueous hydrochloric acid solution. The aqueous solution was extracted with EtOAc (2×300 mL). The combined organic phases were dried over anhydrous sodium sulfate, filtered and concentrated to yield compound 1027 (1.5 g) which was used directly in the next step without further purification. $^1$H NMR (300 MHz, DMSO-d6) δ 0.87 (m, 3H), 1.31-1.30 (m, 6H), 1.65 (m, 2H), 3.98 (m, 2H), 6.96 (d, J=8.4 Hz, 2H), 7.66 (d, J=8.7 Hz, 2H), 8.05 (s, 2H), 13.19 (s, 1H). MS m/z=303 [M−H]$^-$.

Steps 3-6: Preparation of N4-[(4-(hexyloxy)phenyl)thiophene-2-carbonyl]-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (58)

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except 4-(4-(hexyloxy)phenyl)thiophene-2-carboxylic acid (compound 1027) was used in the place of (E)-3-(4-pentylphenyl)but-2-enoic acid. MS m/z 1752.7 (M+H)$^+$.

Preparation of compounds of Formula (I) wherein R is

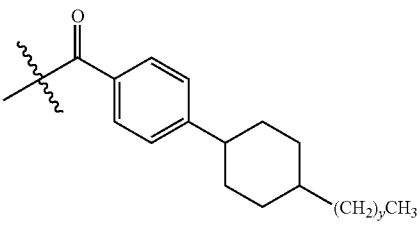

Example 9

Preparation of N-[4-(-4-hexylcyclohexyl)benzoyl]-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (54)

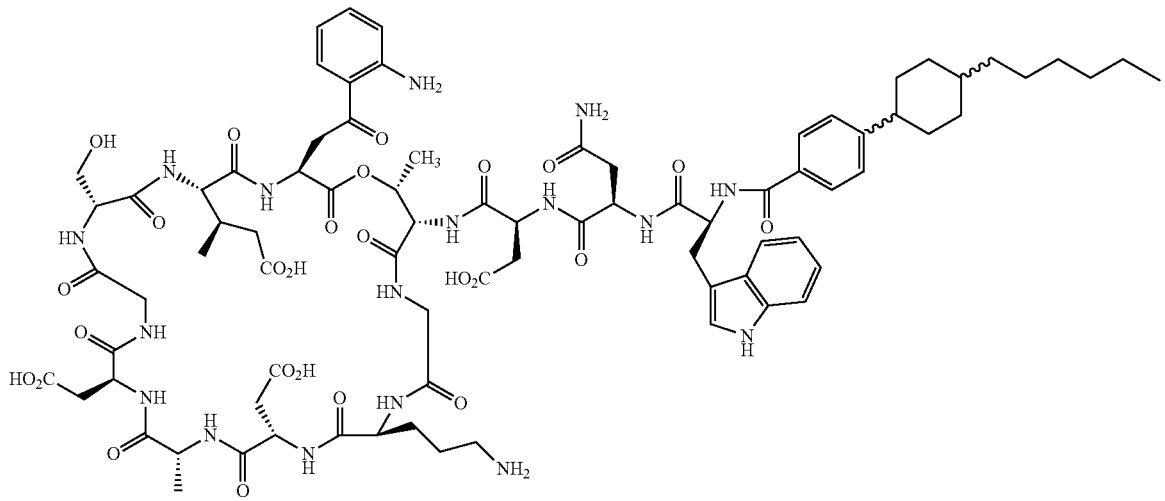 [SMILES: CCCCCCC1CCC(c2ccc(C(=O)N[C@@H](Cc3c[nH]c4ccccc34)C(=O)N[C@H](CC(N)=O)C(=O)N[C@@H](CC(=O)O)C(=O)N[C@@H]3C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c4ccccc4N)C(=O)O[C@@H]3C)cc2)CC1]

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 4-(4-hexylcyclohexyl)benzoic acid was used in the place of (E)-3-(4-pentylphenyl)but-2-enoic acid. MS m/z 1736.8 (M+H)$^+$.

Preparation of compounds of Formula (I) wherein R is

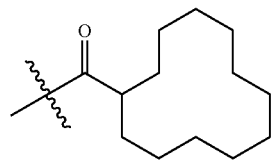 [SMILES: *C(=O)C1CCCCCCCCCCC1]

Example 10

Preparation of N-cyclododecanecarbonyl-L-Tryptophyl-D-Asparaginyl-L-α-Aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (28)

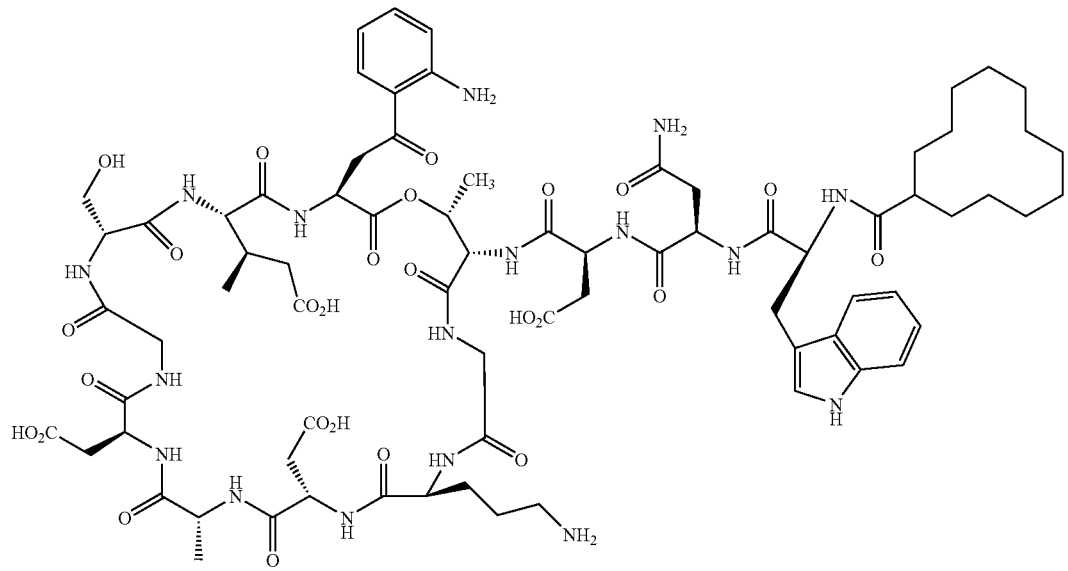

28

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available cyclododecanecarboxylic acid was used in the place of (E)-3-(4-pentylphenyl)but-2-enoic acid. MS m/z 1660.8 (M+H)$^+$.

Preparation of compounds of Formula (I) wherein R is

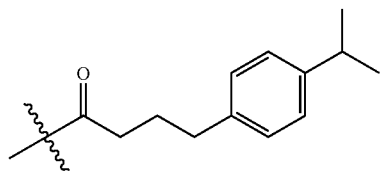 [SMILES: *C(=O)CCCc1ccc(C(C)C)cc1]

Example 11

Preparation of N-[4-(4-isopropylphenyl)butanoyl]-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (30)

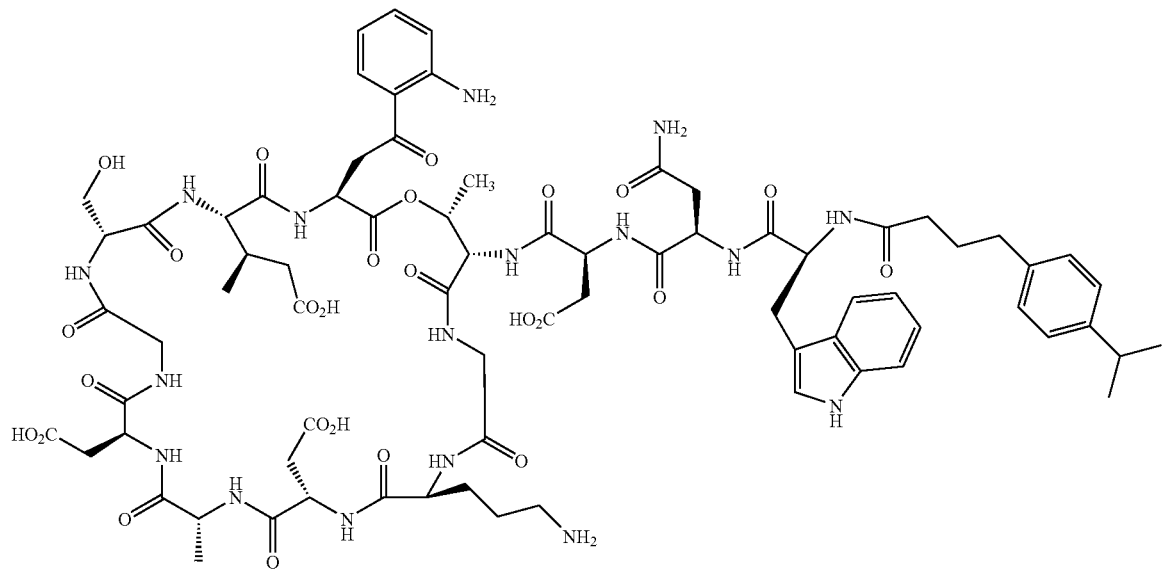

The above compound was prepared in a similar manner as described in steps 3-6 in the preparation of N-{1-[(E)-3-(4-pentylphenyl)but-2-enoyl]}-L-tryptophyl-D-asparaginyl-L-α-aspartyl-L-threonylglycyl-L-ornithyl-L-α-aspartyl-D-alanyl-L-α-aspartylglycyl-D-seryl-(3R)-3-methyl-L-α-glutamyl-(αS)-α,2-diamino-γ-oxobenzenebutanoic acid (13→4)-lactone (See Example 1), except commercially available 4-(4-isopropylphenyl)butanoic acid was used in the place of (E)-3-(4-pentylphenyl)but-2-enoic acid. MS m/z 1654.7 (M+H)$^+$.

Additional compounds were produced using procedures similar to those described above in examples 1-11 from the corresponding commercially available carboxylic acids. The carboxylic acids were converted into either the activated PFP ester or the acyl chloride as indicated in Table V then treated with the Deacylated BOC-protected daptomycin, followed by removal of the protecting group.

TABLE V

| Compound # | activation method |
| --- | --- |
| 1 | PFP ester |
| 2 | PFP ester |
| 3 | PFP ester |
| 5 | PFP ester |
| 6 | PFP ester |
| 7 | PFP ester |
| 8 | PFP ester |
| 9 | PFP ester |
| 10 | PFP ester |
| 11 | PFP ester |
| 12 | PFP ester |
| 13 | PFP ester |
| 15 | PFP ester |
| 18 | PFP ester and acyl chloride |
| 19 | PFP ester and acyl chloride |
| 20 | acyl chloride |
| 24 | PFP ester |
| 26 | PFP ester |
| 27 | PFP ester |
| 29 | PFP ester |
| 31 | PFP ester |
| 32 | PFP ester and acyl chloride |
| 35 | acyl chloride |
| 36 | PFP ester |
| 37 | PFP ester |
| 38 | acyl chloride |
| 39 | acyl chloride |
| 41 | PFP ester |
| 42 | PFP ester |
| 45 | PFP ester |
| 46 | PFP ester |
| 47 | PFP ester |
| 53 | PFP ester and acyl chloride |
| 54 | PFP ester |
| 59 | PFP ester |
| 60 | PFP ester |
| 62 | PFP ester and acyl chloride |
| 63 | PFP ester |
| 64 | PFP ester |
| 65 | PFP ester |
| 66 | PFP ester |
| 67 | PFP ester |
| 68 | PFP ester |
| 69 | PFP ester |
| 70 | PFP ester |
| 71 | PFP ester |
| 72 | PFP ester |

TABLE V-continued

| Compound # | activation method |
|---|---|

To produce compounds wherein the carboxylic acids were not commercially available, the carboxylic acids were either produced by procedures described in the literature or as described in examples 12-17 below. The carboxylic acids were then converted into either the activated PFP ester, isocyanate or the acyl chloride as indicated in Table VI then treated with the Deacylated BOC-protected daptomycin, followed by removal of the protecting group using the procedures described in Examples 1-11 above.

TABLE VI

| Carboxylic acid compound # | Synthetic Procedure | Activation method | Compound # produced |
|---|---|---|---|
| | Tetrahedron Letters (1999), 40 (12), 2401-2404 | PFP ester | 4 |
| 81 | Example 17 | isocyanate | 14 |
| 82 | Example 18 | isocyanate | 17 |
| 78 | Example 15 | acyl chloride | 21 |
| | Journal of the Chemical Society, Chemical Communications (1979), (21), 974-5. | acyl chloride | 23 |
| | Journal of the American Chemical Society (1926), 48 2385-93 | PFP ester | 25 |
| | U.S. Pat. No. 3,716,644 | acyl chloride | 40 |
| 79 | Example 16 | isocyanate | 51 |
| 73 | Example 12 | PFP ester | 55 |
| 75 | Example 14 | PFP ester | 56 |
| 74 | Example 13 | PFP ester | 57 |

Example 12

Preparation of 4-(4-(isopropylthio)phenyl)thiophene-2-carboxylic acid (73)

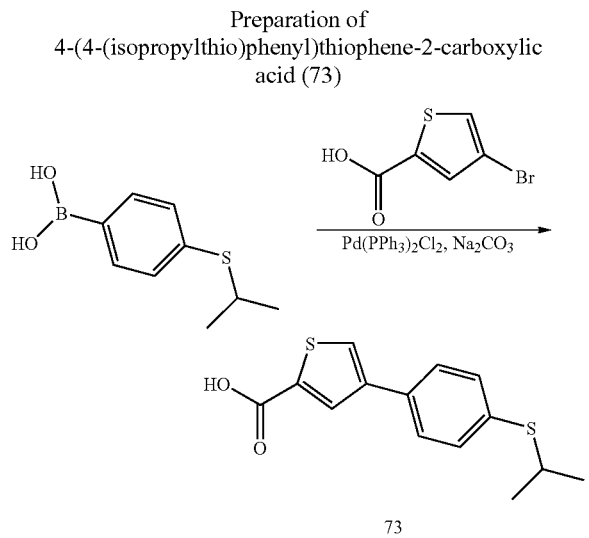

73

A mixture of commercially available 4-(isopropylthio)phenylboronic acid (735 mg, 3.75 mmol), 4-bromothiophene-2-carboxylic acid (776 mg, 3.75 mmol), Bis(triphenylphosphine)palladium (II) chloride (131 mg, 0.188 mmol), acetonitrile (7.5 mL) and aqueous sodium carbonate (1M, 7.5 mL) was heated to 150° C. by microwave irradiation (Biotage Intiator™ Sixty, 0-300 W, pre-stirring 2 minutes) for 5 minutes under an argon atmosphere. The reaction mixture was cooled to ambient temperature, diluted with water (75 mL), and extracted with EtOAc (2×50 mL). The aqueous layer obtained was then acidified with aqueous HCl (3.0M) to pH 2 and extracted with EtOAc (2×50 mL). The combined organic layers were dried over sodium sulfate, filtrated and concentrated to afford compound 73 (990 mg) which was used in next step without further purification.

Example 13

Preparation of 4-(4-(hexylthio)phenyl)thiophene-2-carboxylic acid (74)

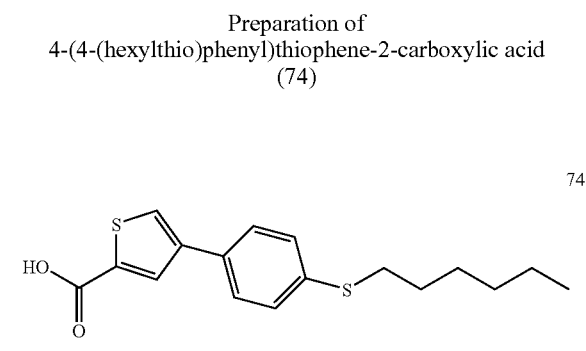

74

The title compound was prepared in a similar manner as described in the preparation of 4-(4-(isopropylthio)phenyl)thiophene-2-carboxylic acid (compound 73, example 12), except 4-(hexylthio)phenylboronic acid (Chemical Communications 2003, 1, 138-139) was used in the place of 4-(isopropylthio)phenylboronic acid.

Example 14

Preparation of 4-(4-(propylthio)phenyl)thiophene-2-carboxylic acid (75)

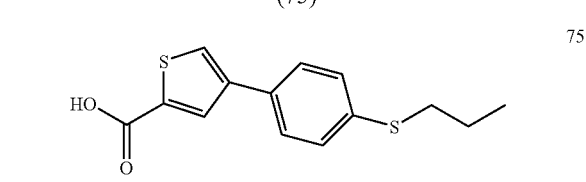

75

The title compound was prepared in a similar manner as described in the preparation of 4-(4-(isopropylthio)phenyl)thiophene-2-carboxylic acid (compound 73, example 12), except commercially available 4-(propylthio)phenylboronic acid was used in the place of 4-(isopropylthio)phenylboronic acid.

Example 15

Preparation of 4-(4-isopropylcyclohexyl)butanoic acid (78)

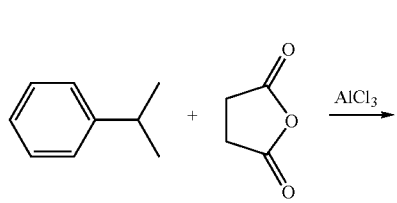

89
-continued

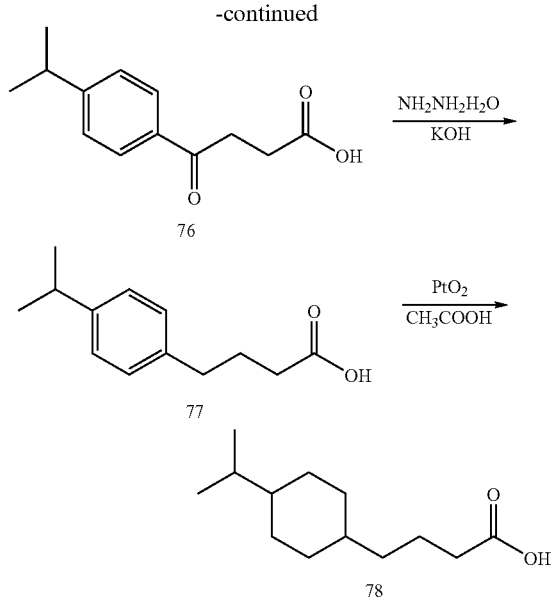

Step 1: Preparation of 4-(4-isopropylphenyl)-4-oxobutanoic acid (76)

To a suspension of aluminum (III) chloride (6.7 g, 50.1 mmol) and succinic anhydride (2 g, 20 mmol) in 1,2-dichloroethane was added Cumene (2 g, 16.7 mmol) at 0-5° C. The reaction mixture was stirred at ambient temperature for 16 hours, diluted with 20 mL of aqueous HCl solution (1 M) and extracted with ethyl acetate (3×80 mL). The combined organic phases were washed with saturated sodium chloride (100 mL), dried over $Na_2SO_4$, filtered and concentrated in vacuo. The residue was purified by flash column chromatography on silica-gel (4×20 cm, petroleum ether:ethyl acetate=8:1 elution) to give 3.1 g of compound 76. $^1$H NMR ($CDCl_3$, 300 MHz) δ 1.27-1.29 (d, 6H), 2.80-2.84 (t, 2H), 2.95-3.00 (m, 1H), 3.29-3.33 (t, 2H), 7.32-7.34 (d, 2H), 7.92-7.94 (d, 2H). MS m/z 221 (M+H)$^+$.

Step 2: Preparation of 4-(4-isopropylphenyl)butanoic acid (77)

A solution of compound 76 (0.5 g, 2.27 mmol) and 2 mL of 80% hydrazine hydrate was stirred at 45° C. for 1 hour. To the mixture, KOH (1 g, 17.8 mmol) was added and the reaction mixture was heated to 104-150° C. for 2 hours. After cooling to ambient temperature, the reaction mixture was diluted with 10 mL of water and acidified to pH 2 with aqueous HCl (1 M) and extracted with ethyl acetate (2×20 mL). The combined organic layers were dried over anhydrous sodium sulfate, filtered and concentrated under reduced pressure. The residue was purified by flash column chromatography on silica-gel (2×15 cm, petroleum ether:ethyl acetate=8:1 elution) to give 275 mg of compound 77. MS m/z 207 (M+H)$^+$.

Step 3: Preparation of 4-(4-isopropylcyclohexyl)butanoic acid (78)

A suspension of compound 77 (1.0 g, 4.8 mmol) and 0.1 g of $PtO_2$ in 50 mL of acetic acid was stirred under a $H_2$ atmosphere (50 psi) at ambient temperature for 6 hours. After filtering and evaporating off the solvent, 1.1 g crude product was obtained. The compound was used directly in the next step without further purification. LC-MS m/z 211 (M−H$^+$).

Example 16

Preparation of 1-heptyl-4-isocyanatobenzene (79)

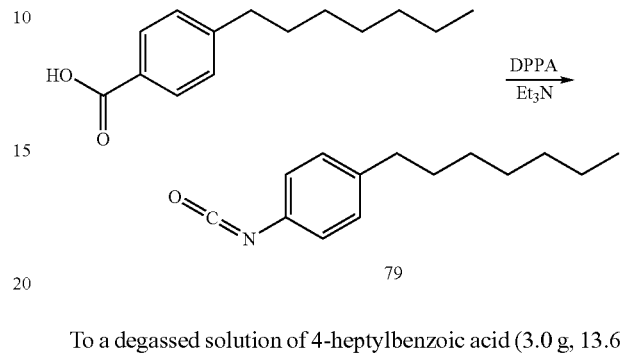

To a degassed solution of 4-heptylbenzoic acid (3.0 g, 13.6 mmol) in anhydrous toluene (30 mL) and $Et_3N$ (3 mL, 21.5 mmol), was added diphenyl phosphoryl azide (2 mL, 9.3 mmol) dropwise. After completion of the addition, the reaction mixture was heated to reflux and stirred for 2 hours. The mixture was concentrated to dryness under reduced pressure to give the product, 1-heptyl-4-isocyanatobenzene (79), as an oil, which was used directly in the next reaction without further purification.

Example 17

Preparation of 2-isocyanatoundecane (81)

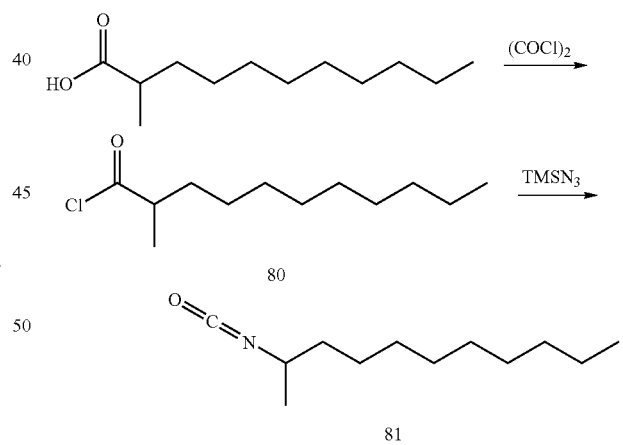

Step 1: Synthesis of 2-methylundecanoyl chloride (80)

To a stirred solution of 2-methylundecanoic acid (0.40 g, 2.0 mmol) in anhydrous dichloromethane (20 ml) and a catalytic amount of DMF (approximately 0.02 ml) was added oxalyl chloride (0.4 mL, 4.6 mmol). The resulting mixture was stirred vigorously for 2 hours at room temperature. The organic solvent was evaporated under reduced pressure and the residue (80) was used in the next step.

Step 2: Synthesis of 2-isocyanatoundecane (81)

To a stirred solution of 2-methylundecanoyl chloride (2.0 mmol) in anhydrous dichloromethane (10 ml) was added azidotrimethylsilane (TMSN$_3$) (0.32 mL, 2.4 mmol). The resultant mixture was heated at reflux for 5 hours. The excess azidotrimethylsilane and solvent were removed at 50° C. in vacuo and the resultant residue (81) was used in the next step.

Example 18

Preparation of 1-isocyanato-4-pentylcyclohexane (82)

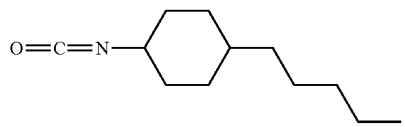

The title compound was prepared in a similar manner as described in the preparation of 2-isocyanatoundecane (compound 81, example 17), except commercially available 4-pentylcyclohexanecarboxylic acid was used in the place of 2-methylundecanoic acid.

Example 19

In Vitro Biological Activity

Compounds according to Formula I were tested for antimicrobial activity against a panel of organisms. Aerobic organisms, *Staphylococcus aureus, Enterococcus faecalis* and *E. faecium*, were tested by broth microdilution according to Clinical and Laboratory Standards Institute (CLSI) document M7-A7 (Clinical and Laboratory Standards Institute. *Methods for Dilution Antimicrobial Susceptibility Tests for Bacteria that Grow Aerobically; Approved Standard—Seventh Edition*. CLSI document M7-A7 [ISBN 1-56238-587-9]. Clinical and Laboratory Standards Institute, 940 West Valley Road, Suite 1400, Wayne, Pa. 19087-1898 USA, 2006) with modifications as described below. Mueller Hinton Broth (MHBc) was supplemented with 50 mg/L calcium (equivalent to human physiological levels of calcium) and assay plates were incubated 18-20 hours at 37° C. with aeration (200 rpm).

Briefly, compounds were dissolved in either sterile, distilled water or a 50:50 mix by volume of dimethyl sulfoxide and sterile, distilled water depending upon the solubility of the compound and were diluted to the final concentration (0.03 μg/mL-32 μg/mL) in microbial growth media, MHBc. In all cases the final concentration of dimethyl sulfoxide incubated with cells is less than or equal to 1%. For minimum inhibitory concentration (MIC) calculations, 2-fold dilutions of compounds were added to wells of a microtiter plate containing 5×10$^5$ bacteria in a final volume of 100 μL of media. Following incubation, (18-20 hours at 37° C. with aeration at 200 rpm) growth was confirmed visually by placing plates over a viewing apparatus (stand with a mirror underneath) and then the optical density (OD$_{600}$) was measured using a SpectraMax 340PC$^{384}$ plate reader. Growth was defined as turbidity that could be detected with the naked eye or achieving minimum OD$_{600}$ of 0.1. MIC values (in μg/mL) were defined as the lowest concentration producing no visible turbidity.

Anaerobic *Clostridium difficile*, MIC values were determined at R. M. Alden (RMA) Research Laboratory (Culver City, Calif.) by the agar dilution method according to CLSI document M11-A7 (Clinical and Laboratory Standards Institute. *Methods for Antimicrobial Susceptibility Testing of Anaerobic Bacteria; Approved Standard—Seventh Edition*. CLSI document M11-A7 [ISBN 1-56238-626-3]. Clinical and Laboratory Standards Institute, 940 West Valley Road, Suite 1400, Wayne, Pa. 19087-1898 USA, 2007.) The agar used during testing was prepared to contain 50 mg/L Ca$^{++}$ by preparing *Brucella* broth with free Ca$^{++}$ ion concentration determined using a calcium electrode, and adding 3.9 mL/L of 10 mg/mL of CaCl$_2$ solution and then 1.5% agar, in addition, media was supplemented with Vitamin K$_1$, hemin and 5% laked sheep blood.

The *C. difficile* strains were recovered from toxin-positive fecal specimens collected from 2006 to 2008. They were stored at ±70° C. in 20% skim milk in the RMA culture collection. The strains were removed from the freezer and transferred at least twice on supplemented *Brucella* blood agar before testing. *C. difficile* (ATCC #700057) and *Staphylococcus aureus* (ATCC #29213) were used as controls.

Serial two-fold dilutions of the compounds were prepared on the day of testing, and added to molten agar deeps, mixed, and poured into Petri dishes. After solidifying, the plates were dried in the incubator for 30 minutes.

The inoculum was prepared in the anaerobic chamber from 48-hour cultures by making suspensions equal to the turbidity of the 0.5 McFarland standard in *Brucella* broth, and dispensed into the wells of the Steer's replicator head. The replicator was removed from the chamber for inoculation of the drug-containing plates on the bench in ambient conditions. Drug-free control plates were stamped before and after each drug series to test for viability.

The plates were transferred back into the anaerobic chamber and incubated at 37° C. for 48 hours. They were removed from the chamber and examined for growth. The MIC was the concentration of drug that inhibited growth or markedly reduced growth as compared to the drug-free control plate, in accordance in CLSI guidance.

The MIC values of representative compounds of the present invention are listed in Table VII. *C. difficile* values are represented as a MIC90 where 90% or 27 out of the 30 isolates tested, had this MIC (μg/mL) or lower.

TABLE VII

Biological Activity of Compounds of Formula I

| Cmpd # | Lot # | C. diff MIC$_{90}$ | C. diff MIC$_{50}$ Nap-1 | C. diff MIC$_{90}$ Nap-1 | Sa42 | Sa399 | Sa278 | Efm14 | Efm384 | Efs201 | Efs312 |
|---|---|---|---|---|---|---|---|---|---|---|---|
| Daptomycin | n/a | 2 | | | 0.5 | 0.5 | 8 | 4 | >32 | 2 | >32 |
| 1 | 1 | | | | 8 | 2 | >32 | 32 | >32 | 32 | >32 |
| 2 | 2 | 4 | | | 2 | 0.5 | 8 | 2 | >32 | 2 | 32 |
| 3 | 2 | | | | 0.5 | 1 | 1 | 1 | 4 | 0.5 | 32 |
| 4 | 1 | | | | 2 | 2 | 4 | 2 | 8 | 2 | 32 |
| | 2 | | | | 0.25 | 0.5 | 0.5 | 0.5 | 4 | 0.5 | 16 |
| 5 | 2 | 8 | | | 0.5 | 0.5 | 2 | 0.5 | 8 | 0.5 | 8 |
| 6 | 2 | 16 | | | 1 | 0.25 | 2 | 0.5 | 4 | 0.25 | 4 |
| 7 | 1 | 16 | | | 1 | 0.5 | 2 | 0.5 | 4 | 0.25 | 4 |

TABLE VII-continued

Biological Activity of Compounds of Formula I

| Cmpd # | Lot # | C. diff MIC$_{90}$ | C. diff MIC$_{50}$ Nap-1 | C. diff MIC$_{90}$ Nap-1 | Sa42 | Sa399 | Sa278 | Efm14 | Efm384 | Efs201 | Efs312 |
|---|---|---|---|---|---|---|---|---|---|---|---|
| 8 | 1 | | | | 0.5 | 0.5 | 4 | 4 | 32 | 4 | >32 |
|   | 2 | 8 | | | 2 | 2 | >32 | 16 | >32 | 16 | >32 |
| 9 | 1 | | | | 0.5 | 0.5 | 8 | 4 | 32 | 4 | >32 |
| 10 | 1 | 1 | | | 0.25 | 0.25 | 1 | 1 | 4 | 0.13 | >32 |
| 11 | 1 | 1 | | | 0.125 | 0.25 | 0.5 | 1 | 4 | 1 | 16 |
| 12 | 1 | | | | 4 | 2 | 8 | 8 | >32 | 16 | 32 |
| 13 | 1 | | | | 2 | 1 | 32 | 16 | >32 | 16 | >32 |
| 14 isomer I | 1 | 1.0 | | | 0.25 | 0.5 | 1 | 0.5 | 8 | 1 | 32 |
| 14 isomer II | 1 | 2 | | | 0.25 | 0.25 | 1 | 0.25 | 8 | 0.5 | 16 |
| 15 | 1 | | | | 2 | 2 | 16 | 8 | >32 | 8 | >32 |
| 16 | 1 | 1 | | | 0.5 | 0.5 | 8 | 1 | 32 | 1 | 16 |
|   | 5 | 0.5 | | | 0.5 | 1 | 8 | 2 | 16 | 2 | >32 |
| 17 | 1 | 1 | | | 0.25 | 0.25 | 0.25 | 1 | 16 | 1 | >32 |
| 18 | 1 | | | | 2 | 1 | 4 | 2 | 8 | 2 | 32 |
|   | 2 | 0.5 | | | 0.5 | 1 | 2 | ND | ND | 0.5 | 16 |
| 19 | 1 | | | | 1 | 2 | 4 | 2 | 4 | 1 | 8 |
|   | 2 | | | | 1 | 0.5 | 2 | 2 | 8 | 1 | 16 |
|   | 2 | | | | 0.25 | 0.5 | 0.5 | 0.25 | 1 | 0.125 | 4 |
|   | 3 | 0.250 | | | 0.125 | 0.125 | 0.5 | ND | ND | 0.125 | 2 |
| 20 | 1 | | | | 0.5 | 2 | 8 | ND | ND | 0.5 | 4 |
| 21 | 1 | | | | 0.063 | 1 | 2 | ND | ND | 0.25 | 32 |
| 22 | 1 | | | | 1 | 1 | 2 | 1 | 4 | 1 | 8 |
|   | 2 | | | | 2 | 2 | 2 | 4 | 16 | 2 | >32 |
|   | 3 | 1 | | | 1 | 0.50 | 4 | 1 | 16 | 1 | 32 |
|   | 4 | | | | 0.25 | 0.5 | 1 | 1 | 4 | 0.5 | 8 |
| 23 | 1 | 0.5 | | | 0.50 | 0.5 | 1 | 0.5 | 4 | 0.5 | 4 |
| 24 | 1 | 4 | | | 1 | 1 | 8 | 4 | 32 | 2 | >32 |
| 25 | 1 | 1 | | | 0.5 | 0.5 | 1 | 1 | 8 | 0.5 | 16 |
| 26 | 1 | 2 | | | 1 | 0.5 | 2 | 2 | 16 | 1 | >32 |
| 27 isomer I | 1 | 2 | | | 2 | 2 | 8 | 4 | 32 | 2 | 32 |
| 27 isomer II | 1 | 1 | | | 1 | 0.5 | 2 | 1 | 4 | 0.5 | 32 |
| 28 | 1 | 4 | | | 1 | 1 | 4 | 4 | 32 | 4 | >32 |
|   | 2 | | | | 0.5 | 0.5 | 8 | 2 | 32 | 2 | >32 |
| 29 | 1 | 16 | | | 8 | 8 | >32 | >32 | >32 | >32 | >32 |
| 30 | 1 | 8 | | | 2 | 1 | 32 | 16 | >32 | 8 | >32 |
|   | 2 | | | | 0.5 | 0.5 | 32 | 8 | >32 | 8 | >32 |
| 31 | 1 | | | | 4 | 4 | >32 | 16 | >32 | 16 | >32 |
| 32 | 1 | 4 | | | 1 | 1 | 4 | 4 | 32 | 2 | >32 |
|   | 2 | | | | 0.125 | 0.063 | 1 | 1 | 8 | 0.5 | 32 |
| 33 | 1 | | | | | | | | | | |
|   | 2 | 1 | | | 0.25 | 0.125 | 1 | 0.5 | 4 | 0.5 | 8 |
|   | 4 | | | | ND | ND | 0.125 | 0.063 | 2 | 0.125 | 2 |
|   | 6 | 0.5 | | | | | | | | | |
|   | 8 | 0.5 | | | | | | | | | |
| 34 | 1 | | | | 0.125 | 0.125 | 0.5 | 0.5 | 2 | 0.5 | 4 |
|   | 2 | 1 | | | 0.5 | 0.5 | 1 | 2 | 4 | 1 | 8 |
|   | 3 | | | | 0.5 | 0.5 | 0.25 | 1 | 4 | 0.5 | 4 |
| 35 | 1 | 2 | | | 0.5 | 0.5 | 4.00 | 2 | 32 | 1.0 | >32 |
| 36 | 1 | 0.5 | | | 0.25 | 0.25 | 1.00 | 0.5 | 4 | 0.5 | 4 |
| 37 | 1 | 1 | | | 0.25 | ND | 0.25 | 0.5 | 2 | 0.5 | 2 |
| 38 | 1 | 1 | | | 0.25 | 0.5 | 0.50 | 0.5 | 1 | 0.5 | 0.5 |
| 39 | 1 | 16 | | | 1.00 | 0.500 | 2.00 | 2.0 | 2 | 0.5 | 2 |
| 40 | 1 | 32 | | | 4.00 | 4.000 | 16.00 | 32.0 | 32 | 4.0 | 8 |
| 41 | 1 | 4 | | | 4 | 2 | 2 | 8 | >32 | 4 | >32 |
| 42 | 1 | 0.5 | | | 0.5 | 1 | 4 | 2 | 8 | 1 | ND |
| 43 | 2 | 2 | | | | | | | | | |
|   | 3 | 2 | | | 0.125 | 0.5 | 1 | 1 | 16 | 1 | 32 |
| 44 | 1 | 8.00 | | | 4 | 4 | 4 | 16 | >32 | 8 | >32 |
| 45 isomer I | 1 | 32 | | | 8 | 8 | >32 | >32 | >32 | >32 | >32 |
| 45 isomer II | 1 | 8 | | | 4 | 4 | >32 | 32 | >32 | 32 | >32 |
| 46 | 1 | | | | 32 | 16 | >32 | >32 | >32 | >32 | >32 |
|   | 1 | 16 | | | 16 | 32 | >32 | >32 | >32 | >32 | >32 |
| 47 | 1 | 8 | | | 16 | ND- | >32 | >32 | >32 | 32 | >32 |
|   | 1 | | | | 32 | 16 | >32 | >32 | >32 | >32 | >32 |
| 48 | 1 | 2 | | | | | | | | | |
|   | 2 | 2 | | | 1 | 1 | 2 | 2 | 32 | 1 | >32 |
|   | 3 | | | | 0.25 | 0.25 | 4 | ND | ND | 1 | 32 |

TABLE VII-continued

Biological Activity of Compounds of Formula I

| Cmpd # | Lot # | C. diff MIC$_{90}$ | C. diff MIC$_{50}$ Nap-1 | C. diff MIC$_{90}$ Nap-1 | Sa42 | Sa399 | Sa278 | Efm14 | Efm384 | Efs201 | Efs312 |
|---|---|---|---|---|---|---|---|---|---|---|---|
| 49 | 1 | 1 | | | | | | | | | |
| | 2 | | | | 0.063 | 0.063 | 1 | 0.25 | 4 | 0.125 | 8 |
| | 3 | | | | | | | | | | |
| | 4 | | | | 0.25 | 0.25 | 1 | 0.5 | 4 | 0.25 | 4 |
| | 5 | | | | 0.25 | 0.25 | 1 | 0.5 | 4 | 0.25 | 4 |
| | 6 | | | | 0.25 | 0.5 | 1 | 0.5 | 4 | 0.5 | 4 |
| | 7 | 0.5 | | | | | | | | | |
| | 8 | 0.5 | | | | | | | | | |
| | 9 | | | | 0.275 | | | | | | |
| | | | 0.25 | 0.50 | | | | | | | |
| 50 | 2 | 0.5 | | | 0.25 | 0.5 | 1 | 1 | 4 | 0.25 | 4 |
| 51 | 1 | 0.5 | | | 0.125 | 0.125 | 1 | 0.5 | 4 | 0.25 | 8 |
| 52 | 1 | 2 | | | 0.25 | 0.25 | 0.5 | 1 | 4 | 0.5 | 8 |
| | 2 | | | | 0.25 | 0.25 | 0.5 | 0.5 | 4 | 0.5 | 16 |
| 53 isomer I | 1 | 1 | | | 0.25 | 0.125 | 0.25 | 0.25 | 2 | 0.13 | 2 |
| | 2 | | | | 0.063 | 0.125 | 0.5 | 0.25 | 1 | 0.063 | 2 |
| 53 isomer II | 1 | 1 | | | 0.5 | 1 | 2 | 1 | 4 | 1 | 4 |
| 54 isomer I | 1 | 4 | | | 0.125 | 0.25 | 0.125 | 0.5 | 0.5 | 0.25 | 0.5 |
| | 2 | | | | 0.125 | 0.063 | ND | 0.25 | 0.25 | 0.063 | 0.25 |
| 54 isomer II | 1 | 4 | | | 1 | 1 | 2 | 1 | 2 | 2 | 2 |
| 55 | 1 | | | | 0.5 | 0.25 | 4 | 2 | 8 | 2 | >32 |
| 56 | 1 | | | | 2 | 2 | 8 | 8 | 32 | 8 | >32 |
| 57 | 1 | | | | 1 | 1 | 2 | 2 | 4 | 1 | 8 |
| | 2 | 8 | | | 8 | 4 | 4 | 16 | 16 | 4 | >32 |
| 58 | 1 | | | | 0.125 | 0.25 | 0.5 | 0.5 | 1 | 0.25 | 2 |
| | 2 | 4 | | | 0.5 | 0.5 | 1 | 1 | 2 | 0.5 | 8 |
| | 2 | | | | 1 | 1 | 1 | 2 | 4 | 1 | 8 |
| | 3 | | | | 0.063 | 0.125 | 0.5 | ND | ND | 0.25 | 1 |
| 59 | 1 | 4 | | | 0.5 | 0.5 | 4 | 4 | 32 | 4 | >32 |
| 60 | 1 | | | | 1 | 4 | 8 | 4 | 16 | 4 | >32 |
| 61 | 1 | 2 | | | 0.25 | 0.25 | 1 | 0.5 | 2 | 0.25 | 4 |
| | 2 | | | | 0.063 | 0.063 | 0.25 | ND | 1 | 0.125 | 4 |
| 62 | 1 | 2 | | | 0.5 | 0.5 | 0.5 | 0.5 | 1 | 0.25 | 2 |
| | 2 | | | | 0.125 | 2 | 0.5 | ND | ND | 0.25 | 4 |
| 63 | 1 | 2 | | | 0.25 | 0.25 | 0.25 | 1 | 1 | 0.5 | 4 |
| 64 | 1 | 1 | | | 0.125 | 0.25 | 0.5 | 1 | 4 | 0.5 | 16 |
| 65 | 3 | | | | 2 | 2 | 16 | 8 | >32 | 8 | >32 |
| 66 | 1 | 8 | | | 8 | 8 | >32 | >32 | >32 | >32 | >32 |
| 67 | 1 | 4 | | | 0.5 | 4 | 4 | 8 | >32 | 4 | >32 |
| 68 | 1 | 16 | | | 4 | ND | 32 | >32 | 16 | >32 | >32 |
| 69 | 1 | 2 | | | 0.125 | 0.125 | 0.125 | 0.5 | 4 | 0.5 | 32 |
| 70 | 1 | 16 | | | 8 | 8 | >32 | >32 | >32 | >32 | >32 |
| 71 | 1 | 16 | | | 2 | 2 | 32 | 16 | >32 | 8 | >32 |
| 72 | 1 | 32 | | | >32 | >32 | >32 | >32 | >32 | >32 | >32 | wherein
Aerobic bacteria:

| Strain # | Species | ATCC# | Strain description |
|---|---|---|---|
| SAU.42 | Staphylococcus aureus | 29213 | CLSI reference strain for broth microdilution MIC assay obtained from the ATCC |
| SAU.399 | Staphylococcus aureus | 43300 | CLSI Methicillin and Oxacillin Resistant Clinical Isolate obtained from the ATCC |
| SAU.278 | Staphylococcus aureus | n/a | Daptomycin resistant mutant (D10)-liquid serial passage mutant derived from parent S. aureus 42 |
| EFM.14 | Enterococcus faecium | 6569 | FDA test organism in AOAC test for germicidal activity obtained from the ATCC |
| EFM.384 | Enterococcus faecium | n/a | Daptomycin resistant mutant (14-A)-liquid serial passage mutant derived from parent E. faecium 14 |
| EFS.201 | Enterococcus faecalis | 49452 | Quality control strain for API products obtained from the ATCC |
| EFS.312 | Enterococcus faecalis | n/a | Daptomycin resistant mutant (EFA)-liquid serial passage mutant derived from parent E. faecalis 201 |
| | C. difficile | | |

Anaerobic bacteria recovered from toxin-positive fecal specimens:

| RMA # | Species |
|---|---|
| 11001-P1 | Clostridium difficile |
| 14001-P1 | Clostridium difficile |
| 11027-P1 | Clostridium difficile |
| 14043-P1 | Clostridium difficile |
| 13027-P1 | Clostridium difficile |
| 16001-P1 | Clostridium difficile |
| 1001-P1 | Clostridium difficile |
| 1002-P1 | Clostridium difficile |
| 1003-P1 | Clostridium difficile |
| 2001-P1 | Clostridium difficile |
| 5001-P1 | Clostridium difficile |
| 9001-P1 | Clostridium difficile |
| 9002-P1 | Clostridium difficile |
| 11035-P1 | Clostridium difficile |
| 11037-P1 | Clostridium difficile |
| 11038-P1 | Clostridium difficile |
| 14044-P1 | Clostridium difficile |
| 1004-P1 | Clostridium difficile |
| 1006-P1 | Clostridium difficile |
| 2002-P1 | Clostridium difficile |
| 1302-P1 | Clostridium difficile |
| 13030-P1 | Clostridium difficile |
| 14045-P1 | Clostridium difficile |
| 67001-P1 | Clostridium difficile |
| 25001-P1 | Clostridium difficile |
| 11041-P1 | Clostridium difficile |
| 11042-P1 | Clostridium difficile |
| 1007-P1 | Clostridium difficile |
| 1008-P1 | Clostridium difficile |

NAP1 *Clostridium difficile* strain recovered from toxin-positive fecal specimens No. RMA 19139 REA B1,
RMA refers to RM Alden Labs, Santa Monica, Calif.

Example 20

In Vivo Biological Activity

Syrian golden hamsters were pretreated with 10 mg/kg clindamycin subcutaneously 24 hours before bacterial challenge. An inoculum of 20 *C. difficile* spores (ATCC #43596) in sterile saline was administered orally. Treatment was initiated 4 hours post-inoculation with dH$_2$O, metronidazole (MET), vancomycin (VAN), or a compound of the present invention. Oral dosing regimens for VAN and compounds of Formula I were 0.5 mg/kg once daily for 5 days. MET was administered at 70 mg/kg three times daily for 5 days. CDAD was confirmed as the cause of death by observations at necropsy, including wet tail and/or macroscopic cecal alterations. The % protection provided by each therapy tested was calculated at 1 and 21 days post-dosing. The mean percentage protection value of representative compounds of the present invention are listed in Table VIII.

TABLE VIII

In Vivo Mean Protection Values

| Compound # | Mean % Protection | | Study n | Hamster n |
|---|---|---|---|---|
| | 1 Day Post Dosing | 21 Days Post Dosing | | |
| dH$_2$O | 0 | 0 | 6 | 30 |
| 16 | 100 | 85 | 2 | 13 |
| 22 | 85 | 38 | 2 | 13 |
| 43 | 100 | 60 | 1 | 5 |
| 34 | 85 | 38 | 2 | 13 |
| 33 | 85 | 69 | 2 | 13 |
| 49 | 100 | 100 | 1 | 8 |
| 28 | 100 | 100 | 1 | 8 |
| 52 | 100 | 88 | 1 | 8 |
| 53 | 13 | 0 | 1 | 8 |
| 54 | 0 | 0 | 2 | 16 |
| Metronidazole | 100 | 0 | 2 | 10 |
| Vancomycin | 90 | 62 | 3 | 21 |

*C. difficile* infected control hamsters (n=30), dosed with sterile water, all died within 48 hours of inoculation. MET (n=10) or VAN (n=21) treatments achieved % protections of, respectively, 100% or 90% at 1 day post-dosing, and 0% or 62% at 21 days post-dosing. Compounds of the present invention provided % protections as high as 100% at both 1 and 21 days post-dosing.

It is believed that compounds with a structural resemblance to those of the present invention are disclosed in EP Patent No. 0095295(295), and U.S. Pat. Nos. Re. 32,310, 7,335,725 ('725) and 6,911,525 ('525) all of which are incorporated herein in their entirety. See. e.g., compound 39 herein, or described in '295 (Example 73). However, these previously known compounds demonstrate significantly less activity against gram positive bacteria, such as *C. difficile* and other various bacterial strains, including those that are resistant to daptomycin. For example, compound 39 of the '295 patent is believed to be the only previously known compound that bears a structural resemblance to compounds 32 and 33 of the present invention. Novel compounds 32 and 33 of the present invention exhibit unexpected and improved properties against *C. difficile* as evidenced from Table VII. The MIC$_{90}$ values for compounds 32 and 33 against *C. difficile* are 4 and at most 1, whereas the MIC$_{90}$ for compound 39 is 16. In addition, compound 32 and 33 show improved properties over various other strains of gram-positive bacteria, including those that are resistant to daptomycin.

In yet a further aspect, as shown by Table IX, comparative data analyses of compounds 48 to 50 of the present invention with known compounds III and 112 as described in '725 and '525 reveal that compounds 48 to 50 exhibit superior and unexpected activity against gram positive bacteria, including those that are resistant to daptomycin. For example, compounds 49 and 50 have MIC values of at most 0.3 against Sa42 whereas the MIC values for compounds III and 112 are at most 1.0 and 0.5 respectively. Also, compound 49 shows increased and unexpected activity as a whole against Sa399, Sa278, Efm14, Efm384, Efs201, and Efs 312 when compared to 111.

TABLE IX

| Data Comparison of Compounds 48 to 50 with 111 and 112 of '725 and '525 | | | | | | | | | |
|---|---|---|---|---|---|---|---|---|---|
| Compound # | Lot # | C. diff $MIC_{90}$ | Sa42 | Sa399 | Sa278 | Efm14 | Efm384 | Efs201 | Efs312 |
| Daptomycin | n/a | 2 | 0.5 | 0.5 | 8 | 4 | >32 | 2 | >32 |
| 1 | 1 |  | 8 | 2 | >32 | 32 | >32 | 32 | >32 |
| 48 | 1 | 2 |  |  |  |  |  |  |  |
|  | 2 | 2 | 1 | 1 | 2 | 2 | 32 | 1 | >32 |
|  | 3 |  | 0.25 | 0.25 | 4 | ND | ND | 1 | 32 |
| 49 | 1 | 1 |  |  |  |  |  |  |  |
|  | 2 |  | 0.063 | 0.063 | 1 | 0.25 | 4 | 0.125 | 8 |
|  | 3 |  |  |  |  |  |  |  |  |
|  | 4 |  | 0.25 | 0.25 | 1 | 0.5 | 4 | 0.25 | 4 |
|  | 5 |  | 0.25 | 0.25 | 1 | 0.5 | 4 | 0.25 | 4 |
|  | 6 |  | 0.25 | 0.5 | 1 | 0.5 | 4 | 0.5 | 4 |
|  | 7 | 0.5 |  |  |  |  |  |  |  |
|  | 8 | 0.5 |  |  |  |  |  |  |  |
|  | 9 | 0.275 |  |  |  |  |  |  |  |
| 50 | 2 | 0.5 | 0.25 | 0.5 | 1 | 1 | 4 | 0.25 | 4 |
| 111 of '725 and '525 |  | ND | 0.781 1.0 | 0.39 | 6.25 | 3.13 | 12.5 | 1.56 | 50 |
| 112 of '725 and '525 |  | ND | 0.5 0.39 | 0.39 | 1.56 | 0.39 | 1.56 | <0.1 | 6.25 |

Thus, the aforementioned compounds disclosed in the prior art are believed to be completely different from compounds of the present invention, which are novel and active against gram-positive bacteria, show increased activity against *Clostridium difficile*, and/or show unexpected activity against bacteria that are resistant to daptomycin.

While some embodiments have been shown and described, various modifications and substitutions may be made thereto without departing from the spirit and scope of the invention. For example, it is not intended that the claims set forth hereinafter be construed narrower than the literal language thereof, nor is it intended that exemplary embodiments from the specification be read into the claims. Accordingly, it is to be understood that the present invention has been described herein by way of illustration only, and that such descriptions do not constitute limitations on the scope of the claims.

What is claimed is:

1. A compound of Formula I

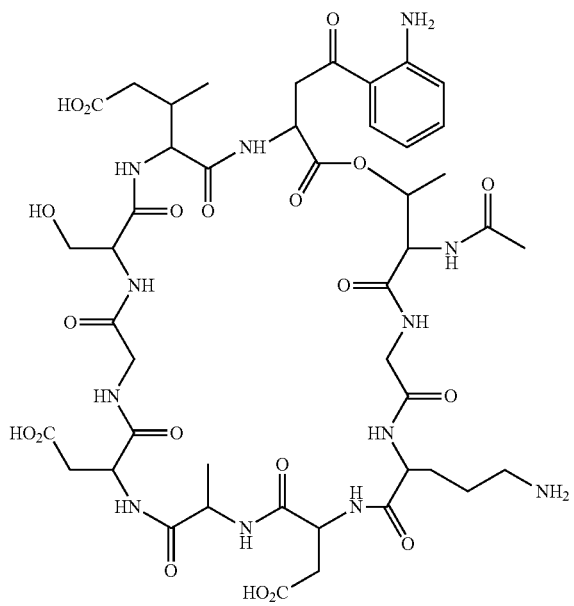

(I)

and pharmaceutically acceptable salts thereof, wherein:

R is

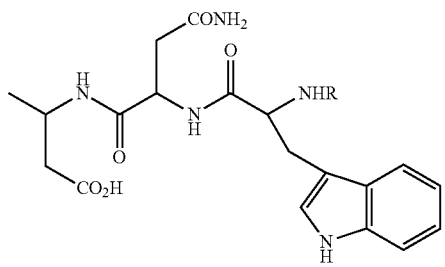

-continued

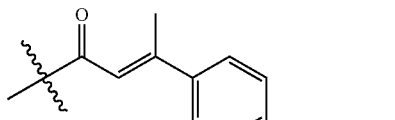

and v is an integer from 3 to 7.

2. A compound of Formula (II)

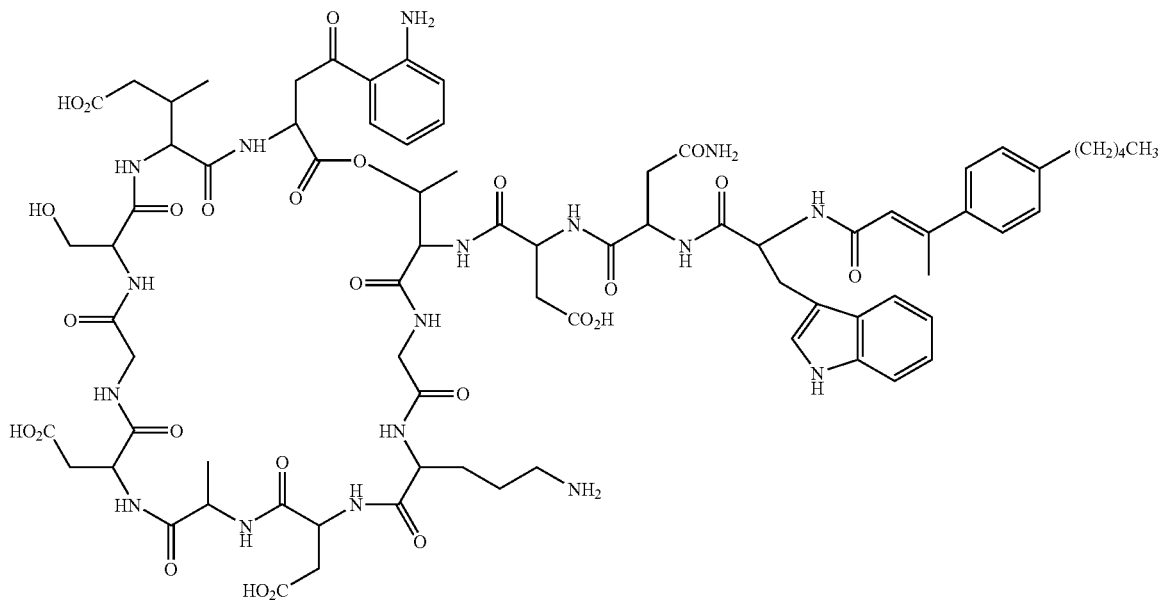

or a pharmaceutically acceptable salt thereof.

3. A pharmaceutical composition comprising a compound according to claim 2, or a pharmaceutically acceptable salt thereof, and a pharmaceutically acceptable carrier.

4. A method of treating a bacterial infection comprising administering to a subject in need thereof a therapeutically-effective amount of the pharmaceutical composition according to claim 3.

5. The method according to claim 4, wherein the subject is a human, an animal, a cell culture, or a plant.

6. The method according to claim 5, wherein the subject is a human.

7. The method according to claim 4, wherein the bacterial infection is caused by a gram-positive bacteria.

8. The method according to claim 7, wherein the bacteria is a *Clostridium difficile* strain.

9. The method according to claim 8, wherein the *Clostridium difficile* strain is a Nap1 *Clostridium difficile* strain.

10. The method according to claim 7, wherein the bacteria is an antibiotic resistant bacteria, wherein the antibiotic resistant bacteria is not resistant to the composition according to claim 3.

11. The method according to claim 10, wherein the antibiotic resistant bacteria is daptomycin resistant *Staphylococcus aureus*, daptomycin resistant *Enterococcus faecium*, daptomycin resistant *Enterococcus faecalis*, methicillin resistant *Staphylococcus aureus*, or a mixture of bacteria comprising at least one of the antibiotic resistant bacteria.

12. The method according to claim 10, wherein the antibiotic-resistant bacteria is resistant to vancomycin, methicillin, glycopeptide antibiotics, penicillin or daptomycin.

13. The method according to claim 7, wherein the bacterial infection is *Clostridium Difficile* Associated Disease (CDAD).

14. The method according to claim 13, wherein the *Clostridium Difficile* Associated Disease arises from or is exacerbated by a Nap1 *Clostridium difficile* infection.

15. The compound according to claim 2, wherein the compound is of the formula:

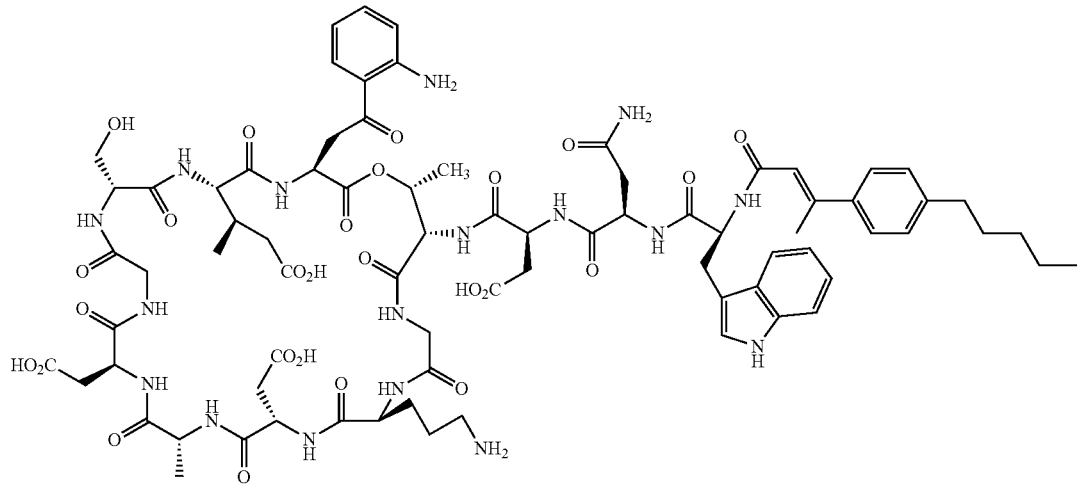 [SMILES: CCCCCc1ccc(/C(C)=C/C(=O)N[C@@H](Cc2c[nH]c3ccccc23)C(=O)N[C@H](CC(N)=O)C(=O)N[C@@H](CC(=O)O)C(=O)N[C@@H]2C(=O)NCC(=O)N[C@@H](CCCN)C(=O)N[C@@H](CC(=O)O)C(=O)N[C@H](C)C(=O)N[C@@H](CC(=O)O)C(=O)NCC(=O)N[C@H](CO)C(=O)N[C@@H]([C@H](C)CC(=O)O)C(=O)N[C@@H](CC(=O)c3ccccc3N)C(=O)O[C@@H]2C)cc1]

or a pharmaceutically acceptable salt thereof.

\* \* \* \* \*

UNITED STATES PATENT AND TRADEMARK OFFICE
CERTIFICATE OF CORRECTION

PATENT NO. : 8,507,647 B2  Page 1 of 1
APPLICATION NO. : 12/641465
DATED : August 13, 2013
INVENTOR(S) : Metcalf, III et al.

It is certified that error appears in the above-identified patent and that said Letters Patent is hereby corrected as shown below:

In the Claims

In claim 1, column 99, lines 42-65, and column 100, lines 24-38,

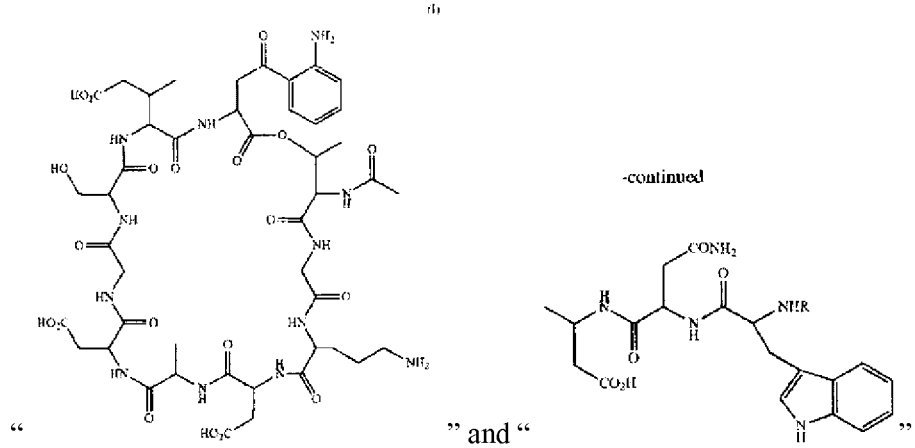

" and "

should read

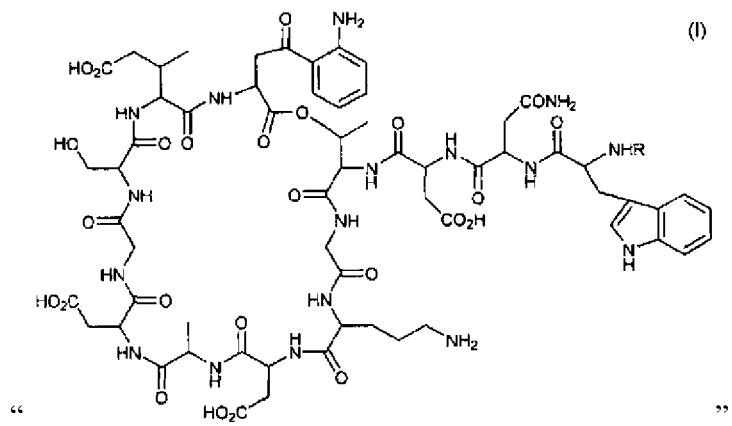

" "

Signed and Sealed this
Nineteenth Day of November, 2013

Teresa Stanek Rea
*Deputy Director of the United States Patent and Trademark Office*